United States Patent [19]
Korneluk et al.

[11] Patent Number: 6,107,041
[45] Date of Patent: *Aug. 22, 2000

[54] DETECTION AND MODULATION OF IAPS FOR THE DIAGNOSIS AND TREATMENT OF PROLIFERATIVE DISEASE

[75] Inventors: Robert G. Korneluk; Alexander E. MacKenzie, both of Ontario; Peter Liston; Stephen Baird, both of Ottawa; Benjamin K. Tsang, Nepean; Christine Pratt, Ontario, all of Canada

[73] Assignee: Apoptogen, Inc., Ottawa, Canada

[ * ] Notice: This patent is subject to a terminal disclaimer.

[21] Appl. No.: 09/212,971

[22] Filed: Dec. 16, 1998

Related U.S. Application Data

[62] Division of application No. 08/800,929, Feb. 13, 1997.
[60] Provisional application No. 60/030,590, Nov. 14, 1996, and provisional application No. 60/017,354, Apr. 26, 1996.

[51] Int. Cl.[7] .............................. C12Q 1/68; C12N 15/00; C12N 15/85; C12N 15/86; C12N 15/63; C07H 21/04

[52] U.S. Cl. .............................. 435/6; 435/69.1; 435/320; 435/325; 435/375; 536/23.1; 536/23.5

[58] Field of Search .......................... 435/7.21, 6, 320.1, 435/375, 18; 514/44

[56] References Cited

U.S. PATENT DOCUMENTS 5,834,216 11/1998 Roizman et al. ....................... 435/7.21

FOREIGN PATENT DOCUMENTS

| | | | |
|---|---|---|---|
| WO 94/06814 | 3/1994 | WIPO . | |
| WO 98/22131 | 5/1995 | WIPO . | |
| WO 95/19431 | 7/1995 | WIPO . | |
| WO 9528497 | 10/1995 | WIPO ............................ | C12Q 1/68 |
| WO 96/12016 | 4/1996 | WIPO . | |
| WO 97/06255 | 2/1997 | WIPO . | |
| WO 97/26331 | 7/1997 | WIPO . | |

OTHER PUBLICATIONS

Birnbaum et al., "An apoptosis–inhibiting gene from a nuclear polyhedrosis virus encoding a polypeptide with Cys/His sequence motifs", J. of Virol., 68:2521, (1994).
Campbell, Monoclonal Antibody Technology, Elsevier Science, Publishers B.V. New York, NY, (1984).
Cheng et al., "Staurosporine, K–252a, and K–252b Stabilize Calcium Homeostasis and Promote Survival of CNS Neurons in the Absence of Glucose", J. Neurochem., 62:1319–1329, (1994).
Clem et al., "Anti–apoptotic genes of baculovirus", Cell Death and Differentiation, 3:9–16, (1996).
Clem et al., "Induction and inhibition of apoptosis by insect viruses", Apoptosis II: The Molecular Basis of Apoptosis in Disease, Cold Spring Harbor Laboratory Press, p. 89, (1994).
Clem et al., "Prevention of apoptosis by a baculovirus gene during infection of insect cells", Science 254:1388, (1991).
Clem et al., "Control of programmed cell death by the baculovirus genes p35 and IAP", Mol. and Cell. Biology, 14:5212, (1994).
Crocker et al., "Adenovirus–mediated NAIP overexpression confers protection against global ischemia", Database Biosis, Abstract, (1996).
Crook et al., "An apoptosis–inhibiting baculovirus gene with a zinc finger–like motif", J. of Virol., 67:2168, (1993).
Dhein et al., "Autocrine T–cells suicide mediated by APO–1 (Fas/CD95)", Abstract, Nature, 373:438, (1995).
Duckett et al., "A conserved family of cellular genes related to the baculovirus IAP gene and encoding apoptosis inhibitors", The EMBO Journal, 15:2685–2694, (1996).
Fernandez et al., "Differential sensitivity of normal and Ha–ras–transformed C3H mouse embryo fibroblasts to tumor necrosis factor . . . ", Abstract, Oncogene, 9:2009, (1994).
Ferrari et al., "N–acetylcysteine (D– and L–stereoisomers) prevents apoptotic death of neuronal cells", Abstract, J. Neurosci., 1516:2857, (1995).
Fisher et al., "Dominant interfering Fas gene mutations impair apoptosis in a human autoimmune lymphoproliferative syndrome", Cell, 81:935, (1995).
Francis et al., "The Response of GABAergic and Cholinergic Neurons to Transient Cerebral Ischemia", Brain Res., 243:271–278, (1982).
Gibellini et al., "Tat–expression Jurkat cells show an increased resistance to differnt apoptic stimuli . . . ", Abstract, Br. J. Haematol., 89:24, (1995).
Glicksman et al., "K–252a and Staurosporing Promote Choline Acetyltransferase Activity in Rat Spinal Cord Cultures", J. Neurochem., 61:210–221, (1993).
Glicksman et al., "K–252a Analog Prevents Developmentally Programmed Motoneuron Death and the Loss of Chat Activity in Adult Motoneurons in vivo", Soc. Neuro. Abst., 441, (1994).
Glicksman et al., "K–252a Promotes Survival and Choline Acetyltransferase Activity in Striatal and Basal Forebrain Neuronal Cultures", J. Neurochem., 64:1502–1512, (1995).
Golstein et al., "Homology between reaper and the cell death domains of Fas and TNFR1", Cell 81:185, (1995).
Goruppi et al., "Dissection of c–myc domains involved in S phase induction of NIH3T3 fibroblasts", Abstract, Oncogene, 9:1537, (1994).
Harrington et al., "c–Myc–induced apoptosis in fibroblasts is inherited by specific cytokines", Abstract, EMBO J. 13:3286, (1994).

(List continued on next page.)

*Primary Examiner*—George C. Elliott
*Assistant Examiner*—Janets Epps
*Attorney, Agent, or Firm*—Clark & Elbing LLP; Kristina Bieker-Brady

[57] ABSTRACT

Disclosed are diagnostic and prognostic kits for the detection and treatment of proliferative diseases such as ovarian cancer, breast cancer, and lymphoma. Also disclosed are cancer therapeutics utilizing IAP antisense nucleic acids IAP fragments, and antibodies which specifically bind IAP polypeptides.

27 Claims, 33 Drawing Sheets

OTHER PUBLICATIONS

Itoh et al., "A novel protein required for apoptosis . . . ", Abstract, J. Biol. Chem., 268:10932, (1993).

Katsikis et al., "Fas antigen stimulation induces marked apoptosis of T lymphocytes in human immunodeficiency virus–infected individuals", Abstract, J. Exp. Med., 1815:2029, (1995).

Kerr, "Neglected opportunities in apoptosis research", Trends in Cell Biology, 5:55, (1995).

Korsmeyer, "Regulators of cell death", TIG 11:101, (1995).

Li et al., "Induction of apoptosis in uninfected lymphocytes by HIV–1 Tat protein", Abstract, Science, 268:429, (1995).

Liston et al., "Suppression of apoptosis in mammalian cells by NAIP and a related family of IAP genes", Nature, 397:349–353, (1993).

Martin et al., "HIV–1 infection of human CD4+ T cells in vitro . . . ", Abstract, J. Immunol., 152:330, (1994).

Melino et al., "Tissue transglutaminase and apoptosis: sense and antisense transfection studies . . . ", Abstract, Mol. Cell. Biol., 14:6584, (1994).

Murayama et al., "Immunocytochemical and ultrastructural studies of Werdnig–Hoffmann disease", Acta Neuropathol., 81:408–417, (1991).

Muro–Cacho et al., "Analysis of apoptosis in lymph nodes of HIV–infected persons . . . ", Abstract, J. Immunol., 154:5555, (1995).

Nakanshi et al., "K–252a, a Novel Microbial Product, Inhibits Smooth Muscle Myosin Light Chain Kinase", J. Biol. Chem., 23:6215–6219, (1988).

Nunez et al., "The Bcl–2 family of proteins: regulators of cell death and survival", Trends in Cell Biology, 4:399, (1994).

Osborne et al., "Essential genes that regulate apoptosis", Trends in Cell Biology, 4:394, (1994).

Peterson et al., "Loss of GABAergic neurons in medial septum after fimbria–fornix transection", Neurosci. Lett., 76:140–144, (1987).

Pulsinelli et al., "Temporal Profile of Neuronal Damage in a Model of Transient Forebrain Ischemia", Ann. Neurol., 11:491–498, (1982).

Rabizadeh et al., "Expression of the baculovirus p35 gene inhibits mammalian neural cell death", Abstract, J. Neurochem., 61:2318, (1993).

Ridoux et al., "The use of adenovirus vectors for intracerebral grafting of transfected nervous cells", Neuroreport., 5(7):801–804, (1994).

Ridoux et al., "Adenoviral vectors as functional retrograde neuronal tracers", Brain Res., 648(1):171–175, (1994).

Ridoux et al., "Ex vivo culture of adult microglial cells from previously lesioned rat brains", C.R. Acad. Sci. III, 317(3):217–224, (1994).

Rieux–Laucat et al., "Mutations in Fas associated with human lymphoproliferative syndrome and autoimmunity", Science, 268:1347, (1995).

Robertson et al., "Neuroprotective effects of K252a in cerebral ischemia: The NAIP connection", Database Biosis Abstract (1996).

Rosenbaum et al., "Evidence for hypoxia–induced, programmed cell death of cultured neurons", Abstract, Ann. Neurol., 376:864, (1994).

Rothe et al., "The TNFR2–TRAF signaling complex Contains Two Novel Proteins Related to Baculoviral Inhibitor of Apoptosis Proteins", Cell, 80:167, (1995).

Roy et al., "The gene for neuronal apoptosis inhibitory protein is partially deleted in individuals with spinal muscular atrophy", Cell, 80:167, (1995).

Sato et al., "Neuronal differentation of PC12 cells as a result of prevention of cell death by bcl–2", Abstract, J. Neurobiol., 25:1227, (1994).

Sauer et al., "Progressive degeneration of nigrostriatal dopamine neurons following intrastriatal terminal lesions with 6–hydroxydopamine . . . ", Neuroscience, 59(2):401–415, (1994).

Semba et al., "Organization of central cholinergic systems", Progress in Brain Res., 79:36–63, (1989).

Smith–Swintosky et al., "K252A, K252B and Staurosporine Increase Hippocampal Neuron Survival and Improve Water Maze Performance after Kainate", Soc. Neuro. Abst., 2130, (1995).

Steiman, et al., "Infantile Neuronal Degeneration Masquerading as Werdnig–Hoffmann Disease", Ann. Neurol., 8:317–324, (1980).

Steller, "Mechanisms and Genes of Cellular Suicide", Science, 267:1445, (1995).

Talley et al., "Tumor necrosis factor alpha–induced apoptosis in human neuronal cells . . . ", Abstract, Mol. Cell. Biol., 1585:2359, (1995).

Terai et al., "Apoptosis as a mechanism of cell death in cultured T lymphoblasts acutely infected with HIV–1", Abstract, J. Clin. Invest., 87:1710, (1991).

Tetzlaff et al., "Changes in cytoskeletal proteins in the rat facial nucleus following axotomy", J. Neurosci. 8(9):3181–3189, (1988).

Towfighi et al., "Is Werdnig–Hoffman Disease a Pure Lower Motor Neuron Disorder?", Acta Neuropathol., 65:270–280, (1985).

Vossbeck et al., "Direct transforming activity of TGF–beta on rat fibroblasts", Abstract, Int. J. Cancer, 61:92, (1995).

Walkinshaw et al., "Induction of apoptosis in catecholaminergic PC12 cells by L–DOPA . . . ", Abstract, J. Clin. Invest. 95:2458, (1995).

Westendorp et al., "Sensitization of T cells to CD95–mediated apoptosis by HIV–1 Tat and gp120", Nature, 375:497, (1995).

White et al., "Genetic control of programmed cell death in Drosphila", Science, 264:677, (1994).

Williams et al., "Apoptosis: final control point in cell biology", Trends in Cell Biology 2:263, (1992).

Wyllie, "Death gets a brake", Nature, 369:272, (1994).

Xu et al., "Elevation of neuronal expression of NAIP reduces ischemic damage in the rat hippocampus", Nature Medicine 3(9):997–1004, (1997).

Xu et al., "Distribution of Neuronal Apoptosis Inhibitory Protein–Like Immunoreactivity in the Rat Central Nervous System", The Journal of Comparative Neurology 382:247–259, (1997).

| | | |
|---|---|---|
| SEQ.ID 3 - 1 | GAAAAGGTGGACAAGTCCTATTTTCAAGAGAAGATGACTTTTAACAGTTTTGAAGGATCT | 60 |
| SEQ.ID 4 - 1 |                                         M  T  F  N  S  F  E  G  S | 9 |
| 61 | AAAACTTGTGTACCTGCAGACATCAATAAGGAAGAAGAATTTGTAGAAGAGTTTAATAGA | 120 |
| 10 | K  T  C  V  P  A  D  I  N  K  E  E  E  F  V  E  E  F  N  R | 29 |
| 121 | TTAAAAACTTTTGCTAATTTTCCAAGTGGTAGTCCTGTTTCAGCATCAACACTGGCACGA | 180 |
| 30 | L  K  T  F  A  N  F  P  S  G  S  P  V  S  A  S  T  L  A  R | 49 |
| 181 | GCAGGGTTTCTTTATACTGGTGAAGGAGATACCGTGCGGTGCTTTAGTTGTCATGCAGCT | 240 |
| 50 | A  G  F  L  Y  T  G  E  G  D  T  V  R  C  F  S  C  H  A  A | 69 |
| 241 | GTAGATAGATGGCAATATGGAGACTCAGCAGTTGGAAGACACAGGAAAGTATCCCCAAAT | 300 |
| 70 | V  D  R  W  Q  Y  G  D  S  A  V  G  R  H  R  K  V  S  P  N | 89 |
| 301 | TGCAGATTTATCAACGGCTTTTATCTTGAAAATAGTGCCACGCAGTCTACAAATTCTGGT | 360 |
| 90 | C  R  F  I  N  G  F  Y  L  E  N  S  A  T  Q  S  T  N  S  G | 109 |
| 361 | ATCCAGAATGGTCAGTACAAAGTTGAAAACTATCTGGGAAGCAGAGATCATTTTGCCTTA | 420 |
| 110 | I  Q  N  G  Q  Y  K  V  E  N  Y  L  G  S  R  D  H  F  A  L | 129 |
| 421 | GACAGGCCATCTGAGACACATGCAGACTATCTTTTGAGAACTGGGCAGGTTGTAGATATA | 480 |
| 130 | D  R  P  S  E  T  H  A  D  Y  L  L  R  T  G  Q  V  V  D  I | 149 |
| 481 | TCAGACACCATATACCCGAGGAACCCTGCCATGTATaGTGAAGAAGCTAGATTAAAGTCC | 540 |
| 150 | S  D  T  I  Y  P  R  N  P  A  M  Y  S  E  E  A  R  L  K  S | 169 |
| 541 | TTTCAGAACTGGCCAGACTATGCTCACCTAACCCCAAGAGAGTTAGCAAGTGCTGGACTC | 600 |
| 170 | F  Q  N  W  P  D  Y  A  H  L  T  P  R  E  L  A  S  A  G  L | 189 |
| 601 | TACTACACAGGTATTGGTGACCAAGTGCAGTGCTTTTGTTGTGGTGGAAAAACTGAAAAAT | 660 |
| 190 | Y  Y  T  G  I  G  D  Q  V  Q  C  F  C  C  G  G  K  L  K  N | 209 |
| 661 | TGGGAACCTTGTGATCGTGCCTGGTCAGAACACAGGCGACACTTTCCTAATTGCTTCTTT | 720 |
| 210 | W  E  P  C  D  R  A  W  S  E  H  R  R  H  F  P  N  C  F  F | 229 |
| 721 | GTTTTGGGCCGGAATCTTAATATTCGAAGTGAATCTGATGCTGTGAGTTCTGATAGGAAT | 780 |
| 230 | V  L  G  R  N  L  N  I  R  S  E  S  D  A  V  S  S  D  R  N | 249 |
| 781 | TTCCCAAATTCAACAAATCTTCCAAGAAATCCATCCATGGCAGATTATGAAGCACGGATC | 840 |
| 250 | F  P  N  S  T  N  L  P  R  N  P  S  M  A  D  Y  E  A  R  I | 269 |
| 841 | TTTACTTTTGGGACATGGATATACTCAGTTAACAAGGAGCAGCTTGCAAGAGCTGGATTT | 900 |
| 270 | F  T  F  G  T  W  I  Y  S  V  N  K  E  Q  L  A  R  A  G  F | 289 |
| 901 | TATGCTTTAG̊GTGAAGGTGATAAAGTAAAGTGCTTTCACTGTGGAGGAGGGCTAACTGAT | 960 |
| 290 | Y  A  L  G̊  E  G  D  K  V  K  C  F  H  C  G  G  G  L  T  D | 309 |
| 961 | TGGAAGCCCAGTGAAGACCCTTGGGAACAACATGCTAAATGGTATCCAGG̊GTGCAAATAT | 1020 |
| 310 | W  K  P  S  E  D  P  W  E  Q  H  A  K  W  Y  P  G  C  K  Y | 329 |
| 1021 | CTGTTAGAACAGAAGGGACAAGAATATATAAACAATATTCATTTAACTCATTCACTTGAG | 1080 |
| 330 | L  L  E  Q  K  G  Q  E  Y  I  N  N  I  H  L  T  H  S  L  E | 349 |

```
                          3 4                                      4 5
1081 GAGTGTCTGGTAAGAACTACTGAGAAAACACCATCACTAACTAGAAGAATTGATGATACC 1140
 350  E  C  L  V  R  T  T  E  K  T  P  S  L  T  R  R  I  D  D  T   369

1141 ATCTTCCAAAATCCTATGGTACAAGAAGCTATACGAATGGGGTTCAGTTTCAAGGACATT 1200
 370  I  F  Q  N  P  M  V  Q  E  A  I  R  M  G  F  S  F  K  D  I   389

1201 AAGAAAATAATGGAGGAAAAAATTCAGATATCTGGGAGCAACTATAAATCACTTGAGGTT 1260
 390  K  K  I  M  E  E  K  I  Q  I  S  G  S  N  Y  K  S  L  E  V   409

1261 CTGGTTGCAGATCTAGTGAATGCTCAGAAAGACAGTATGCAAGATGAGTCAAGTCAGACT 1320
 410  L  V  A  D  L  V  N  A  Q  K  D  S  M  Q  D  E  S  S  Q  T   429

1321 TCATTACAGAAAGAGATTAGTACTGAAGAGCAGCTAAGGCGCCTGCAAGAGGAGAAGCTT 1380
 430  S  L  Q  K  E  I  S  T  E  E  Q  L  R  R  L  Q  E  E  K  L   449

1381 TGCAAAATCTGTATGGATAGAAATATTGCTATCGTTTTTGTTCCTTGTGGACATCTAGTC 1440
 450  C  K  I  C  M  D  R  N  I  A  I  V  F  V  P  C  G  H  L  V   469

1441 ACTTGTAAACAATGTGCTGAAGCAGTTGACAAGTGTCCCATGTGCTACACAGTCATTACT 1500
 470  T  C  K  Q  C  A  E  A  V  D  K  C  P  M  C  Y  T  V  I  T   489

1501 TTCAAGCAAAAAATTTTTATGTCTTAATCTAACTCTATAGTAGGCATGTTATGTTGTTCT 1560
 490  F  K  Q  K  I  F  M  *                                        497

1561 TATTACCCTGATTGAATGTGTGATGTGAACTGACTTTAAGTAATCAGGATTGAATTCCAT 1620
1621 TAGCATTTGCTACCAAGTAGGAAAAAAAATGTACATGGCAGTGTTTTAGTTGGCAATATA 1680
1681 ATCTTTGAATTTCTTGATTTTTCAGGGTATTAGCTGTATTATCCATTTTTTTTACTGTTA 1740
1741 TTTAATTGAAACCATAGACTAAGAATAAGAAGCATCATACTATAACTGAACACAATGTGT 1800
1801 ATTCATAGTATACTGATTTAATTTCTAAGTGTAAGTGAATTAATCATCTGGATTTTTTAT 1860
1861 TCTTTTCAGATAGGCTTAACAAATGGAGCTTTCTGTATATAAATGTGGAGATTAGAGTTA 1920
1921 ATCTCCCCAATCACATAATTTGTTTTGTGTGAAAAAGGAATAAAATTGTTCCATGCTGGTG 1980
1981 GAAAGATAGAGATTGTTTTTAGAGGTTGGTTGTTGTGTTTTAGGATTCTGTCCATTTTCT 2040
2041 TTTAAAGTTATAAACACGTACTTGTGCGAATTATTTTTTTAAAGTGATTTGCCATTTTTG 2100
2101 AAAGCGTATTTAATGATAGAATACTATCGAGCCAACATGTACTGACATGGAAAGATGTCA 2160
2161 AAGATATGTTAAGTGTAAAATGCAAGTGGCAAAACACTATGTATAGTCTGAGCCAGATCA 2220
2221 AAGTATGTATGTTTTAATATGCATAGAACAAAAGATTTGGAAAGATATACACCAAACTG 2280
2281 TTAAATGTGGTTTCTCTTCGGGGAGGGGGGATTGGGGGAGGGGCCCCAGAGGGGTTTTA 2340
2341 TAGGGGCCTTTTCACTTTCTACTTTTTTCATTTTGTTCTGTTCGAATTTTTTATAAGTAT 2400
2401 GTATTACTTTTGTAATCAGAATTTTTAGAAAGTATTTTGCTGATTTAAAGGCTTAGGCAT 2460
2461 GTTCAAACGCCTGCAAAACTACTTATCACTCAGCTTTAGTTTTTCTAATCCAAGAAGGCA 2520
2521 GGGCAGTTAACCTTTTTGGTGCCAATGTGAAATGTAAATGATTTTATGTTTTTCCTGCTT 2580
2581 TGTGGATGAAAAATATTTCTGAGTGGTAGTTTTTTGACAGGTAGACCATGTCTTATCTTG 2640
2641 TTTCAAAATAAGTATTTCTGATTTTGTAAAATGAAATATAAAATATGTCTCAGATCTTCC 2700
2701 AATTAATTAGTAAGGATTCATCCTTAATCCTTGCTAGTTTAAGCCTGCCTAAGTCACTTT 2760
2761 ACTAAAAGATCTTTGTTAACTCAGTATTTTAAACATCTGTCAGCTTATGTAGGTAAAAGT 2820
2821 AGAAGCATGTTTGTACACTGCTTGTAGTTATAGTGACAGCTTTCCATGTTGAGATTCTCA 2880
2881 TATCATCTTGTATCTTAAAGTTTCATGTGAGTTTTTACCGTTAGGATGATTAAGATGTAT 2940
2941 ATAGGACAAAATGTTAAGTCTTTCCTCTACCTACATTTGTTTTCTTGGCTAGTAATAGTA 3000
3001 GTAGATACTTCTGAAATAAATGTTCTCTCAAGATCCTTAAAACCTCTTGGAAATTATAAA 3060
```

```
3061 AATATTGGCAAGAAAAGAAGAATAGTTGTTTAAATATTTTTTAAAAAACACTTGAATAAG 3120
3121 AATCAGTAGGGTATAAACTAGAAGTTTAAAAATGCCTCATAGAACGTCCAGGGTTTACAT 3180
3181 TACAAGATTCTCACAACAAACCCATTGTAGAGGTGAGTAAGGCATGTTACTACAGAGGAA 3240
3241 AGTTTGAGAGTAAAACTGTAAAAAATTATATTTTTGTTGTACTTTCTAAGAGAAAGAGTA 3300
3301 TTGTTATGTTCTCCTAACTTCTGTTGATTACTACTTTAAGTGATATTCATTTAAAACATT 3360
3361 GCAAATTTATTTTATTTATTTAATTTTCTTTTTGAGATGGAGTCTTGCTTGTCACCCAGG 3420
3421 CTGGAGTGCAGTGGAGTGATCTCTGCTCACTGCAACCTCCGCCTTCTGGGTTCAAGCGAT 3480
3481 TCTCGTGCCTCAGCTTCCTGAGTAGCTGGAATTACAGGCAGGTGCCACCATGCCCGACTA 3540
3541 ATTTTTTTTATTTTTAGTAGAGACGGGGTTTCACCATGTTGGCCAGGCTGGTATCAAAC 3600
3601 TCCTGACCTCAAGAGATCCACTCGCCTTGCCCTCCCAAAGTGCTGGGATTACAGGCTTGA 3660
3661 GCCACCACGCCCGGCTAAAACATTGCAAATTTAAATGAGAGTTTTAAAAATTAAATAATG 3720
3721 ACTGCCCTGTTTCTGTTTTAGTATGTAAATCCTCAGTTCTTCACCTTTGCACTGTCTGCC 3780
3781 ACTTAGTTTGGTTATATAGTCATTAACTTGAATTTGGTCTGTATAGTCTAGACTTTAAAT 3840
3841 TTAAAGTTTTCTACAAGGGGAGAAAAGTGTTAAAATTTTTAAAATATGTTTTCCAGGACA 3900
3901 CTTCACTTCCAAGTCAGGTAGGTAGTTCAATCTAGTTGTTAGCCAAGGACTCAAGGACTG 3960
3961 AATTGTTTTAACATAAGGCTTTTCCTGTTCTGGGAGCCGCACTTCATTAAAATTCTTCTA 4020
4021 AAACTTGTATGTTTAGAGTTAAGCAAGACTTTTTTCTTCCTCTCCATGAGTTGTGAAAT 4080
4081 TTAATGCACAACGCTGATGTGGCTAACAAGTTTATTTTAAGAATTGTTTAGAAATGCTGT 4140
4141 TGCTTCAGGTTCTTAAAATCACTCAGCACTCCAACTTCTAATCAAATTTTTGGAGACTTA 4200
4201 ACAGCATTTGTCTGTGTTTGAACTATAAAAAGCACCGGATCTTTTCCATCTAATTCCGCA 4260
4261 AAAATTGATCATTTGCAAAGTCAAAACTATAGCCATATCCAAATCTTTTCCCCCTCCCAA 4320
4321 GAGTTCTCAGTGTCTACATGTAGACTATTCCTTTTCTGTATAAAGTTCACTCTAGGATTT 4380
4381 CAAGTCACCACTTATTTTACATTTTAGTCATGCAAAGATTCAAGTAGTTTTGCAATAAGT 4440
4441 ACTTATCTTTATTTGTAATAATTTAGTCTGCTGATCAAAAGCATTGTCTTAATTTTTGAG 4500
4501 AACTGGTTTTAGCATTTACAAACTAAATTCCAGTTAATTAATTAATAGCTTTATATTGCC 4560
4561 TTTCCTGCTACATTTGGTTTTTTCCCCTGTCCCTTTGATTACGGGCTAAGGTAGGGTAAG 4620
4621 AXXGGGTGTAGTGAGTGTATATAATGTGATTTGGCCCTGTGTATTATGATATTTTGTTAT 4680
4681 TTTTGTTGTTATATTATTTACATTTCAGTAGTTGTTTTTTGTGTTTCCATTTTAGGGGAT 4740
4741 AAAATTTGTATTTTGAACTATGAATGGAGACTACCGCCCCAGCATTAGTTTCACATGATA 4800
4801 TACCCTTTAAACCCGAATCATTGTTTTATTTCCTGATTACACAGGTGTTGAATGGGGAAA 4860
4861 GGGGCTAGTATATCAGTAGGATATACTATGGGATGTATATATATCATTGCTGTTAGAGAA 4920
4921 ATGAAATAAAATGGGGCTGGGCTCAGTGGCTCACGCCTGTAATCCCAGCACTTTGGGAGG 4980
4981 CTGAGGCAGGTGGATCACGAGGTCAGGAGATCGAGACCATCCTGGCTAACACGGTGAAAC 5040
5041 CCCGTCTCTACTAAAAACAGAAAATTAGCCGGGCGTGGTGGCGGGCGCCTGTAGTCCCA 5100
5101 GCTACTCGGGAGGCTGAGGCAGGAGAATGGTGTGAACCCGGGAGGCAGAGCTTGCAGTGA 5160
5161 GCCGAGATCTCGCCACTGCACTCCAGCCTGGGCAACAGAGCAAGACTCTGTCTCAAAAAA 5220
5221 AAAAAAAAAAG 5232
```

SEQ.ID 5 - 1 TTGCTCTGTCACCCAGTTTGGAGTGCAGTTATGCAGTCTCACACTGCAAGCTCTGCCTCA 60
61 TGGGCTCAAGTGAACCTCCTGCCTCAGCCTCTCAAGTAGCTGGGACCACAGGCAGGTGCC 120
121 ACCATGTCTGGCTAATTTTTGAGTTTCTTTGTAGAGATGGTGTTTTGCCAAGTCACCCAG 180
181 TTTGAGGCTGGTCTCAAACACCTGGGCTCAAGCAATCCATCTACCTCAGCCTCCCAAAGT 240
241 GCTGGGATTACAGGAGTGAGCCATGGCATGAGGCCTTGTGGGGTGTCTCTTTTAAATGAA 300
301 AGCATACTCTGTTTACGTATTTGATATGAAGGAATATCCTTCCTTTCCACAAAGACAAAA 360
361 ATTATCCTATTTTTCTCAAAACATATGTCCTTTTTCTCTACTTTTCATTTTTGTTACTTT 420
421 TGATGGACACATGTGTTACATTGATTTCACTTTCTCATAATTCTGCTGTAAGAAAAACAA 480
481 TAGTGCCAGTTCAATGACAAATAGCAACAGTCTGTTATTGCTAGACTGTTACTGTTAGTG 540
541 GAGACTACCAGAACAGTCAGTCCCAGTGTCAGGGAATCAAAGAGAACATGTTCCCTCTCT 600
601 AAAGGGCACAGCTGCTGCTCAGCTTTAGCTGATTGCTGCCCTGCAGGACTATAGGCCCAG 660
661 TGTTGCTAGATCTTTTGATGTTTCAAGAGAAGCTTGGAATCTAGAATGTGATGGGAAGTC 720
721 TCTTACATTTAAACATGTTGGCAATTAATGGTAAGATTTAAAAATACTGTGGTCCAAGAA 780
781 AAAAATGGATTTGGAAACTGGATTAAATTCAAATGAGGCATGCAGATTAATCTACAGCAT 840
841 GGTACAATGTGAATTTTCTGGTTTCTTTAATTGCACTGTAATTAGGTAAGATGTTAGCTT 900
901 TGGGGAAGCTAAGTGCAGAGTATGCAGAAACTATTATTTTTGTAAGTTTTCTCTAAGTAT 960
961 AAATAAATTTCAAAATAAAAATAAAAACTTAGTAAAGAACTATAATGCAATTCTATGTAA 1020
1021 GCCAAACATAATATGTCTTCCAGTTTGAAACCTCTGGGTTTTATTTTATTTTATTTTATT 1080
1081 TTTGAGACAGAGTCTTGCTGTGTCACCCAGGCTGGAGTGTAGTGGCACTATTTCGGCCCA 1140
1141 CTGCAACCTCCACCTCCCAGGCTCAAATGATTCTCCTGCCTCAGCCTCCGGAGTAGCTGG 1200
1201 GATTACAGGCGCGTACCACCACACCCAGCTAATTTTGTATTTTTAGTAGAGATGGGGTT 1260
1261 TCACCATTTTGGCCAGGCTGGTTTTGAACTCCTGACCTCAAGTGATCCACTTGTCTTGGC 1320
1321 CTCCCAAAATGCTGGGATTACAGGCGTGAGCCACTGCACCAGGCAGAGGCCTCTGTTTTT 1380
1381 TATCTCTTTTTGGCCTCTACAGTGCCTAGTAAAGCACCTGATACATGGTAAACGATCAGT 1440
1441 AATTACTAGTACTCTATTTTGGAGAAAATGATTTTTTAAAAAGTCATTGTGTTCCATCCA 1500
1501 TGAGTCGTTTGAGTTTTAAAACTGTCTTTTTGTTTGTTTTTGAACAGGTTTACAAAGGAG 1560
1561 GAAAACGACTTCTTCTAGATTTTTTTTTCAGTTTCTTCTATAAATCAAAACATCTCAAAA 1620
1621 TGGAGACCTAAAATCCTTAAAGGGACTTAGTCTAATCTCGGGAGGTAGTTTTGTGCATGG 1680
1681 GTAAACAAATTAAGTATTAACTGGTGTTTTACTATCCAAAGAATGCTAATTTTATAAACA 1740
1741 TGATCGAGTTATATAAGGTATACCATAATGAGTTTGATTTTGAATTTGATTTGTGGAAAT 1800
1801 AAAGGAAAAGTGATTCTAGCTGGGGCATATTGTTAAAGCATTTTTTTCAGAGTTGGCCAG 1860
1861 GCAGTCTCCTACTGGCACATTCTCCCATTATGTAGAATAGAAATAGTACCTGTGTTTGGG 1920
1921 AAAGATTTTAAAATGAGTGACAGTTATTTGGAACAAAGAGCTAATAATCAATCCACTGCA 1980
1981 AATTAAAGAAACATGCAGATGAAAGTTTTGACACATTAAAATACTTCTACAGTGACAAAG 2040
2041 AAAAATCAAGAACAAAGCTTTTTGATATGTGCAACAAATTTAGAGGAAGTAAAAAGATAA 2100
2101 ATGTGATGATTGGTCAAGAAATTATCCAGTTATTTACAAGGCCACTGATATTTTAAACGT 2160
2161 CCAAAAGTTTGTTTAAATGGGCTGTTACCGCTGAGAATGATGAGGATGAGAATGATGGTT 2220
2221 GAAGGTTACATTTTAGGAAATGAAGAAACTTAGAAAATTAATATAAAGACAGTTGATGAAT 2280
2281 ACAAAGAAGATTTTTATAACAATGTGTAAAATTTTTGGCCAGGGAAAGGAATATTGAAGT 2340
2341 TAGATACAATTACTTACCTTTGAGGGAAATAATTGTTGGTAATGAGATGTGATGTTTCTC 2400
2401 CTGCCACCTGGAAACAAAGCATTGAAGTCTGCAGTTGAAAAGCCCAACGTCTGTGAGATC 2460
2461 CAGGAAACCATGCTTGCAAACCACTGGTAAAAAAAAAAAAAAAAAAAAAAAGCCACAG 2520
2521 TGACTTGCTTATTGGTCATTGCTAGTATTATCGACTCAGAACCTCTTTACTAATGGCTAG 2580
2581 TAAATCATAATTGAGAAATTCTGAATTTTGACAAGGTCTCTGCTGTTGAAATGGTAAATT 2640
2641 TATTATTTTTTTTGTCATGATAAATTCTGGTTCAAGGTATGCTATCCATGAAATAATTTC 2700
2701 TGACCAAAACTAAATTGATGCAATTTGATTATCCATCTTAGCCTACAGATGGCATCTGGT 2760
2761 AACTTTTGACTGTTTTAAAAAATAAATCCACTATCAGAGTAGATTTGATGTTGGCTTCAG 2820
2821 AAACATTTAGAAAAACAAAAGTTCAAAAATGTTTTCAGGAGGTGATAAGTTGAATAACTC 2880
2881 TACAATGTTAGTTCTTTGAGGGGACARAAATTTAAAATCTTTGAAAGGTCTTATTTTA 2940
2941 CAGCCATATCTAAATTATCTTAAGAAAATTTTTAACAAAGGGAATGAAATATATCATG 3000
3001 ATTCTGTTTTTCCAAAAGTAACCTGAATATAGCAATGAAGTTCAGTTTTGTTATTGGTAG 3060
3061 TTTGGGCAGAGTCTCTTTTTGCAGCACCTGTTGTCTACCATAATTACAGAGGACATTTCC 3120
3121 ATGTTCTAGCCAAGTATACTATTAGAATAAARAAACTTAACATTGAGTTGCTTCAACAGC 3180

```
3181 ATGAAACTGAGTCCAAAAGACCAAATGAACAAACACATTAATCTCTGATTATTTATTTTA 3240
3241 AATAGAATATTTAATTGTGTAAGATCTAATAGTATCATTATACTTAAGCAATCATATTCC 3300
3301 TGATGATCTATGGGAAATAACTATTATTTAATTAATATTGAAACCAGGTTTTAAGATGTG 3360
3361 TTAGCCAGTCCTGTTACTAGTAAATCTCTTTATTTGGAGAGAAATTTTAGATTGTTTTGT 3420
3421 TCTCCTTATTAGAAGGATTGTAGAAAGAAAAAAATGACTAATTGGAGAAAAATTGGGGAT 3480
3481 ATATCATATTTCACTGAATTCAAAATGTCTTCAGTTGTAAATCTTACCATTATTTTACGT 3540
3541 ACCTCTAAGAAATAAAAGTGCTTCTAATTAAAATATGATGTCATTAATTATGAAATACTT 3600
3601 CTTGATAACAGAAGTTTTAAAATAGCCATCTTAGAATCAGTGAAATATGGTAATGTATTA 3660
3661 TTTTCCTCCTTTGAGTNAGGTCTTGTGCTTTTTNTTCCTGGCCACTAAATNTCACCATNT 3720
3721 CCAANAAGCAAANTAAACCTATTCTGAATATTTTTGCTGTGAAACACTTGNCAGCAGAGC 3780
3781 TTTCCCNCCATGNNAGAAGCTTCATGAGTCACACATTACATCTTTGGGTTGATTGAATGC 3840
3841 CACTGAAACATTTCTAGTAGCCTGGAGNAGTTGACCTACCTGTGGAGATGCCTGCCATTA 3900
3901 AATGGCATCCTGATGGCTTAATACACATCACTCTTCTGTGNAGGGTTTTAATTTTCAACA 3960
3961 CAGCTTACTCTGTAGCATCATGTTTACATTGTATGTATAAAGATTATACNAAGGTGCAAT 4020
4021 TGTGTATTTCTTCCTTAAAATGTATCAGTATAGGATTTAGAATCTCCATGTTGAAACTCT 4080
4081 AAATGCATAGAAATAAAAATAATAAAAAATTTTTCATTTTGGCTTTTCAGCCTAGTATTA 4140
4141 AAACTGATAAAAGCAAAGCCATGCACAAAACTACCTCCCTAGAGAAAGGCTAGTCCCTTT 4200
4201 TCTTCCCCATTCATTTCATTATGAACATAGTAGAAAACAGCATATTCTTATCAAATTTGA 4260
SEQ.ID 6-1             M  N  I  V  E  N  S  I  F  L  S  N  L  M  14

4261 TGAAAAGCGCCAACACGTTTGAACTGAAATACGACTTGTCATGTGAACTGTACCGAATGT 4320
  15  K  S  A  N  T  F  E  L  K  Y  D  L  S  C  E  L  Y  R  M  S 34

4321 CTACGTATTCCACTTTTCCTGCTGGGGTTCCTGTCTCAGAAAGGAGTCTTGCTCGTGCTG 4380
  35  T  Y  S  T  F  P  A  G  V  P  V  S  E  R  S  L  A  R  A  G 54

4381 GTTTCTATTACACTGGTGTGAATGACAAGGTCAAATGCTTCTGTTGTGGCCTGATGCTGG 4440
  55  F  Y  Y  T  G  V  N  D  K  V  K  C  F  C  C  G  L  M  L  D 74

4441 ATAACTGGAAAAGAGGAGACAGTCCTACTGAAAAGCATAAAAAGTTGTATCCTAGCTGCA 4500
  75  N  W  K  R  G  D  S  P  T  E  K  H  K  K  L  Y  P  S  C  R 94

4501 GATTCGTTCAGAGTCTAAATTCCGTTAACAACTTGGAAGCTACCTCTCAGCCTACTTTTC 4560
  95  F  V  Q  S  L  N  S  V  N  N  L  E  A  T  S  Q  P  T  F  P 114

4561 CTTCTTCAGTAACACATTCCACACACTCATTACTTCCGGGTACAGAAAACAGTGGATATT 4620
 115  S  S  V  T  H  S  T  H  S  L  L  P  G  T  E  N  S  G  Y  F 134

4621 TCCGTGGCTCTTATTCAAACTCTCCATCAAATCCTGTAAACTCCAGAGCAAATCAAGAAT 4680
 135  R  G  S  Y  S  N  S  P  S  N  P  V  N  S  R  A  N  Q  E  F 154

4681 TTTCTGCCTTGATGAGAAGTTCCTACCCCTGTCCAATGAATAACGAAAATGCCAGATTAC 4740
 155  S  A  L  M  R  S  S  Y  P  C  P  M  N  N  E  N  A  R  L  L 174

4741 TTACTTTTCAGACATGGCCATTGACTTTTCTGTCGCCAACAGATCTGGCACGAGCAGGCT 4800
 175  T  F  Q  T  W  P  L  T  F  L  S  P  T  D  L  A  R  A  G  F 194

4801 TTTACTACATAGGACCTGGAGACAGAGTGGCTTGCTTTGCCTGTGGTGGAAAATTGAGCA 4860
 195  Y  Y  I  G  P  G  D  R  V  A  C  F  A  C  G  G  K  L  S  N 214

4861 ATTGGGAACCGAAGGATAATGCTATGTCAGAACACCTGAGACATTTTCCCAAATGCCCAT 4920
 215  W  E  P  K  D  N  A  M  S  E  H  L  R  H  F  P  K  C  P  F 234
```

```
4921 TTATAGAAAATCAGCTTCAAGACACTTCAAGATACACAGTTTCTAATCTGAGCATGCAGA 4980
 235   I  E  N  Q  L  Q  D  T  S  R  Y  T  V  S  N  L  S  M  Q  T  254

4981 CACATGCAGCCCGCTTTAAAACATTCTTTAACTGGCCCTCTAGTGTTCTAGTTAATCCTG 5040
 255   H  A  A  R  F  K  T  F  F  N  W  P  S  S  V  L  V  N  P  E  274
                                         1 2
5041 AGCAGCTTGCAAGTGCGGGTTTTTATTATGTGGGTAACAGTGATGATGTCAAATGCTTTT 5100
 275   Q  L  A  S  A  G  F  Y  Y  V  G  N  S  D  D  V  K  C  F  C  294

5101 GCTGTGATGGTGGACTCAGGTGTTGGGAATCTGGAGATGATCCATGGGTTCAACATGCCA 5160
 295   C  D  G  G  L  R  C  W  E  S  G  D  D  P  W  V  Q  H  A  K  314
                  2 3
5161 AGTGGTTTCCAAGGTGTGAGTACTTGATAAGAATTAAAGGACAGGAGTTCATCCGTCAAG 5220
 315   W  F  P  R  C  E  Y  L  I  R  I  K  G  Q  E  F  I  R  Q  V  334
                              3 4
5221 TTCAAGCCAGTTACCCTCATCTACTTGAACAGCTGCTATCCACATCAGACAGCCCAGGAG 5280
 335   Q  A  S  Y  P  H  L  L  E  Q  L  L  S  T  S  D  S  P  G  D  354
                         4 5
5281 ATGAAAATGCAGAGTCATCAATTATCCATTTTGAACCTGGAGAAGACCATTCAGAAGATG 5340
 355   E  N  A  E  S  S  I  I  H  F  E  P  G  E  D  H  S  E  D  A  374

5341 CAATCATGATGAATACTCCTGTGATTAATGCTGCCGTGGAAATGGGCTTTAGTAGAAGCC 5400
 375   I  M  M  N  T  P  V  I  N  A  A  V  E  M  G  F  S  R  S  L  394

5401 TGGTAAAACAGACAGTTCAGAGAAAAATCCTAGCAACTGGAGAGAATTATAGACTAGTCA 5460
 395   V  K  Q  T  V  Q  R  K  I  L  A  T  G  E  N  Y  R  L  V  N  414

5461 ATGATCTTGTGTTAGACTTACTCAATGCAGAAGATGAAATAAGGGAAGAGGAGAGAGAAA 5520
 415   D  L  V  L  D  L  L  N  A  E  D  E  I  R  E  E  E  R  E  R  434
                                 5 6
5521 GAGCAACTGAGGAAAAAGAATCAAATGATTTATTATTAATCCGGAAGAATAGAATGGCAC 5580
 435   A  T  E  E  K  E  S  N  D  L  L  L  I  R  K  N  R  M  A  L  454

5581 TTTTTTCAACATTTGACTTGTGTAATTCCAATCCTGGATAGTCTACTAACTGCCGGAATTA 5640
 455   F  Q  H  L  T  C  V  I  P  I  L  D  S  L  L  T  A  G  I  I  474

5641 TTAATGAACAAGAACATGATGTTATTAAACAGAAGACACAGACGTCTTTACAAGCAAGAG 5700
 475   N  E  Q  E  H  D  V  I  K  Q  K  T  Q  T  S  L  Q  A  R  E  494

5701 AACTGATTGATACGATTTTAGTAAAAGGAAATATTGCAGCCACTGTATTCAGAAACTCTC 5760
 495   L  I  D  T  I  L  V  K  G  N  I  A  A  T  V  F  R  N  S  L  514
                                                         6 7
5761 TGCAAGAAGCTGAAGCTGTGTTATATGAGCATTTATTTGTGCAACAGGACATAAAATATA 5820
 515   Q  E  A  E  A  V  L  Y  E  H  L  F  V  Q  Q  D  I  K  Y  I  534
                        7 8
5821 TTCCCACAGAAGATGTTTCAGATCTACCAGTGGAAGAACAATTGCGGAGACTACAAGAAG 5880
 535   P  T  E  D  V  S  D  L  P  V  E  E  Q  L  R  R  L  Q  E  E  554

5881 AAAGAACATGTAAAGTGTGTATGGACAAAGAAGTGTCCATAGTGTTTATTCCTTGTGGTC 5940
 555   R  T  C  K  V  C  M  D  K  E  V  S  I  V  F  I  P  C  G  H  574

5941 ATCTAGTAGTATGCAAAGATTGTGCTCCTTCTTTAAGAAAGTGTCCTATTTGTAGGAGTA 6000
 575   L  V  V  C  K  D  C  A  P  S  L  R  K  C  P  I  C  R  S  T  594
```

```
6001 CAATCAAGGGTACAGTTCGTACATTTCTTTCATGAAGAAGAACCAAAACATCGTCTAAAC 6060
 595   I  K  G  T  V  R  T  F  L  S  *                            604

6061 TTTAGAATTAATTTATTAAATGTATTATAACTTTAACTTTTATCCTAATTTGGTTTCCTT 6120
6121 AAAATTTTTATTTATTTACAACTCAAAAAACATTGTTTTGTGTAACATATTTATATATGT 6180
6181 ATCTAAACCATATGAACATATATTTTTTAGAAACTAAGAGAATGATAGGCTTTTGTTCTT 6240
6241 ATGAACGAAAAAGAGGTAGCACTACAAACACAATATTCAATCAAAATTTCAGCATTATTG 6300
6301 AAATTGTAAGTGAAGTAAAACTTAAGATATTTGAGTTAACCTTTAAGAATTTTAAATATT 6360
6361 TTGGCATTGTACTAATACCGGGAACATGAAGCCAGGTGTGGTGGTATGTGCCTGTAGTCC 6420
6421 CAGGCTGAGGCAAGAGAATTACTTGAGCCCAGGAGTTTGAATCCATCCTGGGCAGCATAC 6480
6481 TGAGACCCTGCCTTTAAAAACAAACAGAACAAAAACAAAACACCAGGGACACATTTCTCT 6540
6541 GTCTTTTTTGATCAGTGTCCTATACATCGAAGGTGTGCATATATGTTGAATCACATTTTA 6600
6601 GGGACATGGTGTTTTTATAAAGAATTCTGTGAGAAAAATTTAATAAAGCAACCAAAAAA 6660
6661 AAAAAAAA 6669
```

```
                1 2
SEQ.ID 7 - 1  GAGCGCCCGGGCTGATCCGAGCCGAGCGGGCCGTATCTCCTTGTCGGCGCCGCTGATTCC  60
         61   CGGCTCTGCGGAGGCCTCTAGGCAGCCGCGCAGCTTCCGTGTTTGCTGCGCCCGCACTGC 120
                2 3
        121   GATTTACAACCCTGAAGAATCTCCCTATCCCTATTTTGTCCCCCTGCAGTAATAAATCCC 180
        181   ATTATGGAGATCTCGAAACTTTATAAAGGGATATAGTTTGAATTCTATGGAGTGTAATTT 240
        241   TGTGTATGAATTATATTTTTAAAACATTGAAGAGTTTTCAGAAAGAAGGCTAGTAGAGTT 300
        301   GATTACTGATACTTTATGCTAAGCAGTACTTTTTTGGTAGTACAATATTTTGTTAGGCGT 360
        361   TTCTGATAACACTAGAAAGGACAAGTTTTATCTTGTGATAAATTGATTAATGTTTACAAC 420
        421   ATGACTGATAATTATAGCTGAATAGTCCTTAAATGATGAACAGGTTATTTAGTTTTTAAA 480
        481   TGCAGTGTAAAAAGTGTGCTGTGGAAATTTTATGGCTAACTAAGTTTATGGAGAAAATAC 540
        541   CTTCAGTTGATCAAGAATAATAGTGGTATACAAAGTTAGGAAGAAAGTCAACATGATGCT 600
        601   GCAGGAAATGGAAACAAATACAAATGATATTTAACAAAGATAGAGTTTACAGTTTTTGAA 660
        661   CTTTAAGCCAAATTCATTTGACATCAAGCACTATAGCAGGCACAGGTTCAACAAAGCTTG 720
        721   TGGGTATTGACTTCCCCCAAAAGTTGTCAGCTGAAGTAATTTAGCCCACTTAAGTAAATA 780
        781   CTATGATGATAAGCTGTGTGAACTTAGCTTTTAAATAGTGTGACCATATGAAGGTTTTAA 840
        841   TTACTTTTGTTTATTGGAATAAAATGAGATTTTTTGGGTTGTCATGTTAAAGTGCTTATA 900
        901   GGGAAAGAAGCCTGCATATAATTTTTTACCTTGTGGCATAATCAGTAATTGGTCTGTTAT 960
        961   TCAGGCTTCATAGCTTGTAACCARATATAAATAAAAGGCATAATTTAGGTATTCTATAGT 1020
       1021   TGCTTAGAATTTTGTTAATATAAATCTCTGTGAAAAATCAAGGAGTTTTAATATTTTCAG 1080
       1081   AAGTGCATCCACCTTTCAGGGCTTTAAGTTAGTATTAACTCAAGATTATGAACAAATAGC 1140
       1141   ACTTAGGTTACCTGAAAGAGTTACTACAACCCCAAAGAGTTGTGTTCTAAGTAGTATCTT 1200
       1201   GGTAATTCAGAGAGATACTCATCCTACCTGAATATAAACTGAGATAAATCCAGTAAAGAA 1260
       1261   AGTGTAGTAAATTCTACATAAGAGTCTATCATTGATTTCTTTTTGTGGTAAAAATCTTAG 1320
       1321   TTCATGTGAAGAAATTTCATGTGAATGTTTTAGCTATCAAACAGTACTGTCACCTACTCA 1380
                                                                          M 1
       1381   TGCACAAAACTGCCTCCCAAAGACTTTTCCCAGGTCCCTCGTATCAAAACATTAAGAGTA 1440
SEQ.ID 8 -2     H  K  T  A  S  Q  R  L  F  P  G  P  S  Y  Q  N  I  K  S  I 21
       1441   TAATGGAAGATAGCACGATCTTGTCAGATTGGACAAACAGCAACAAACAAAAAATGAAGT 1500
         22     M  E  D  S  T  I  L  S  D  W  T  N  S  N  K  Q  K  M  K  Y 41
       1501   ATGACTTTTCCTGTGAACTCTACAGAATGTCTACATATTCAACTTTCCCCGCCGGGGTGC 1560
         42     D  F  S  C  E  L  Y  R  M  S  T  Y  S  T  F  P  A  G  V  P 61
       1561   CTGTCTCAGAAAGGAGTCTTGCTCGTGCTGGTTTTTATTATACTGGTGTGAATGACAAGG 1620
         62     V  S  E  R  S  L  A  R  A  G  F  Y  Y  T  G  V  N  D  K  V 81
       1621   TCAAATGCTTCTGTTGTGGCCTGATGCTGGATAACTGGAAACTAGGAGACAGTCCTATTC 1680
         82     K  C  F  C  C  G  L  M  L  D  N  W  K  L  G  D  S  P  I  Q 101
       1681   AAAAGCATAAACAGCTATATCCTAGCTGTAGCTTTATTCAGAATCTGGTTTCAGCTAGTC 1740
        102     K  H  K  Q  L  Y  P  S  C  S  F  I  Q  N  L  V  S  A  S  L 121
       1741   TGGGATCCACCTCTAAGAATACGTCTCCAATGAGAAACAGTTTTGCACATTCATTATCTC 1800
        122     G  S  T  S  K  N  T  S  P  M  R  N  S  F  A  H  S  L  S  P 141
       1801   CCACCTTGGAACATAGTAGCTTGTTCAGTGGTTCTTACTCCAGCCTTTCTCCAAACCCTC 1860
        142     T  L  E  H  S  S  L  F  S  G  S  Y  S  S  L  S  P  N  P  L 161
       1861   TTAATTCTAGAGCAGTTGAAGACATCTCTTCATCGAGGACTAACCCCTACAGTTATGCAA 1920
        162     N  S  R  A  V  E  D  I  S  S  S  R  T  N  P  Y  S  Y  A  M 181
       1921   TGAGTACTGAAGAAGCCAGATTTCTTACCTACCATATGTGGCCATTAACTTTTTTGTCAC 1980
        182     S  T  E  E  A  R  F  L  T  Y  H  M  W  P  L  T  F  L  S  P 201
```

```
1981 CATCAGAATTGGCAAGAGCTGGTTTTTATTATATAGGACCTGGAGATAGGGTAGCCTGCT 2040
 202   S  E  L  A  R  A  G  F  Y  Y  I  G  P  G  D  R  V  A  C  F 221

2041 TTGCCTGTGGTGGGAAGCTCAGTAACTGGGAACCAAAGGATGATGCTATGTCAGAACACC 2100
 222   A  C  G  G  K  L  S  N  W  E  P  K  D  D  A  M  S  E  H  R 241

2101 GGAGGCATTTTCCCAACTGTCCATTTTTGGAAAATTCTCTAGAAACTCTGAGGTTTAGCA 2160
 242   R  H  F  P  N  C  P  F  L  E  N  S  L  E  T  L  R  F  S  I 261

2161 TTTCAAATCTGAGCATGCAGACACATGCAGCTCGAATGAGAACATTTATGTACTGGCCAT 2220
 262   S  N  L  S  M  Q  T  H  A  A  R  M  R  T  F  M  Y  W  P  S 281
                                                          3 4
2221 CTAGTGTTCCAGTTCAGCCTGAGCAGCTTGCAAGTGCTGGTTTTTATTATGTGGGTCGCA 2280
 282   S  V  P  V  Q  P  E  Q  L  A  S  A  G  F  Y  Y  V  G  R  N 301

2281 ATGATGATGTCAAATGCTTTTGTTGTGATGGTGGCTTGAGGTGTTGGGAATCTGGAGATG 2340
 302   D  D  V  K  C  F  C  C  D  G  G  L  R  C  W  E  S  G  D  D 321
                                  4 5
2341 ATCCATGGGTAGAACATGCCAAGTGGTTTCCAAGGTGTGAGTTCTTGATACGAATGAAAG 2400
 322   P  W  V  E  H  A  K  W  F  P  R  C  E  F  L  I  R  M  K  G 341
                                                       5 6
2401 GCCAAGAGTTTGTTGATGAGATTCAAGGTAGATATCCTCATCTTCTTGAACAGCTGTTGT 2460
 342   Q  E  F  V  D  E  I  Q  G  R  Y  P  H  L  L  E  Q  L  L  S 361
                                          6 7
2461 CAACTTCAGATACCACTGGAGAAGAAAATGCTGACCCACCAATTATTCATTTTGGACCTG 2520
 362   T  S  D  T  T  G  E  E  N  A  D  P  P  I  I  H  F  G  P  G 381

2521 GAGAAAGTTCTTCAGAAGATGCTGTCATGATGAATACACCTGTGGTTAAATCTGCCTTGG 2580
 382   E  S  S  S  E  D  A  V  M  M  N  T  P  V  V  K  S  A  L  E 401

2581 AAATGGGCTTTAATAGAGACCTGGTGAAACAAACAGTTCAAAGTAAAATCCTGACAACTG 2640
 402   M  G  F  N  R  D  L  V  K  Q  T  V  Q  S  K  I  L  T  T  G 421

2641 GAGAGAACTATAAAACAGTTAATGATATTGTGTCAGCACTTCTTAATGCTGAAGATGAAA 2700
 422   E  N  Y  K  T  V  N  D  I  V  S  A  L  L  N  A  E  D  E  K 441
                                            7 8
2701 AAAGAGAAGAGGAGAAGGAAAAAACAAGCTGAAGAAATGGCATCAGATGATTTGTCATTAA 2760
 442   R  E  E  E  K  E  K  Q  A  E  E  M  A  S  D  D  L  S  L  I 461

2761 TTCGGAAGAACAGAATGGCTCTCTTTCAACAATTGACATGTGTGCTTCCTATCCTGGATA 2820
 462   R  K  N  R  M  A  L  F  Q  Q  L  T  C  V  L  P  I  L  D  N 481

2821 ATCTTTTAAAGGCCAATGTAATTAATAAACAGGAACATGATATTATTAAACAAAAAACAC 2880
 482   L  L  K  A  N  V  I  N  K  Q  E  H  D  I  I  K  Q  K  T  Q 501

2881 AGATACCTTTACAAGCGAGAGAACTGATTGATACCATTTTGGTTAAAGGAAATGCTGCGG 2940
 502   I  P  L  Q  A  R  E  L  I  D  T  I  L  V  K  G  N  A  A  521

2941 CCAACATCTTCAAAAACTGTCTAAAAGAAATTGACTCTACATTGTATAAGAACTTATTTG 3000
 522   N  I  F  K  N  C  L  K  E  I  D  S  T  L  Y  K  N  L  F  V 541
      8 9                                              9 10
3001 TGGATAAGAATATGAAGTATATCCCAACAGAAGATGTTTCAGGTCTGTCACTGGAAGAAC 3060
 542   D  K  N  M  K  Y  I  P  T  E  D  V  S  G  L  S  L  E  E  Q 561
```

```
3061 AATTGAGGAGGTTGCAAGAAGAACGAACTTGTAAAGTGTGTATGGACAAAGAAGTTTCTG 3120
 562    L  R  R  L  Q  E  E  R  T  C  K  V  C  M  D  K  E  V  S  V 581

3121 TTGTATTTATTCCTTGTGGTCATCTGGTAGTATGCCAGGAATGTGCCCCTTCTCTAAGAA 3180
 582    V  F  I  P  C  G  H  L  V  V  C  Q  E  C  A  P  S  L  R  K 601

3181 AATGCCCTATTTGCAGGGGTATAATCAAGGGTACTGTTCGTACATTTCTCTCTTAAAGAA 3240
 602    C  P  I  C  R  G  I  I  K  G  T  V  R  T  F  L  S  *      618

3241 AAATAGTCTATATTTTAACCTGCATAAAAAGGTCTTTAAAATATTGTTGAACACTTGAAG 3300
3301 CCATCTAAAGTAAAAAGGGAATTATGAGTTTTTCAATTAGTAACATTCATGTTCTAGTCT 3360
3361 GCTTTGGTACTAATAATCTTGTTTCTGAAAAGATGGTATCATATATTTAATCTTAATCTG 3420
3421 TTTATTTACAAGGGAAGATTTATGTTTGGTGAACTATATTAGTATGTATGTGTACCTAAG 3480
3481 GGAGTAGTGTCACTGCTTGTTATGCATCATTTCAGGAGTTACTGGATTTGTTGTTCTTTC 3540
3541 AGAAAGCTTTGAATACTAAATTATAGTGTAGAAAAGAACTGGAAACCAGGAACTCTGGAG 3600
3601 TTCATCAGAGTTATGGTGCCGAATTGTCTTTGGTGCTTTTCACTTGTGTTTTAAAATAAG 3660
3661 GATTTTTCTCTTATTTCTCCCCCTAGTTTGTGAGAAACATCTCAATAAAGTGCTTTAAAA 3720
3721 AGAAAAAAAAAA 3732
```

```
SEQ.ID 9-1   ATTTTTTAAATTGATGCATTAACATTCTAAACATTCATCTGTTTTTAAATAGTAAAAATT  60
         61  GAACTTTGCCTTGAATATGTAATGATTCATTATAACAATTATGCATAGTCTTTAATAATC 120
        121  TGCATATTTTATGCTGCTTTCATGTTTTTCCTAATTAATGACTTCACATGTTTAATATTT 180
        181  ATAATTTTCTGTCATAGTTTCCATATTTATATAAAATGAATACTTAAGATCAGTAATTC  240
        241  TGCTCTGTTTGTTTATATACTATTTTCCATCAAAAGACAAAATGGGACTGAGGTTGAGGC 300
        301  TCGTTGCTAAAGCACTTTCCTAAAATGCAAAAGGCCCTATGATGGATCCCTAGTACTTAT 360
        361  TTAAGTGAGAGAGAAACAGGCTGGGGGTGTAGGTCTGTTAGAGCATGTGTTTGGCATTAT  420
        421  GTGAAGCCCAAACACTAAAAAAGGAGAACAAACAAAAGCGCAGACTTTAAAACTCAAGTG 480
        481  GTTTGGTAATGTACGACTCTACTGTTTAGAATTAAAATGTGTCTTAGTTATTGTGCCATT 540
        541  ATTTTTATGTCATCACTGGATAATATATTAGTGCTTAGTATCAGAAATAGTCCTTATGCT 600
        601  TTGTGTTTTGAAGTTCCTAATGCAATGTTCTCTTTCTAGAAAAGGTGGACAAGTCCTATT 660
        661  TTCCAGAGAAGATGACTTTTAACAGTTTTGAAGGAACTAGAACTTTTGTACTTGCAGACA 720
SEQ.ID 10-1              M  T  F  N  S  F  E  G  T  R  T  F  V  L  A  D  T  17

721  CCAATAAGGATGAAGAATTTGTAGAAGAGTTTAATAGATTAAAAACATTTGCTAACTTCC 780
         18    N  K  D  E  E  F  V  E  E  F  N  R  L  K  T  F  A  N  F  P  37

781  CAAGTAGTAGTCCTGTTTCAGCATCAACATTGGCGCGAGCTGGGTTTCTTTATACCGGTG 840
         38    S  S  S  P  V  S  A  S  T  L  A  R  A  G  F  L  Y  T  G  E  57

841  AAGGAGACACCGTGCAATGTTTCAGTTGTCATGCGGCAATAGATAGATGGCAGTATGGAG 900
         58    G  D  T  V  Q  C  F  S  C  H  A  A  I  D  R  W  Q  Y  G  D 77

901  ACTCAGCTGTTGGAAGACACAGGAGAATATCCCCAAATTGCAGATTTATCAATGGTTTTT 960
         78    S  A  V  G  R  H  R  R  I  S  P  N  C  R  F  I  N  G  F  Y 97

961  ATTTTGAAAATGGTGCTGCACAGTCTACAAATCCTGGTATCCAAAATGGCCAGTACAAAT 1020
         98    F  E  N  G  A  A  Q  S  T  N  P  G  I  Q  N  G  Q  Y  K  S 117

1021  CTGAAAACTGTGTGGGAAATAGAAATCCTTTTGCCCCTGACAGGCCACCTGAGACTCATG 1080
        118    E  N  C  V  G  N  R  N  P  F  A  P  D  R  P  P  E  T  H  A 137

1081  CTGATTATCTCTTGAGAACTGGACAGGTTGTAGATATTTCAGACACCATATACCCGAGGA 1140
        138    D  Y  L  L  R  T  G  Q  V  V  D  I  S  D  T  I  Y  P  R  N 157

1141  ACCCTGCCATGTGTAGTGAAGAAGCCAGATTGAAGTCATTTCAGAACTGGCCGGACTATG 1200
        158    P  A  M  C  S  E  E  A  R  L  K  S  F  Q  N  W  P  D  Y  A 177

1201  CTCATTTAACCCCCAGAGAGTTAGCTAGTGCTGGCCTCTACTACACAGGGGCTGATGATC 1260
        178    H  L  T  P  R  E  L  A  S  A  G  L  Y  Y  T  G  A  D  D  Q 197

1261  AAGTGCAATGCTTTTGTTGTGGGGGAAAACTGAAAAATTGGGAACCCTGTGATCGTGCCT 1320
        198    V  Q  C  F  C  C  G  G  K  L  K  N  W  E  P  C  D  R  A  W 217

1321  GGTCAGAACACAGGAGACACTTTCCCAATTGCTTTTTTGTTTTGGGCCGGAACGTTAATG 1380
        218    S  E  H  R  R  H  F  P  N  C  F  F  V  L  G  R  N  V  N  V 237

1381  TTCGAAGTGAATCTGGTGTGAGTTCTGATAGGAATTTCCCAAATTCAACAAACTCTCCAA 1440
        238    R  S  E  S  G  V  S  S  D  R  N  F  P  N  S  T  N  S  P  R 257

1441  GAAATCCAGCCATGGCAGAATATGAAGCACGGATCGTTACTTTTGGAACATGGACATCCT 1500
        258    N  P  A  M  A  E  Y  E  A  R  I  V  T  F  G  T  W  T  S  S 277
```

```
                                              1 2
1501 CAGTTAACAAGGAGCAGCTTGCAAGAGCTGGATTTTATGCTTTAGGTGAAGGCGATAAAG 1560
 278  V  N  K  E  Q  L  A  R  A  G  F  Y  A  L  G  E  G  D  K  V 297

1561 TGAAGTGCTTCCACTGTGGAGGAGGGCTCACGGATTGGAAGCCAAGTGAAGACCCCTGGG 1620
 298  K  C  F  H  C  G  G  L  T  D  W  K  P  S  E  D  P  W  D 317
                             2 3
1621 ACCAGCATGCTAAGTGCTACCCAGGGTGCAAATACCTATTGGATGAGAAGGGGCAAGAAT 1680
 318  Q  H  A  K  C  Y  P  G  C  K  Y  L  L  D  E  K  G  Q  E  Y 337
                                                  3 4
1681 ATATAAATAATATTCATTTAACCCATCCACTTGAGGAATCTTTGGGAAGAACTGCTGAAA 1740
 338  I  N  N  I  H  L  T  H  P  L  E  E  S  L  G  R  T  A  E  K 357
                            4 5
1741 AAACACCACCGCTAACTAAAAAAATCGATGATACCATCTTCCAGAATCCTATGGTGCAAG 1800
 358  T  P  P  L  T  K  K  I  D  D  T  I  F  Q  N  P  M  V  Q  E 377

1801 AAGCTATACGAATGGGATTTAGCTTCAAGGACCTTAAGAAAACAATGGAAGAAAAAATCC 1860
 378  A  I  R  M  G  F  S  F  K  D  L  K  K  T  M  E  E  K  I  Q 397

1861 AAACATCCGGGAGCAGCTATCTATCACTTGAGGTCCTGATTGCAGATCTTGTGAGTGCTC 1920
 398  T  S  G  S  S  Y  L  S  L  E  V  L  I  A  D  L  V  S  A  Q 417
                                                5 6
1921 AGAAAGATAATACGGAGGATGAGTCAAGTCAAACTTCATTGCAGAAAGACATTAGTACTG 1980
 418  K  D  N  T  E  D  E  S  S  Q  T  S  L  Q  K  D  I  S  T  E 437

1981 AAGAGCAGCTAAGGCGCCTACAAGAGGAGAAGCTTTCCAAAATCTGTATGGATAGAAATA 2040
 438  E  Q  L  R  R  L  Q  E  E  K  L  S  K  I  C  M  D  R  N  I 457

2041 TTGCTATCGTTTTTTTTCCTTGTGGACATCTGGCCACTTGTAAACAGTGTGCAGAAGCAG 2100
 458  A  I  V  F  F  P  C  G  H  L  A  T  C  K  Q  C  A  E  A  V 477

2101 TTGACAAATGTCCCATGTGCTACACCGTCATTACGTTCAACCAAAAAATTTTTATGTCTT 2160
 478  D  K  C  P  M  C  Y  T  V  I  T  F  N  Q  K  I  F  M  S  * 496

2161 AGTGGGGCACCACATGTTATGTTCTTCTTGCTCTAATTGAATGTGTAATGGGAGCGAACT 2220
2221 TTAAGTAATCCTGCATTTGCATTCCATTAGCATCCTGCTGTTTCCAAATGGAGACCAATG 2280
2281 CTAACAGCACTGTTTCCGTCTAAACATTCAATTTCTGGATCTTTCGAGTTATCAGCTGTA 2340
2341 TCATTTAGCCAGTGTTTTACTCGATTGAAACCTTAGACAGAGAAGCATTTTATAGCTTTT 2400
2401 CACATGTATATTGGTAGTACACTGACTTGATTTCTATATGTAAGTGAATTCATCACCTGC 2460
2461 ATGTTTCATGCCTTTTGCATAAGCTTAACAAATGGAGTGTTCTGTATAAGCATGGAGATG 2520
2521 TGATGGAATCTGCCCAATGACTTTAATTGGCTTATTGTAAACACGGAAAGAACTGCCCCA 2580
2581 CGCTGCTGGGAGGATAAAGATTGTTTTAGATGCTCACTTCTGTGTTTTAGGATTCTGCCC 2640
2641 ATTTACTTGGAATTTATTGGAGTTATAATGTACTTATATGATATTTCCGAA 2691
```

```
SEQ.ID 11 - 1  TGGGAGTTCCCCGGAGCCCTGGAGGAAAGCACCGCAGGTCTGAGCAGCCCTGAGCCGGGC 60
          61  AGGGTGGGGGCAGTGGCTAAGGCCTAGCTGGGGACGATTTAAAGGTATCGCGCCACCCAG 120
         121  CCACACCCCACAGGCCAGGCGAGGGTGCCACCCCCGGAGATCAGAGGTCATTGCTGGCGT 180
         181  TCAGAGCCTAGGAAGTGGGCTGCGGTATCAGCCTAGCAGTAAAACCGACCAGAAGCCATG 240
         241  CACAAAACTACATCCCCAGAGAAAGACTTGTCCCTTCCCCTCCCTGTCATCTCACCATGA 300
         301  ACATGGTTCAAGACAGCGCCTTTCTAGCCAAGCTGATGAAGAGTGCTGACACCTTTGAGT 360
SEQ.ID 12 - 1   M   V   Q   D   S   A   F   L   A   K   L   M   K   S   A   D   T   F   E   L 20

361  TGAAGTATGACTTTTCCTGTGAGCTGTACCGATTGTCCACGTATTCAGCTTTTCCCAGGG 420
          21   K   Y   D   F   S   C   E   L   Y   R   L   S   T   Y   S   A   F   P   R   G 40

421  GAGTTCCTGTGTCAGAAAGGAGTCTGGCTCGTGCTGGCTTTTACTACACTGGTGCCAATG 480
          41   V   P   V   S   E   R   S   L   A   R   A   G   F   Y   Y   T   G   A   N   D 60

481  ACAAGGTCAAGTGCTTCTGCTGTGGCCTGATGCTAGACAACTGGAAACAAGGGGACAGTC 540
          61   K   V   K   C   F   C   C   G   L   M   L   D   N   W   K   Q   G   D   S   P 80

541  CCATGGAGAAGCACAGAAAGTTGTACCCCAGCTGCAACTTTGTACAGACTTTGAATCCAG 600
          81   M   E   K   H   R   K   L   Y   P   S   C   N   F   V   Q   T   L   N   P   A 100

601  CCAACAGTCTGGAAGCTAGTCCTCGGCCTTCTCTTCCTTCCACGGCGATGAGCACCATGC 660
         101   N   S   L   E   A   S   P   R   P   S   L   P   S   T   A   M   S   T   M   P 120

661  CTTTGAGCTTTGCAAGTTCTGAGAATACTGGCTATTTCAGTGGCTCTTACTCGAGCTTTC 720
         121   L   S   F   A   S   S   E   N   T   G   Y   F   S   G   S   Y   S   S   F   P 140

721  CCTCAGACCCTGTGAACTTCCGAGCAAATCAAGATTGTCCTGCTTTGAGCACAAGTCCCT 780
         141   S   D   P   V   N   F   R   A   N   Q   D   C   P   A   L   S   T   S   P   Y 160

781  ACCACTTTGCAATGAACACAGAGAAGGCCAGATTACTCACCTATGAAACATGGCCATTGT 840
         161   H   F   A   M   N   T   E   K   A   R   L   L   T   Y   E   T   W   P   L   S 180

841  CTTTTTCTGTCACCAGCAAAGCTGGCCAAAGCAGGCTTCTACTACATAGGACCTGGAGATA 900
         181   F   L   S   P   A   K   L   A   K   A   G   F   Y   Y   I   G   P   G   D   R 200

901  GAGTGGCCTGCTTTGCGTGCGATGGGAAACTGAGCAACTGGGAACGTAAGGATGATGCTA 960
         201   V   A   C   F   A   C   D   G   K   L   S   N   W   E   R   K   D   D   A   M 220

961  TGTCAGAGCACCAGAGGCATTTCCCCAGCTGTCCGTTCTTAAAAGACTTGGGTCAGTCTG 1020
         221   S   E   H   Q   R   H   F   P   S   C   P   F   L   K   D   L   G   Q   S   A 240

1021  CTTCGAGATACACTGTCTCTAACCTGAGCATGCAGACACACGCAGCCCGTATTAGAACAT 1080
         241   S   R   Y   T   V   S   N   L   S   M   Q   T   H   A   A   R   I   R   T   F 260

1081  TCTCTAACTGGCCTTCTAGTGCACTAGTTCATTCCCAGGAACTTGCAAGTGCGGGCTTTT 1140
         261   S   N   W   P   S   S   A   L   V   H   S   Q   E   L   A   S   A   G   F   Y 280

1141  ATTATACAGGACACAGTGATGATGTCAAGTGTTTTTGCTGTGATGGTGGGCTGAGGTGCT 1200
         281   Y   T   G   H   S   D   D   V   K   C   F   C   C   D   G   G   L   R   C   W 300

1201  GGGAATCTGGAGATGACCCCTGGGTGGAACATGCCAAGTGGTTTCCAAGGTGTGAGTACT 1260
         301   E   S   G   D   D   P   W   V   E   H   A   K   W   F   P   R   C   E   Y   L 320
```

```
1261 TGCTCAGAATCAAAGGCCAAGAATTTGTCAGCCAAGTTCAAGCTGGCTATCCTCATCTAC 1320
 321   L   R   I   K   G   Q   E   F   V   S   Q   V   Q   A   G   Y   P   H   L   L  340
              4 5                                                            5 6
1321 TTGAGCAGCTATTATCTACGTCAGACTCCCCAGAAGATGAGAATGCAGACGCAGCAATCG 1380
 341   E   Q   L   L   S   T   S   D   S   P   E   D   E   N   A   D   A   A   I   V  360

1381 TGCATTTTGGCCCTGGAGAAAGTTCGGAAGATGTCGTCATGATGAGCACGCCTGTGGTTA 1440
 361   H   F   G   P   G   E   S   S   E   D   V   V   M   M   S   T   P   V   V   K  380

1441 AAGCAGCCTTGGAAATGGGCTTCAGTAGGAGCCTGGTGAGACAGACGGTTCAGCGGCAGA 1500
 381   A   A   L   E   M   G   F   S   R   S   L   V   R   Q   T   V   Q   R   Q   I  400

1501 TCCTGGCCACTGGTGAGAACTACAGGACCGTCAGTGACCTCGTTATAGGCTTACTCGATG 1560
 401   L   A   T   G   E   N   Y   R   T   V   S   D   L   V   I   G   L   L   D   A  420
                                                                              6 7
1561 CAGAAGACGAGATGAGAGAGGAGCAGATGGAGCAGGCGGCCGAGGAGGAGGAGTCAGATG 1620
 421   E   D   E   M   R   E   E   Q   M   E   Q   A   A   E   E   E   E   S   D   D  440

1621 ATCTAGCACTAATCCGGAAGAACAAAATGGTGCTTTTCCAACATTTGACGTGTGTGACAC 1680
 441   L   A   L   I   R   K   N   K   M   V   L   F   Q   H   L   T   C   V   T   P  460

1681 CAATGCTGTATTGCCTCCTAAGTGCAAGGGCCATCACTGAACAGGAGTGCAATGCTGTGA 1740
 461   M   L   Y   C   L   L   S   A   R   A   I   T   E   Q   E   C   N   A   V   K  480

1741 AACAGAAACCACACACCTTACAAGCAAGCACACTGATTGATACTGTGTTAGCAAAAGGAA 1800
 481   Q   K   P   H   T   L   Q   A   S   T   L   I   D   T   V   L   A   K   G   N  500

1801 ACACTGCAGCAACCTCATTCAGAAACTCCCTTCGGGAAATTGACCCTGCGTTATACAGAG 1860
 501   T   A   A   T   S   F   R   N   S   L   R   E   I   D   P   A   L   Y   R   D  520
              7 8                                                        8 9
1861 ATATATTTGTGCAACAGGACATTAGGAGTCTTCCCACAGATGACATTGCAGCTCTACCAA 1920
 521   I   F   V   Q   Q   D   I   R   S   L   P   T   D   D   I   A   A   L   P   M  540

1921 TGGAAGAACAGTTGCGGAAACTCCAGGAGGAAAGAATGTGTAAAGTGTGTATGGACCGAG 1980
 541   E   E   Q   L   R   K   L   Q   E   E   R   M   C   K   V   C   M   D   R   E  560

1981 AGGTATCCATCGTGTTCATTCCCTGTGGCCATCTGGTCGTGTGCAAAGACTGCGCTCCCT 2040
 561   V   S   I   V   F   I   P   C   G   H   L   V   V   C   K   D   C   A   P   S  580

2041 CTCTGAGGAAGTGTCCCATCTGTAGAGGGACCATCAAGGGCACAGTGCGCACATTTCTCT 2100
 581   L   R   K   C   P   I   C   R   G   T   I   K   G   T   V   R   T   F   L   S  600

2101 CCTGAACAAGACTAATGGTCCATGGCTGCAACTTCAGCCAGGAGGAAGTTCACTGTCACT 2160
         *
2161 CCCAGCTCCATTCGGAACTTGAGGCCAGCCTGGATAGCACGAGACACCGCCAAACACACA 2220
2221 AATATAAACATGAAAAACTTTTGTCTGAAGTCAAGAATGAATGAATTACTTATATAATAA 2280
2281 TTTTAATTGGTTTCCTTAAAAGTGCTATTTGTTCCCAACTCAGAAAATTGTTTTCTGTAA 2340
2341 ACATATTTACATACTACCTGCATCTAAAGTATTCATATATTCATATATTCAGATGTCATG 2400
2401 AGAGAGGGTTTTGTTCTTGTTCCTGAAAAGCAGGGATTGCCTGCACTCCTGAAATTCTCA 2460
2461 GAAAGATTTACAATGTTGGCATTTATGGTTCAGAAACTAGAATCTTCTCCCGTTGCTTTA 2520
2521 AGAACCGGGAGCACAGATGTCCATGTGTTTTATGTATAGAAATTCCTGTTATTTATTGGA 2580
2581 TGACATTTTAGGGATATGAAATTTTTATAAAGAATTTGTGAGAAAAAGTTAATAAAGCAA 2640
2641 CATAATTACCTCTTTTTTTTTAAAGAAAAAAAAAAA 2676
```

SEQ.ID 13 -1    AGTTATATAAAATACGAAGTTTTCAAAAAGAAGGCTAGTGCAACAGAAAAGCTTTGCTAA 60
         61    AACAGATTCTTAGTTATTTGAGGTAACAAAAGAAAGCCATGTCTTGAATTGATTCGTTCT 120
        121    TAATTATAACAGACTTATAGTGGAAAGGGCCTTAAACACAGGCGGACTTTATAAAATGCA 180
        181    GTCTTAGGTTTATGTGCAAAATACTGTCTGTTGACCAGATGTATTCACATGATATATACA 240
        241    GAGTCAAGGTGGTGATATAGAAGATTTAACAGTGAGGGAGTTAACAGTCTGTGCTTTAAG 300
        301    CGCAGTTCCTTTACAGTGAATACTGTAGTCTTAATAGACCTGAGCTGACTGCTGCAGTTG 360
        361    ATGTAACCCACTTTAGAGAATACTGTATGACATCTTCTCTAAGGAAAACCAGCTGCAGAC 420
        421    TTCACTCAGTTCCTTTCATTTCATAGGAAAAGGAGTAGTTCAGATGTCATGTTTAAGTCC 480
        481    TTATAAGGGAAAAGAGCCTGAATATATGCCCTAGTACCTAGGCTTCATAACTAGTAATAA 540
        541    GAAGTTAGTTATGGGTAAATAGATCTCAGGTTACCCAGAAGAGTTCATGTGACCCCCAAA 600
        601    GAGTCCTAACTAGTGTCTTGGCAAGTGAGACAGATTTGTCCTGTGAGGGTGTCAATTCAC 660
        661    CAGTCCAAGCAGAAGACAATGAATCTATCCAGTCAGGTGTCTGTGGTGGAGATCTAGTGT 720
        721    CCAAGTGGTGAGAAACTTCATCTGGAAGTTTAAGCGGTCAGAAATACTATTACTACTCAT 780
          1                                                              M   1

781    GGACAAAACTGTCTCCCAGAGACTCGGCCAAGGTACCTTACACCAAAAACTTAAACGTAT 840
SEQ.ID 14 -2    D  K  T  V  S  Q  R  L  G  Q  G  T  L  H  Q  K  L  K  R  I  21

841    AATGGAGAAGAGCACAATCTTGTCAAATTGGACAAAGGAGAGCGAAGAAAAAATGAAGTT 900
          22    M  E  K  S  T  I  L  S  N  W  T  K  E  S  E  E  K  M  K  F  41

901    TGACTTTTCGTGTGAACTCTACCGAATGTCTACATATTCAGCTTTTCCCAGGGGAGTTCC 960
          42    D  F  S  C  E  L  Y  R  M  S  T  Y  S  A  F  P  R  G  V  P  61

961    TGTCTCAGAGAGGAGTCTGGCTCGTGCTGGCTTTTATTATACAGGTGTGAATGACAAAGT 1020
          62    V  S  E  R  S  L  A  R  A  G  F  Y  Y  T  G  V  N  D  K  V  81

1021    CAAGTGCTTCTGCTGTGGCCTGATGTTGGATAACTGGAAACAAGGGGACAGTCCTGTTGA 1080
          82    K  C  F  C  C  G  L  M  L  D  N  W  K  Q  G  D  S  P  V  E  101

1081    AAAGCACAGACAGTTCTATCCCAGCTGCAGCTTTGTACAGACTCTGCTTTCAGCCAGTCT 1140
         102    K  H  R  Q  F  Y  P  S  C  S  F  V  Q  T  L  L  S  A  S  L  121

1141    GCAGTCTCCATCTAAGAATATGTCTCCTGTGAAAAGTAGATTTGCACATTCGTCACCTCT 1200
         122    Q  S  P  S  K  N  M  S  P  V  K  S  R  F  A  H  S  S  P  L  141

1201    GGAACGAGGTGGCATTCACTCCAACCTGTGCTCTAGCCCTCTTAATTCTAGAGCAGTGGA 1260
         142    E  R  G  G  I  H  S  N  L  C  S  S  P  L  N  S  R  A  V  E  161

1261    AGACTTCTCATCAAGGATGGATCCCTGCAGCTATGCCATGAGTACAGAAGAGGCCAGATT 1320
         162    D  F  S  S  R  M  D  P  C  S  Y  A  M  S  T  E  E  A  R  F  181

1321    TCTTACTTACAGTATGTGGCCTTTAAGTTTTCTGTCACCAGCAGAGCTGGCCAGAGCTGG 1380
         182    L  T  Y  S  M  W  P  L  S  F  L  S  P  A  E  L  A  R  A  G  201

1381    CTTCTATTACATAGGGCCTGGAGACAGGGTGGCCTGTTTTGCCTGTGGTGGGAAACTGAG 1440
         202    F  Y  Y  I  G  P  G  D  R  V  A  C  F  A  C  G  G  K  L  S  221

1441    CAACTGGGAACCAAAGGATGATGCTATGTCAGAGCACCGCAGACATTTTCCCCACTGTCC 1500
         222    N  W  E  P  K  D  D  A  M  S  E  H  R  R  H  F  P  H  C  P  241

1501    ATTTCTGGAAAATACTTCAGAAACACAGAGGTTTAGTATATCAAATCTAAGTATGCAGAC 1560
         242    F  L  E  N  T  S  E  T  Q  R  F  S  I  S  N  L  S  M  Q  T  261

```
1561 ACACTCTGCTCGATTGAGGACATTTCTGTACTGGCCACCTAGTGTTCCTGTTCAGCCCGA 1620
 262  H  S  A  R  L  R  T  F  L  Y  W  P  P  S  V  P  V  Q  P  E  281

1621 GCAGCTTGCAAGTGCTGGATTCTATTACGTGGATCGCAATGATGATGTCAAGTGCTTTTG 1680
 282  Q  L  A  S  A  G  F  Y  Y  V  D  R  N  D  D  V  K  C  F  C  301

1681 TTGTGATGGTGGCTTGAGATGTTGGGAACCTGGAGATGACCCCTGGATAGAACACGCCAA 1740
 302  C  D  G  G  L  R  C  W  E  P  G  D  D  P  W  I  E  H  A  K  321
                1 2
1741 ATGGTTTCCAAGGTGTGAGTTCTTGATACGGATGAAGGGTCAGGAGTTTGTTGATGAGAT 1800
 322  W  F  P  R  C  E  F  L  I  R  M  K  G  Q  E  F  V  D  E  I  341
                         2 3
1801 TCAAGCTAGATATCCTCATCTTCTTGAGCAGCTGTTGTCCACTTCAGACACCCCAGGAGA 1860
 342  Q  A  R  Y  P  H  L  L  E  Q  L  S  T  S  D  T  P  G  E  361
                      3 4
1861 AGAAAATGCTGACCCTACAGAGACAGTGGTGCATTTTGGCCCTGGAGAAAGTTCGAAAGA 1920
 362  E  N  A  D  P  T  E  T  V  V  H  F  G  P  G  E  S  S  K  D  381

1921 TGTCGTCATGATGAGCACGCCTGTGGTTAAAGCAGCCTTGGAAATGGGCTTCAGTAGGAG 1980
 382  V  V  M  M  S  T  P  V  V  K  A  A  L  E  M  G  F  S  R  S  401

1981 CCTGGTGAGACAGACGGTTCAGCGGCAGATCCTGGCCACTGGTGAGAACTACAGGACCGT 2040
 402  L  V  R  Q  T  V  Q  R  Q  I  L  A  T  G  E  N  Y  R  T  V  421

2041 CAATGATATTGTCTCAGTACTTTTGAATGCTGAAGATGAGAGAAGAGAAGAGGAGAAGGA 2100
 422  N  D  I  V  S  V  L  L  N  A  E  D  E  R  R  E  E  E  K  E  441
                                  4 5
2101 AAGACAGACTGAAGAGATGGCATCAGGTGACTTATCACTGATTCGGAAGAATAGAATGGC 2160
 442  R  Q  T  E  E  M  A  S  G  D  L  S  L  I  R  K  N  R  M  A  461

2161 CCTCTTTCAACAGTTGACACATGTCCTTCCTATCCTGGATAATCTTCTTGAGGCCAGTGT 2220
 462  L  F  Q  Q  L  T  H  V  L  P  I  L  D  N  L  L  E  A  S  V  481

2221 AATTACAAAACAGGAACATGATATTATTAGACAGAAAACACAGATACCCTTACAAGCAAG 2280
 482  I  T  K  Q  E  H  D  I  I  R  Q  K  T  Q  I  P  L  Q  A  R  501

2281 AGAGCTTATTGACACCGTTTTAGTCAAGGGAAATGCTGCAGCCAACATCTTCAAAAACTC 2340
 502  E  L  I  D  T  V  L  V  K  G  N  A  A  A  N  I  F  K  N  S  521
                                                 5 6
2341 TCTGAAGGAAATTGACTCCACGTTATATGAAAACTTATTTGTGGAAAAGAATATGAAGTA 2400
 522  L  K  E  I  D  S  T  L  Y  E  N  L  F  V  E  K  N  M  K  Y  541
                           6 7
2401 TATTCCAACAGAAGACGTTTCAGGCTTGTCATTGGAAGAGCAGTTGCGGAGATTACAAGA 2460
 542  I  P  T  E  D  V  S  G  L  S  L  E  E  Q  L  R  R  L  Q  E  561

2461 AGAACGAACTTGCAAAGTGTGTATGGACAGAGAGGTTTCTATTGTGTTCATTCCGTGTGG 2520
 562  E  R  T  C  K  V  C  M  D  R  E  V  S  I  V  F  I  P  C  G  581

2521 TCATCTAGTAGTCTGCCAGGAATGTGCCCCTTCTCTAAGGAAGTGCCCCATCTGCAGGGG 2580
 582  H  L  V  V  C  Q  E  C  A  P  S  L  R  K  C  P  I  C  R  G  601

2581 GACAATCAAGGGGACTGTGCGCACATTTCTCTCATGAGTGAAGAATGGTCTGAAAGTATT 2640
 602  T  I  K  G  T  V  R  T  F  L  *                             612
```

```
2641 GTTGGACATCAGAAGCTGTCAGAACAAAGAATGAACTACTGATTTCAGCTCTTCAGCAGG 2700
2701 ACATTCTACTCTCTTTCAAGATTAGTAATCTTGCTTTATGAAGGGTAGCATTGTATATTT 2760
2761 AAGCTTAGTCTGTTGCAAGGGAAGGTCTATGCTGTTGAGCTACAGGACTGTGTCTGTTCC 2820
2821 AGAGCAGGAGTTGGGATGCTTGCTGTATGTCCTTCAGGACTTCTTGGATTTGGAATTTGT 2880
2881 GAAAGCTTTGGATTCAGGTGATGTGGAGCTCAGAAATCCTGAAACCAGTGGCTCTGGTAC 2940
2941 TCAGTAGTTAGGGTACCCTGTGCTTCTTGGTGCTTTTCCTTTCTGGAAAATAAGGATTTT 3000
3001 TCTGCTACTGGTAAATATTTTCTGTTTGTGAGAAATATATTAAAGTGTTTCTTTTAAAGG 3060
3061 CGTGCATCATTGTAGTGTGTGCAGGGATGTATGCAGGCAAAACACTGTGTATATAATAAA 3120
3121 TAAATCTTTTTAAAAAGTGTAAAAAAAAAAA  3151
```

INFLUENCE OF TAXOL and TGFβ ON HIAP-2 mRNA ABUNDANCE
IN CISPLATIN-SENSITIVE (OV2008) AND -RESISTANT (C13)
HUMAN EPITHELIAL CANCER CELLS IN VITRO 1: CONTROL  3: CONTROL
2: TAXOL (0.2 μM)  4: TGFβ (20 ng/ml)

INFLUENCE OF TGFβ ON XIAP PROTEIN EXPRESSION AND DNA
FRAGMENTATION IN CISPLATIN-SENSITIVE (OV2008) AND -RESISTANT (C13)
HUMAN OVARIAN EPITHELIAL CANCER CELLS IN VITRO

SEQUENCE LISTING

```
<160> NUMBER OF SEQ ID NOS: 17

<210> SEQ ID NO 1
<211> LENGTH: 46
<212> TYPE: PRT
<213> ORGANISM: Artificial Sequence
<220> FEATURE:
<221> NAME/KEY: UNSURE
<222> LOCATION: (1)...(46)
<223> OTHER INFORMATION: Xaa at 2, 3, 4, 5, 6, 7, 9, 10, 11, 17, 18, 19,
      20, 21, 23, 25, 30, 31, 32, 34, 35, 38, 39, 40,
      41, 42, and 45 can be any amino acid; Xaa at 8 can
      be Glu or Asp; Xaa at 14 and 22 can be Val or Ile.
<223> OTHER INFORMATION: Based on consensus from Homo sapiens and Mus
      musculus

<400> SEQUENCE: 1

Glu Xaa Xaa Xaa Xaa Xaa Xaa Xaa Xaa Xaa Cys Lys Xaa Cys Met
1               5                   10                  15

Xaa Xaa Xaa Xaa Xaa Xaa Xaa Phe Xaa Pro Cys Gly His Xaa Xaa Xaa
                20                  25                  30

Cys Xaa Xaa Cys Ala Xaa Xaa Xaa Xaa Xaa Cys Pro Xaa Cys
            35                  40                  45

<210> SEQ ID NO 2
<211> LENGTH: 68
<212> TYPE: PRT
<213> ORGANISM: Artificial Sequence
<220> FEATURE:
<223> OTHER INFORMATION: Xaa at 1, 2, 3, 6, 9, 10, 14, 15, 18, 19, 20,
      21, 24, 30, 32, 33, 35, 37, 40, 42, 43, 44, 45, 46,
      47, 49, 50, 51, 53, 54, 55, 56, 57, 59, 60, 61,
      62, 64 and 66 can be any amino acid; Xaa at 13, 16
      and 17 can be any amino acid or absent.
<223> OTHER INFORMATION: Based on consensus from Homo sapiens and Mus
      musculus

<400> SEQUENCE: 2

Xaa Xaa Xaa Arg Leu Xaa Thr Phe Xaa Xaa Trp Pro Xaa Xaa Xaa Xaa
1               5                   10                  15

Xaa Xaa Xaa Xaa Xaa Leu Ala Xaa Ala Gly Phe Tyr Tyr Xaa Gly Xaa
                20                  25                  30

Xaa Asp Xaa Val Xaa Cys Phe Xaa Cys Xaa Xaa Xaa Xaa Xaa Xaa Trp
            35                  40                  45

Xaa Xaa Xaa Asp Xaa Xaa Xaa Xaa Xaa His Xaa Xaa Xaa Xaa Pro Xaa
    50                  55                  60

Cys Xaa Phe Val
65

<210> SEQ ID NO 3
<211> LENGTH: 5232
<212> TYPE: DNA
<213> ORGANISM: Homo sapiens
<220> FEATURE:
<221> NAME/KEY: variation
<222> LOCATION: (4623)...(4623)
<223> OTHER INFORMATION: n can be any nucleotide
<220> FEATURE:
<221> NAME/KEY: variation
<222> LOCATION: (4622)...(4622)
```

-continued

<223> OTHER INFORMATION: n can be any nucleotide

<400> SEQUENCE: 3

```
gaaaaggtgg acaagtccta ttttcaagag aagatgactt ttaacagttt tgaaggatct      60
aaaacttgtg tacctgcaga catcaataag gaagaagaat ttgtagaaga gtttaataga     120
ttaaaaactt ttgctaattt tccaagtggt agtcctgttt cagcatcaac actggcacga     180
gcagggtttc tttatactgg tgaaggagat accgtgcggt gctttagttg tcatgcagct     240
gtagatagat ggcaatatgg agactcagca gttggaagac acaggaaagt atccccaaat     300
tgcagattta tcaacggctt ttatcttgaa aatagtgcca cgcagtctac aaattctggt     360
atccagaatg gtcagtacaa agttgaaaac tatctgggaa gcagagatca ttttgcctta     420
gacaggccat ctgagacaca tgcagactat cttttgagaa ctgggcaggt tgtagatata     480
tcagacacca tatcccgag gaaccctgcc atgtatagtg aagaagctag attaaagtcc     540
tttcagaact ggccagacta tgctcaccta accccaagag agttagcaag tgctggactc     600
tactacacag gtattggtga ccaagtgcag tgcttttgtt gtggtggaaa actgaaaaat     660
tgggaacctt gtgatcgtgc ctggtcagaa cacaggcgac actttcctaa ttgcttcttt     720
gttttgggcc ggaatcttaa tattcgaagt gaatctgatg ctgtgagttc tgataggaat     780
ttcccaaatt caacaaatct tccaagaaat ccatccatgg cagattatga agcacggatc     840
tttacttttg ggacatggat atactcagtt aacaaggagc agcttgcaag agctggatttt     900
tatgctttag gtgaaggtga taaagtaaag tgctttcact gtggaggagg gctaactgat     960
tggaagccca gtgaagaccc ttgggaacaa catgctaaat ggtatccagg gtgcaaatat    1020
ctgttagaac agaagggaca agaatatata aacaatattc atttaactca ttcacttgag    1080
gagtgtctgg taagaactac tgagaaaaca ccatcactaa ctagaagaat tgatgatacc    1140
atcttccaaa atcctatggt acaagaagct atacgaatgg ggttcagttt caaggacatt    1200
aagaaaataa tggaggaaaa aattcagata tctgggagca actataaatc acttgaggtt    1260
ctggttgcag atcagtgaa tgctcagaaa gacagtatgc aagatgagtc aagtcagact    1320
tcattacaga aagagattag tactgaagag cagctaaggc gcctgcaaga ggagaagctt    1380
tgcaaaatct gtatggatag aaatattgct atcgttttg ttccttgtgg acatctagtc    1440
acttgtaaac aatgtgctga agcagttgac aagtgtccca tgtgctacac agtcattact    1500
ttcaagcaaa aaattttat gtcttaatct aactctatag taggcatgtt atgttgttct    1560
tattaccctg attgaatgtg tgatgtgaac tgactttaag taatcaggat tgaattccat    1620
tagcatttgc taccaagtag gaaaaaaaat gtacatggca gtgttttagt tggcaatata    1680
atctttgaat ttcttgattt ttcagggtat tagctgtatt atccattttt tttactgtta    1740
tttaattgaa accatagact aagaataaga agcatcatac tataactgaa cacaatgtgt    1800
attcatagta tactgattta attctaagt gtaagtgaat taatcatctg gatttttat    1860
tcttttcaga taggcttaac aaatggagct ttctgtatat aaatgtggag attagagtta    1920
atctccccaa tcacataatt tgttttgtgt gaaaaaggaa taaattgttc catgctggtg    1980
gaaagataga gattgttttt agaggttggt tgttgtgttt taggattctg tccatttttct    2040
tttaaagtta taaacacgta cttgtgcgaa ttattttttt aaagtgattt gccatttttg    2100
aaagcgtatt taatgataga atactatcga gccaacatgt actgacatgg aaagatgtca    2160
aagatatgtt aagtgtaaaa tgcaagtggc aaaacactat gtatagtctg agccagatca    2220
aagtatgtat gttttttaata tgcatagaac aaaagatttg gaaagatata caccaaactg    2280
```

```
ttaaatgtgg ttttctcttcg gggagggggg gattgggga ggggcccag aggggttttta    2340 tagggcctt ttcactttct acttttttca ttttgttctg ttcgaatttt ttataagtat     2400
gtattacttt tgtaatcaga attttagaa agtattttgc tgatttaaag cttaggcat      2460 gttcaaacgc ctgcaaaact acttatcact cagctttagt ttttctaatc caagaaggca    2520
gggcagttaa ccttttttggt gccaatgtga aatgtaaatg attttatgtt tttcctgctt   2580
tgtggatgaa aaatatttct gagtggtagt tttttgacag gtagaccatg tcttatcttg    2640
tttcaaaata agtatttctg attttgtaaa atgaaatata aaatatgtct cagatcttcc    2700
aattaattag taaggattca tccttaatcc ttgctagttt aagcctgcct aagtcacttt    2760
actaaaagat ctttgttaac tcagtatttt aaacatctgt cagcttatgt aggtaaaagt    2820
agaagcatgt ttgtacactg cttgtagtta tagtgacagc tttccatgtt gagattctca    2880
tatcatcttg tatcttaaag tttcatgtga gttttaccg ttaggatgat taagatgtat     2940
ataggacaaa atgttaagtc tttcctctac ctacatttgt tttcttggct agtaatagta    3000
gtagatactt ctgaaataaa tgttctctca agatccttaa aacctcttgg aaattataaa    3060
aatattggca agaaaagaag aatagttgtt taaatatttt ttaaaaaaca cttgaataag    3120
aatcagtagg gtataaacta gaagtttaaa aatgcctcat agaacgtcca gggtttacat    3180
tacaagattc tcacaacaaa cccattgtag aggtgagtaa ggcatgttac tacagaggaa    3240
agtttgagag taaaactgta aaaaattata ttttgttgt actttctaag agaaagagta    3300
ttgttatgtt ctcctaactt ctgttgatta ctactttaag tgatattcat ttaaaacatt    3360
gcaaatttat tttattat taatttctt tttgagatgg agtcttgctt gtcacccagg       3420
ctggagtgca gtggagtgat ctctgctcac tgcaacctcc gccttctggg ttcaagcgat    3480
tctcgtgcct cagcttcctg agtagctgga attacaggca ggtgccacca tgcccgacta    3540 atttttttt attttagta gagacgggt ttcaccatgt tggccaggct ggtatcaaac       3600
tcctgacctc aagagatcca ctcgccttgc cctcccaaag tgctgggatt acaggcttga    3660
gccaccacgc ccggctaaaa cattgcaaat ttaaatgaga gttttaaaaa ttaaataatg    3720
actgccctgt ttctgtttta gtatgtaaat cctcagttct tcacctttgc actgtctgcc    3780
acttagtttg gttatatagt cattaacttg aatttggtct gtatagtcta gactttaaat    3840
ttaaagtttt ctacaagggg agaaaagtgt taaaatttt aaaatatgtt ttccaggaca     3900
cttcacttcc aagtcaggta ggtagttcaa tctagttgtt agccaaggac tcaaggactg    3960
aattgtttta acataaggct tttcctgttc tgggagccgc acttcattaa aattcttcta    4020
aaacttgtat gtttagagtt aagcaagact tttttcttc ctctccatga gttgtgaaat     4080
ttaatgcaca acgctgatgt ggctaacaag tttattttaa gaattgttta gaaatgctgt    4140
tgcttcaggt tcttaaaatc actcagcact ccaacttcta atcaaattt tggagactta     4200 acagcatttg tctgtgtttg aactataaaa agcaccggat cttttccatc taattccgca    4260
aaaattgatc atttgcaaag tcaaaactat agccatatcc aaatcttttc cccctcccaa    4320
gagttctcag tgtctacatg tagactattc cttttctgta taaagttcac tctaggattt    4380
caagtcacca cttattttac attttagtca tgcaaagatt caagtagttt tgcaataagt    4440
acttatcttt atttgtaata atttagtctg ctgatcaaaa gcattgtctt aatttttgag    4500
aactggtttt agcatttaca aactaaattc cagttaatta attaatagct ttatattgcc    4560
tttcctgcta catttggttt ttttcccctgt cccttttgatt acgggctaag gtagggtaag  4620
```

-continued

```
anngggtgta gtgagtgtat ataatgtgat ttggccctgt gtattatgat attttgttat    4680
ttttgttgtt atattattta catttcagta gttgtttttt gtgtttccat tttaggggat    4740
aaaatttgta ttttgaacta tgaatggaga ctaccgcccc agcattagtt tcacatgata    4800 tacccttaa  acccgaatca ttgttttatt tcctgattac acaggtgttg aatggggaaa    4860
ggggctagta tatcagtagg atatactatg ggatgtatat atatcattgc tgttagagaa    4920
atgaaataaa atggggctgg gctcagtggc tcacgcctgt aatcccagca ctttgggagg    4980
ctgaggcagg tggatcacga ggtcaggaga tcgagaccat cctggctaac acggtgaaac    5040
cccgtctcta ctaaaaaaca gaaaattagc cgggcgtggt ggcgggcgcc tgtagtccca    5100
gctactcggg aggctgaggc aggagaatgg tgtgaacccg ggaggcagag cttgcagtga    5160
gccgagatct cgccactgca ctccagcctg ggcaacagag caagactctg tctcaaaaaa    5220
aaaaaaaaaa ag                                                        5232
```

<210> SEQ ID NO 4
<211> LENGTH: 497
<212> TYPE: PRT
<213> ORGANISM: Homo sapiens

<400> SEQUENCE: 4

```
Met Thr Phe Asn Ser Phe Glu Gly Ser Lys Thr Cys Val Pro Ala Asp
 1               5                  10                  15

Ile Asn Lys Glu Glu Glu Phe Val Glu Phe Asn Arg Leu Lys Thr
                20                  25                  30

Phe Ala Asn Phe Pro Ser Gly Ser Pro Val Ser Ala Ser Thr Leu Ala
            35                  40                  45

Arg Ala Gly Phe Leu Tyr Thr Gly Glu Gly Asp Thr Val Arg Cys Phe
        50                  55                  60

Ser Cys His Ala Ala Val Asp Arg Trp Gln Tyr Gly Asp Ser Ala Val
    65                  70                  75                  80

Gly Arg His Arg Lys Val Ser Pro Asn Cys Arg Phe Ile Asn Gly Phe
                85                  90                  95

Tyr Leu Glu Asn Ser Ala Thr Gln Ser Thr Asn Ser Gly Ile Gln Asn
               100                 105                 110

Gly Gln Tyr Lys Val Glu Asn Tyr Leu Gly Ser Arg Asp His Phe Ala
           115                 120                 125

Leu Asp Arg Pro Ser Glu Thr His Ala Asp Tyr Leu Leu Arg Thr Gly
       130                 135                 140

Gln Val Val Asp Ile Ser Asp Thr Ile Tyr Pro Arg Asn Pro Ala Met
145                 150                 155                 160

Tyr Cys Glu Glu Ala Arg Leu Lys Ser Phe Gln Asn Trp Pro Asp Tyr
                165                 170                 175

Ala His Leu Thr Pro Arg Glu Leu Ala Ser Ala Gly Leu Tyr Tyr Thr
            180                 185                 190

Gly Ile Gly Asp Gln Val Gln Cys Phe Cys Cys Gly Gly Lys Leu Lys
        195                 200                 205

Asn Trp Glu Pro Cys Asp Arg Ala Trp Ser Glu His Arg Arg His Phe
    210                 215                 220

Pro Asn Cys Phe Phe Val Leu Gly Arg Asn Leu Asn Ile Arg Ser Glu
225                 230                 235                 240

Ser Asp Ala Val Ser Ser Asp Arg Asn Phe Pro Asn Ser Thr Asn Leu
                245                 250                 255

Pro Arg Asn Pro Ser Met Ala Asp Tyr Glu Ala Arg Ile Phe Thr Phe
```

-continued

```
                260                 265                 270
Gly Thr Trp Ile Tyr Ser Val Asn Lys Glu Gln Leu Ala Arg Ala Gly
            275                 280                 285
Phe Tyr Ala Leu Gly Glu Gly Asp Lys Val Lys Cys Phe His Cys Gly
        290                 295                 300
Gly Gly Leu Thr Asp Trp Lys Pro Ser Glu Asp Pro Trp Glu Gln His
305                 310                 315                 320
Ala Lys Trp Tyr Pro Gly Cys Lys Tyr Leu Leu Glu Gln Lys Gly Gln
                325                 330                 335
Glu Tyr Ile Asn Asn Ile His Leu Thr His Ser Leu Glu Glu Cys Leu
            340                 345                 350
Val Arg Thr Thr Glu Lys Thr Pro Ser Leu Thr Arg Arg Ile Asp Asp
        355                 360                 365
Thr Ile Phe Gln Asn Pro Met Val Gln Glu Ala Ile Arg Met Gly Phe
    370                 375                 380
Ser Phe Lys Asp Ile Lys Lys Ile Met Glu Glu Lys Ile Gln Ile Ser
385                 390                 395                 400
Gly Ser Asn Tyr Lys Ser Leu Glu Val Leu Val Ala Asp Leu Val Asn
                405                 410                 415
Ala Gln Lys Asp Ser Met Gln Asp Glu Ser Ser Gln Thr Ser Leu Gln
            420                 425                 430
Lys Glu Ile Ser Thr Glu Gln Leu Arg Arg Leu Gln Glu Glu Lys
        435                 440                 445
Leu Cys Lys Ile Cys Met Asp Arg Asn Ile Ala Ile Val Phe Val Pro
    450                 455                 460
Cys Gly His Leu Val Thr Cys Lys Gln Cys Ala Glu Ala Val Asp Lys
465                 470                 475                 480
Cys Pro Met Cys Tyr Thr Val Ile Thr Phe Lys Gln Lys Ile Phe Met
                485                 490                 495
Ser
```

<210> SEQ ID NO 5
<211> LENGTH: 6669
<212> TYPE: DNA
<213> ORGANISM: Homo sapiens
<220> FEATURE:
<221> NAME/KEY: variation
<222> LOCATION: (3677)...(3951)
<223> OTHER INFORMATION: n can be any nucleotide

<400> SEQUENCE: 5

```
ttgctctgtc acccagtttg gagtgcagtt atgcagtctc acactgcaag ctctgcctca     60
tgggctcaag tgaacctcct gcctcagcct ctcaagtagc tgggaccaca ggcaggtgcc    120
accatgtctg ctaattttt gagtttcttt gtagagatgg tgttttgcca agtcacccag    180
tttgaggctg gtctcaaaca cctgggctca agcaatccat ctacctcagc ctcccaaagt    240
gctgggatta caggagtgag ccatggcatg aggccttgtg gggtgtctct tttaaatgaa    300
agcatactct gtttacgtat tgatatgaa ggaatatcct tcctttccac aaagacaaaa    360
attatcctat ttttctcaaa acatatgtcc tttttctcta cttttcattt ttgttacttt    420
tgatggacac atgtgttaca ttgatttcac tttctcataa ttctgctgta agaaaaacaa    480
tagtgccagt tcaatgacaa atagcaacag tctgttattg ctagactgtt actgttagtg    540
gagactacca gaacagtcag tcccagtgtc agggaatcaa agagaacatg ttccctctct    600
aaagggcaca gctgctgctc agctttagct gattgctgcc ctgcaggact ataggcccag    660
```

-continued

```
tgttgctaga tcttttgatg tttcaagaga agcttggaat ctagaatgtg atgggaagtc    720
tcttacattt aaacatgttg gcaattaatg gtaagattta aaaatactgt ggtccaagaa    780
aaaaatggat ttggaaactg gattaaattc aaatgaggca tgcagattaa tctacagcat    840
ggtacaatgt gaattttctg gtttctttaa ttgcactgta attaggtaag atgttagctt    900
tggggaagct aagtgcagag tatgcagaaa ctattatttt tgtaagtttt ctctaagtat    960
aaataaattt caaaataaaa ataaaaactt agtaaagaac tataatgcaa ttctatgtaa   1020
gccaaacata atatgtcttc cagtttgaaa cctctgggtt ttattttatt ttattttatt   1080
tttgagacag agtcttgctg tgtcacccag gctggagtgt agtggcacta tttcggccca   1140
ctgcaacctc cacctcccag gctcaaatga ttctcctgcc tcagcctccg gagtagctgg   1200
gattacaggc gcgtaccacc acacccagct aattttttgta tttttagtag agatggggtt   1260
tcaccatttt ggccaggctg gttttgaact cctgacctca gtgatccac ttgtcttggc    1320 ctcccaaaat gctgggatta caggcgtgag ccactgcacc aggcagaggc ctctgttttt   1380
tatctctttt tggcctctac agtgcctagt aaagcacctg atacatggta aacgatcagt   1440
aattactagt actctatttt ggagaaaatg attttttaaa aagtcattgt gttccatcca   1500
tgagtcgttt gagtttttaaa actgtctttt tgtttgtttt tgaacaggtt tacaaaggag   1560
gaaaacgact tcttctagat tttttttttca gtttcttcta taaatcaaaa catctcaaaa   1620
tggagaccta aaatccttaa agggacttag tctaatctcg ggaggtagtt ttgtgcatgg   1680
gtaaacaaat taagtattaa ctggtgtttt actatccaaa gaatgctaat tttataaaca   1740
tgatcgagtt atataaggta taccataatg agtttgattt tgaatttgat ttgtggaaat   1800
aaaggaaaag tgattctagc tggggcatat tgttaaagca ttttttttcag agttggccag   1860 gcagtctcct actggcacat tctcccatta tgtagaatag aaatagtacc tgtgtttggg   1920
aaagatttta aaatgagtga cagttatttg gaacaaagag ctaataatca atccactgca   1980
aattaaagaa acatgcagat gaaagttttg acacattaaa atacttctac agtgacaaag   2040
aaaaatcaag aacaaagctt tttgatatgt gcaacaaatt tagaggaagt aaaaagataa   2100
atgtgatgat tggtcaagaa attatccagt tatttacaag gccactgata ttttaaacgt   2160
ccaaaagttt gtttaaatgg gctgttaccg ctgagaatga tgaggatgag aatgatggtt   2220
gaaggttaca ttttaggaaa tgaagaaact tagaaaatta atataaagac agtgatgaat   2280
acaaagaaga tttttataac aatgtgtaaa attttttggcc agggaaagga atattgaagt   2340
tagatacaat tacttacctt tgagggaaat aattgttggt aatgagatgt gatgtttctc   2400
ctgccacctg gaaacaaagc attgaagtct gcagttgaaa agcccaacgt ctgtgagatc   2460
caggaaacca tgcttgcaaa ccactggtaa aaaaaaaaa aaaaaaaaa aaagccacag    2520 tgacttgctt attggtcatt gctagtatta tcgactcaga acctctttac taatggctag   2580
taaatcataa ttgagaaatt ctgaattttg acaaggtctc tgctgttgaa atggtaaatt   2640
tattattttt tttgtcatga taaattctgg ttcaaggtat gctatccatg aaataatttc   2700
tgaccaaaac taaattgatg caatttgatt atccatctta gcctacagat ggcatctggt   2760
aacttttgac tgttttaaaa aataaatcca ctatcagagt agatttgatg ttggcttcag   2820
aaacatttag aaaacaaaa gttcaaaaat gttttcagga ggtgataagt tgaataactc   2880
tacaatgtta gttcttgag ggggacaaaa aatttaaaat ctttgaaagg tcttatttta   2940
cagccatatc taaattatct taagaaaatt tttaacaaag ggaatgaaat atatatcatg   3000
```

```
attctgtttt tccaaaagta acctgaatat agcaatgaag ttcagttttg ttattggtag    3060
tttgggcaga gtctcttttt gcagcacctg ttgtctacca taattacaga ggacatttcc    3120
atgttctagc caagtatact attagaataa aaaaacttaa cattgagttg cttcaacagc    3180
atgaaactga gtccaaaaga ccaaatgaac aaacacatta atctctgatt atttatttta    3240
aatagaatat ttaattgtgt aagatctaat agtatcatta tacttaagca atcatattcc    3300
tgatgatcta tgggaaataa ctattattta attaatattg aaaccaggtt ttaagatgtg    3360
ttagccagtc ctgttactag taaatctctt tatttggaga gaaattttag attgttttgt    3420
tctccttatt agaaggattg tagaaagaaa aaaatgacta attggagaaa aattggggat    3480
atatcatatt tcactgaatt caaaatgtct tcagttgtaa atcttaccat tattttacgt    3540
acctctaaga aataaaagtg cttctaatta aaatatgatg tcattaatta tgaaatactt    3600
cttgataaca gaagttttaa aatagccatc ttagaatcag tgaaatatgg taatgtatta    3660
ttttcctcct ttgagtnagg tcttgtgctt tttnttcctg gccactaaat ntcaccatnt    3720
ccaanaagca aantaaacct attctgaata tttttgctgt gaaacacttg ncagcagagc    3780
tttcccncca tgnnagaagc ttcatgagtc acacattaca tctttgggtt gattgaatgc    3840
cactgaaaca tttctagtag cctggagnag ttgacctacc tgtggagatg cctgccatta    3900
aatggcatcc tgatggctta atacacatca ctcttctgtg nagggtttta attttcaaca    3960
cagcttactc tgtagcatca tgtttacatt gtatgtataa agattatacn aaggtgcaat    4020
tgtgtatttc ttccttaaaa tgtatcagta taggatttag aatctccatg ttgaaactct    4080
aaatgcatag aaataaaaat aataaaaaat ttttcatttt ggcttttcag cctagtatta    4140
aaactgataa aagcaaagcc atgcacaaaa ctacctccct agagaaaggc tagtcccttt    4200
tcttccccat tcatttcatt atgaacatag tagaaaacag catattctta tcaaatttga    4260 tgaaagcgc caacacgttt gaactgaaat acgacttgtc atgtgaactg taccgaatgt    4320
ctacgtattc cacttttcct gctggggttc ctgtctcaga aaggagtctt gctcgtgctg    4380
gtttctatta cactggtgtg aatgacaagg tcaaatgctt ctgttgtggc ctgatgctgg    4440
ataactggaa aagaggagac agtcctactg aaaagcataa aagttgtat cctagctgca    4500 gattcgttca gagtctaaat tccgttaaca acttggaagc tacctctcag cctacttttc    4560
cttcttcagt aacacattcc acacactcat tacttccggg tacagaaaac agtggatatt    4620
tccgtggctc ttattcaaac tctccatcaa atcctgtaaa ctccagagca aatcaagaat    4680
tttctgcctt gatgagaagt tcctaccect gtccaatgaa taacgaaaat gccagattac    4740 ttactttca gacatggcca ttgacttttc tgtcgccaac agatctggca cgagcaggct    4800
tttactacat aggacctgga gacagagtgg cttgctttgc ctgtggtgga aaattgagca    4860
attgggaacc gaaggataat gctatgtcag aacacctgag acattttccc aaatgcccat    4920
ttatagaaaa tcagcttcaa gacacttcaa gatacacagt ttctaatctg agcatgcaga    4980
cacatgcagc ccgcttttaaa acattcttta actggccctc tagtgttcta gttaatcctg    5040
agcagcttgc aagtgcgggt ttttattatg tgggtaacag tgatgatgtc aaatgctttt    5100
gctgtgatgg tggactcagg tgttgggaat ctggagatga tccatgggtt caacatgcca    5160
agtggtttcc aaggtgtgag tacttgataa gaattaaagg acaggagttc atccgtcaag    5220
ttcaagccag ttaccctcat ctacttgaac agctgctatc cacatcagac agcccaggag    5280
atgaaaatgc agagtcatca attatccatt ttgaacctgg agaagaccat tcagaagatg    5340
caatcatgat gaatactcct gtgattaatg ctgccgtgga aatgggcttt agtagaagcc    5400
```

```
tggtaaaaca gacagttcag agaaaaatcc tagcaactgg agagaattat agactagtca    5460
atgatcttgt gttagactta ctcaatgcag aagatgaaat aagggaagag gagagagaaa    5520
gagcaactga ggaaaaagaa tcaaatgatt tattattaat ccggaagaat agaatggcac    5580
tttttcaaca tttgacttgt gtaattccaa tcctggatag tctactaact gccggaatta    5640
ttaatgaaca agaacatgat gttattaaac agaagacaca gacgtcttta caagcaagag    5700
aactgattga tacgatttta gtaaaaggaa atattgcagc cactgtattc agaaactctc    5760
tgcaagaagc tgaagctgtg ttatatgagc atttatttgt gcaacaggac ataaaatata    5820
ttcccacaga agatgtttca gatctaccag tggaagaaca attgcggaga ctacaagaag    5880
aaagaacatg taaagtgtgt atggacaaag aagtgtccat agtgtttatt ccttgtggtc    5940
atctagtagt atgcaaagat tgtgctcctt ctttaagaaa gtgtcctatt tgtaggagta    6000
caatcaaggg tacagttcgt acatttcttt catgaagaag aaccaaaaca tcgtctaaac    6060
tttagaatta atttattaaa tgtattataa ctttaacttt tatcctaatt tggtttcctt    6120
aaaattttta tttatttaca actcaaaaaa cattgttttg tgtaacatat ttatatatgt    6180
atctaaacca tatgaacata tatttttttag aaactaagag aatgataggc ttttgttctt    6240
atgaacgaaa aagaggtagc actacaaaca caatattcaa tcaaaatttc agcattattg    6300
aaattgtaag tgaagtaaaa cttaagatat ttgagttaac ctttaagaat tttaaatatt    6360
ttggcattgt actaataccg ggaacatgaa gccaggtgtg gtggtatgtg cctgtagtcc    6420
caggctgagg caagagaatt acttgagccc aggagtttga atccatcctg ggcagcatac    6480
tgagaccctg cctttaaaaa caaacagaac aaaaacaaaa caccagggac acatttctct    6540
gtcttttttg atcagtgtcc tatacatcga aggtgtgcat atatgttgaa tcacatttta    6600
gggacatggt gttttttataa agaattctgt gagaaaaaat ttaataaagc aaccaaaaaa    6660
aaaaaaaaa                                                             6669

<210> SEQ ID NO 6
<211> LENGTH: 604
<212> TYPE: PRT
<213> ORGANISM: Homo sapiens

<400> SEQUENCE: 6

Met Asn Ile Val Glu Asn Ser Ile Phe Leu Ser Asn Leu Met Lys Ser
1               5                   10                  15

Ala Asn Thr Phe Glu Leu Lys Tyr Asp Leu Ser Cys Glu Leu Tyr Arg
            20                  25                  30

Met Ser Thr Tyr Ser Thr Phe Pro Ala Gly Val Pro Val Ser Glu Arg
        35                  40                  45

Ser Leu Ala Arg Ala Gly Phe Tyr Tyr Thr Gly Val Asn Asp Lys Val
    50                  55                  60

Lys Cys Phe Cys Cys Gly Leu Met Leu Asp Asn Trp Lys Arg Gly Asp
65                  70                  75                  80

Ser Pro Thr Glu Lys His Lys Lys Leu Tyr Pro Ser Cys Arg Phe Val
                85                  90                  95

Gln Ser Leu Asn Ser Val Asn Asn Leu Glu Ala Thr Ser Gln Pro Thr
            100                 105                 110

Phe Pro Ser Ser Val Thr His Ser Thr His Ser Leu Leu Pro Gly Thr
        115                 120                 125

Glu Asn Ser Gly Tyr Phe Arg Gly Ser Tyr Ser Asn Ser Pro Ser Asn
    130                 135                 140
```

-continued

```
Pro Val Asn Ser Arg Ala Asn Gln Glu Phe Ser Ala Leu Met Arg Ser
145                 150                 155                 160
Ser Tyr Pro Cys Pro Met Asn Asn Glu Asn Ala Arg Leu Leu Thr Phe
                165                 170                 175
Gln Thr Trp Pro Leu Thr Phe Leu Ser Pro Thr Asp Leu Ala Arg Ala
            180                 185                 190
Gly Phe Tyr Tyr Ile Gly Pro Gly Asp Arg Val Ala Cys Phe Ala Cys
                195                 200                 205
Gly Gly Lys Leu Ser Asn Trp Glu Pro Lys Asp Asn Ala Met Ser Glu
210                 215                 220
His Leu Arg His Phe Pro Lys Cys Pro Phe Ile Glu Asn Gln Leu Gln
225                 230                 235                 240
Asp Thr Ser Arg Tyr Thr Val Ser Asn Leu Ser Met Gln Thr His Ala
                245                 250                 255
Ala Arg Phe Lys Thr Phe Phe Asn Trp Pro Ser Ser Val Leu Val Asn
                260                 265                 270
Pro Glu Gln Leu Ala Ser Ala Gly Phe Tyr Tyr Val Gly Asn Ser Asp
            275                 280                 285
Asp Val Lys Cys Phe Cys Cys Asp Gly Gly Leu Arg Cys Trp Glu Ser
290                 295                 300
Gly Asp Asp Pro Trp Val Gln His Ala Lys Trp Phe Pro Arg Cys Glu
305                 310                 315                 320
Tyr Leu Ile Arg Ile Lys Gly Gln Glu Phe Ile Arg Gln Val Gln Ala
                325                 330                 335
Ser Tyr Pro His Leu Leu Glu Gln Leu Leu Ser Thr Ser Asp Ser Pro
            340                 345                 350
Gly Asp Glu Asn Ala Glu Ser Ser Ile Ile His Leu Glu Pro Gly Glu
            355                 360                 365
Asp His Ser Glu Asp Ala Ile Met Met Asn Thr Pro Val Ile Asn Ala
            370                 375                 380
Ala Val Glu Met Gly Phe Ser Arg Ser Leu Val Lys Gln Thr Val Gln
385                 390                 395                 400
Arg Lys Ile Leu Ala Thr Gly Glu Asn Tyr Arg Leu Val Asn Asp Leu
                405                 410                 415
Val Leu Asp Leu Leu Asn Ala Glu Asp Glu Ile Arg Glu Glu Glu Arg
            420                 425                 430
Glu Arg Ala Thr Glu Glu Lys Ser Asn Asp Leu Leu Leu Ile Arg
            435                 440                 445
Lys Asn Arg Met Ala Leu Phe Gln His Leu Thr Cys Val Ile Pro Ile
450                 455                 460
Leu Asp Ser Leu Leu Thr Ala Gly Ile Ile Asn Glu Gln Glu His Asp
465                 470                 475                 480
Val Ile Lys Gln Lys Thr Gln Thr Ser Leu Gln Ala Arg Glu Leu Ile
                485                 490                 495
Asp Thr Ile Leu Val Lys Gly Asn Ile Ala Ala Thr Val Phe Arg Asn
            500                 505                 510
Ser Leu Gln Glu Ala Glu Ala Val Leu Tyr Glu His Leu Phe Val Gln
            515                 520                 525
Gln Asp Ile Lys Tyr Ile Pro Thr Glu Asp Val Ser Asp Leu Pro Val
            530                 535                 540
Glu Glu Gln Leu Arg Arg Leu Pro Glu Gly Arg Thr Cys Lys Val Cys
545                 550                 555                 560
```

```
Met Asp Lys Glu Val Ser Ile Val Phe Ile Pro Cys Gly His Leu Val
            565                 570                 575

Val Cys Lys Asp Cys Ala Pro Ser Leu Arg Lys Cys Pro Ile Cys Arg
            580                 585                 590

Ser Thr Ile Lys Gly Thr Val Arg Thr Phe Leu Ser
            595                 600

<210> SEQ ID NO 7
<211> LENGTH: 3732
<212> TYPE: DNA
<213> ORGANISM: Homo sapiens

<400> SEQUENCE: 7
gagcgcccgg gctgatccga gccgagcggg ccgtatctcc ttgtcggcgc cgctgattcc      60
cggctctgcg gaggcctcta ggcagccgcg cagcttccgt gtttgctgcg cccgcactgc     120
gatttacaac cctgaagaat ctccctatcc ctattttgtc cccctgcagt aataaatccc     180
attatggaga tctcgaaact ttataaaggg atatagtttg aattctatgg agtgtaattt     240
tgtgtatgaa ttatatttt aaaacattga agagttttca gaaagaaggc tagtagagtt     300
gattactgat actttatgct aagcagtact ttttggtag tacaatattt tgttaggcgt     360
ttctgataac actagaaagg acaagtttta tcttgtgata aattgattaa tgtttacaac     420
atgactgata attatagctg aatagtcctt aaatgatgaa caggttattt agttttaaa     480 tgcagtgtaa aaagtgtgct gtggaaattt tatggctaac taagtttatg gagaaaatac    540
cttcagttga tcaagaataa tagtggtata caaagttagg aagaaagtca acatgatgct    600
gcaggaaatg gaaacaaata caaatgatat ttaacaaaga tagagtttac agtttttgaa    660
ctttaagcca aattcatttg acatcaagca ctatagcagg cacaggttca acaaagcttg    720
tgggtattga cttcccccaa aagttgtcag ctgaagtaat ttagcccact taagtaaata    780
ctatgatgat aagctgtgtg aacttagctt ttaaatagtg tgaccatatg aaggttttaa    840
ttacttttgt ttattggaat aaaatgagat ttttgggtt gtcatgttaa agtgcttata    900
gggaaagaag cctgcatata attttttacc ttgtggcata atcagtaatt ggtctgttat    960
tcaggcttca tagcttgtaa ccaaatataa ataaaaggca taatttaggt attctatagt   1020
tgcttagaat tttgttaata taaatctctg tgaaaaatca aggagtttta atattttcag   1080
aagtgcatcc accttccagg gctttaagtt agtattaact caagattatg aacaaatagc   1140
acttaggtta cctgaaagag ttactacaac cccaaagagt tgtgttctaa gtagtatctt   1200
ggtaattcag agagatactc atcctacctg aatataaact gagataaatc cagtaaagaa   1260
agtgtagtaa attctacata agagtctatc attgattct ttttgtggta aaaatcttag   1320
ttcatgtgaa gaaatttcat gtgaatgttt tagctatcaa acagtactgt cacctactca   1380
tgcacaaaac tgcctcccaa agactttcc caggtccctc gtatcaaaac attaagagta   1440
taatggaaga tagcacgatc ttgtcagatt ggacaaacag caacaaacaa aaaatgaagt   1500
atgacttttc ctgtgaactc tacagaatgt ctacatattc aactttcccc gccggggtgc   1560
ctgtctcaga aaggagtctt gctcgtgctg gttttttatta tactggtgtg aatgacaagg   1620
tcaaatgctt ctgttgtggc ctgatgctgg ataactggaa actaggagac agtcctattc   1680
aaaagcataa acagctatat cctagctgta gctttattca gaatctggtt tcagctagtc   1740
tgggatccac ctctaagaat acgtctccaa tgagaaacag ttttgcacat tcattatctc   1800
ccaccttgga acatagtagc ttgttcagtg gttcttactc cagcctttct ccaaaccctc   1860
```

```
ttaattctag agcagttgaa gacatctctt catcgaggac taaccccctac agttatgcaa     1920 tgagtactga agaagccaga tttcttacct accatatgtg gccattaact tttttgtcac     1980
catcagaatt ggcaagagct ggtttttatt atataggacc tggagatagg gtagcctgct     2040
ttgcctgtgg tgggaagctc agtaactggg aaccaaagga tgatgctatg tcagaacacc     2100
ggaggcattt tcccaactgt ccattttttgg aaaattctct agaaactctg aggtttagca    2160
tttcaaatct gagcatgcag acacatgcag ctcgaatgag aacatttatg tactggccat     2220
ctagtgttcc agttcagcct gagcagcttg caagtgctgg ttttttattat gtgggtcgca    2280 atgatgatgt caaatgcttt tgttgtgatg gtggcttgag gtgttgggaa tctggagatg     2340
atccatgggt agaacatgcc aagtggtttc caaggtgtga gttcttgata cgaatgaaag     2400
gccaagagtt tgttgatgag attcaaggta gatatcctca tcttcttgaa cagctgttgt     2460
caacttcaga taccactgga gaagaaaatg ctgacccacc aattattcat tttgacctg      2520 gagaaagttc ttcagaagat gctgtcatga tgaatacacc tgtggttaaa tctgccttgg    2580
aaatgggctt aatagagac ctggtgaaac aaacagttca agtaaaatc ctgacaactg       2640 gagagaacta taaaacagtt aatgatattg tgtcagcact tcttaatgct gaagatgaaa     2700
aaagagaaga ggagaaggaa aaacaagctg agaaatggc atcagatgat ttgtcattaa      2760
ttcggaagaa cagaatggct ctctttcaac aattgacatg tgtgcttcct atcctggata    2820 atctttaaa ggccaatgta attaataaac aggaacatga tattattaaa caaaaacac      2880 agatacctt acaagcgaga gaactgattg ataccattt ggttaaagga aatgctgcgg     2940
ccaacatctt caaaaactgt ctaaaagaaa ttgactctac attgtataag aacttatttg    3000
tggataagaa tatgaagtat atcccaacag aagatgtttc aggtctgtca ctggaagaac    3060
aattgaggag gttgcaagaa gaacgaactt gtaaagtgtg tatggacaaa gaagtttctg    3120
ttgtatttat tccttgtggt catctggtag tatgccagga atgtgcccct tctctaagaa    3180
aatgccctat ttgcagggggt ataatcaagg gtactgttcg tacatttctc tcttaaagaa   3240
aaatagtcta tattttaacc tgcataaaaa ggtctttaaa atattgttga acacttgaag    3300
ccatctaaag taaaaaggga attatgagtt tttcaattag taacattcat gttctagtct    3360
gctttggtac taataatctt gtttctgaaa agatggtatc atatatttaa tcttaatctg   3420
tttatttaca agggaagatt tatgtttggt gaactatatt agtatgtatg tgtacctaag    3480
ggagtagtgt cactgcttgt tatgcatcat ttcaggagtt actggatttg ttgttctttc    3540
agaaagcttt gaatactaaa ttatagtgta gaaaagaact ggaaaccagg aactctggag    3600
ttcatcagag ttatggtgcc gaattgtctt tggtgctttt cacttgtgtt ttaaaataag    3660 gattttctc ttatttctcc ccctagtttg tgagaaacat ctcaataaag tgctttaaaa    3720
agaaaaaaaa aa                                                       3732
```

<210> SEQ ID NO 8
<211> LENGTH: 618
<212> TYPE: PRT
<213> ORGANISM: Homo sapiens

<400> SEQUENCE: 8

Met His Lys Thr Ala Ser Gln Arg Leu Phe Pro Gly Pro Ser Tyr Gln
 1               5                  10                  15

Asn Ile Lys Ser Ile Met Glu Asp Ser Thr Ile Leu Ser Asp Trp Thr
            20                  25                  30

Asn Ser Asn Lys Gln Lys Met Lys Tyr Asp Phe Ser Cys Glu Leu Tyr

```
            35                  40                  45
Arg Met Ser Thr Tyr Ser Thr Phe Pro Ala Gly Val Pro Val Ser Glu
     50                  55                  60

Arg Ser Leu Ala Arg Ala Gly Phe Tyr Tyr Thr Gly Val Asn Asp Lys
 65                  70                  75                  80

Val Lys Cys Phe Cys Cys Gly Leu Met Leu Asp Asn Trp Lys Leu Gly
                 85                  90                  95

Asp Ser Pro Ile Gln Lys His Lys Gln Leu Tyr Pro Ser Cys Ser Phe
                100                 105                 110

Ile Gln Asn Leu Val Ser Ala Ser Leu Gly Ser Thr Ser Lys Asn Thr
            115                 120                 125

Ser Pro Met Arg Asn Ser Phe Ala His Ser Leu Ser Pro Thr Leu Glu
        130                 135                 140

His Ser Ser Leu Phe Ser Gly Ser Tyr Ser Ser Leu Pro Pro Asn Pro
145                 150                 155                 160

Leu Asn Ser Arg Ala Val Glu Asp Ile Ser Ser Arg Thr Asn Pro
                165                 170                 175

Tyr Ser Tyr Ala Met Ser Thr Glu Glu Ala Arg Phe Leu Thr Tyr His
                180                 185                 190

Met Trp Pro Leu Thr Phe Leu Ser Pro Ser Glu Leu Ala Arg Ala Gly
            195                 200                 205

Phe Tyr Tyr Ile Gly Pro Gly Asp Arg Val Ala Cys Phe Ala Cys Gly
     210                 215                 220

Gly Lys Leu Ser Asn Trp Glu Pro Lys Asp Asp Ala Met Ser Glu His
225                 230                 235                 240

Arg Arg His Phe Pro Asn Cys Pro Phe Leu Glu Asn Ser Leu Glu Thr
                245                 250                 255

Leu Arg Phe Ser Ile Ser Asn Leu Ser Met Gln Thr His Ala Ala Arg
            260                 265                 270

Met Arg Thr Phe Met Tyr Trp Pro Ser Ser Val Pro Val Gln Pro Glu
        275                 280                 285

Gln Leu Ala Ser Ala Gly Phe Tyr Tyr Val Gly Arg Asn Asp Asp Val
    290                 295                 300

Lys Cys Phe Gly Cys Asp Gly Gly Leu Arg Cys Trp Glu Ser Gly Asp
305                 310                 315                 320

Asp Pro Trp Val Glu His Ala Lys Trp Phe Pro Arg Cys Glu Phe Leu
                325                 330                 335

Ile Arg Met Lys Gly Gln Glu Phe Val Asp Glu Ile Gln Gly Arg Tyr
            340                 345                 350

Pro His Leu Leu Glu Gln Leu Leu Ser Thr Ser Asp Thr Thr Gly Glu
        355                 360                 365

Glu Asn Ala Asp Pro Pro Ile Ile His Phe Gly Pro Gly Glu Ser Ser
    370                 375                 380

Ser Glu Asp Ala Val Met Met Asn Thr Pro Val Val Lys Ser Ala Leu
385                 390                 395                 400

Glu Met Gly Phe Asn Arg Asp Leu Val Lys Gln Thr Val Leu Ser Lys
                405                 410                 415

Ile Leu Thr Thr Gly Glu Asn Tyr Lys Thr Val Asn Asp Ile Val Ser
            420                 425                 430

Ala Leu Leu Asn Ala Glu Asp Glu Lys Arg Glu Glu Lys Glu Lys
        435                 440                 445

Gln Ala Glu Glu Met Ala Ser Asp Asp Leu Ser Leu Ile Arg Lys Asn
    450                 455                 460
```

```
Arg Met Ala Leu Phe Gln Gln Leu Thr Cys Val Leu Pro Ile Leu Asp
465                 470                 475                 480

Asn Leu Leu Lys Ala Asn Val Ile Asn Lys Gln Glu His Asp Ile Ile
                485                 490                 495

Lys Gln Lys Thr Gln Ile Pro Leu Gln Ala Arg Glu Leu Ile Asp Thr
            500                 505                 510

Ile Trp Val Lys Gly Asn Ala Ala Ala Asn Ile Phe Lys Asn Cys Leu
        515                 520                 525

Lys Glu Ile Asp Ser Thr Leu Tyr Lys Asn Leu Phe Val Asp Lys Asn
    530                 535                 540

Met Lys Tyr Ile Pro Thr Glu Asp Val Ser Gly Leu Ser Leu Glu Glu
545                 550                 555                 560

Gln Leu Arg Arg Leu Gln Glu Glu Arg Thr Cys Lys Val Cys Met Asp
                565                 570                 575

Lys Glu Val Ser Val Val Phe Ile Pro Cys Gly His Leu Val Val Cys
            580                 585                 590

Gln Glu Cys Ala Pro Ser Leu Arg Lys Cys Pro Ile Cys Arg Gly Ile
        595                 600                 605

Ile Lys Gly Thr Val Arg Thr Phe Leu Ser
    610                 615

<210> SEQ ID NO 9
<211> LENGTH: 2691
<212> TYPE: DNA
<213> ORGANISM: Mus musculus

<400> SEQUENCE: 9
attttttaaa ttgatgcatt aacattctaa acattcatct gtttttaaat agtaaaaatt        60
gaactttgcc ttgaatatgt aatgattcat tataacaatt atgcatagtc tttaataatc       120
tgcatatttt atgctgcttt catgtttttc ctaattaatg acttcacatg tttaatatttt      180
ataattttc tgtcatagtt tccatattta tataaaatga atacttaaga tcagtaattc        240
tgctctgttt gtttatatac tattttccat caaaagacaa aatgggactg aggttgaggc       300
tcgttgctaa agcactttcc taaaatgcaa aaggccctat gatggatccc tagtacttat      360
ttaagtgaga gagaaacagg ctgggggtgt aggtctgtta gagcatgtgt ttggcattat      420
gtgaagccca acactaaaa aaggagaaca acaaaagcg cagactttaa aactcaagtg         480
gtttggtaat gtacgactct actgtttaga attaaaatgt gtcttagtta ttgtgccatt       540
attttttatgt catcactgga taatatatta gtgcttagta tcagaaatag tccttatgct     600
ttgtgttttg aagttcctaa tgcaatgttc tctttctaga aaggtggac aagtcctatt       660
ttccagagaa gatgactttt aacagttttg aaggaactag aacttttgta cttgcagaca      720
ccaataagga tgaagaattt gtagaagagt ttaatagatt aaaaacattt gctaacttcc      780
caagtagtag tcctgtttca gcatcaacat tggcgcgagc tgggttttctt tataccggtg    840
aaggagacac cgtgcaatgt ttcagttgtc atgcggcaat agatagatgg cagtatggag      900
actcagctgt tggaagacac aggagaatat ccccaaattg cagatttatc aatggttttt      960
attttgaaaa tggtgctgca cagtctacaa atcctggtat ccaaaatggc cagtacaaat     1020
ctgaaaactg tgtgggaaat agaaatcctt ttgcccctga caggccacct gagactcatg     1080
ctgattatct cttgagaact ggacaggttg tagatatttc agacaccata tacccgagga     1140
accctgccat gtgtagtgaa gaagccagat tgaagtcatt tcagaactgg ccggactatg     1200
```

-continued

```
ctcatttaac ccccagagag ttagctagtg ctggcctcta ctacacaggg gctgatgatc     1260
aagtgcaatg cttttgttgt gggggaaaac tgaaaaattg ggaaccctgt gatcgtgcct     1320
ggtcagaaca caggagacac tttcccaatt gcttttttgt tttgggccgg aacgttaatg     1380
ttcgaagtga atctggtgtg agttctgata ggaatttccc aaattcaaca aactctccaa     1440
gaaatccagc catggcagaa tatgaagcac ggatcgttac ttttggaaca tggacatcct     1500
cagttaacaa ggagcagctt gcaagagctg gattttatgc tttaggtgaa ggcgataaag     1560
tgaagtgctt ccactgtgga ggagggctca cggattggaa gccaagtgaa gaccctgggg     1620
accagcatgc taagtgctac ccagggtgca ataccctatt ggatgagaag gggcaagaat     1680
atataaataa tattcattta acccatccac ttgaggaatc tttgggaaga actgctgaaa     1740
aaacaccacc gctaactaaa aaaatcgatg ataccatctt ccagaatcct atggtgcaag     1800
aagctatacg aatgggattt agcttcaagg accttaagaa aacaatggaa gaaaaaatcc     1860
aaacatccgg gagcagctat ctatcacttg aggtcctgat tgcagatctt gtgagtgctc     1920
agaaagataa tacggaggat gagtcaagtc aaacttcatt gcagaaagac attagtactg     1980
aagagcagct aaggcgccta caagaggaga agctttccaa aatctgtatg gatagaaata     2040
ttgctatcgt tttttttcct tgtggacatc tggccacttg taaacagtgt gcagaagcag     2100
ttgacaaatg tcccatgtgc tacaccgtca ttacgttcaa ccaaaaaatt tttatgtctt     2160
agtggggcac cacatgttat gttcttcttg ctctaattga atgtgtaatg ggagcgaact     2220
ttaagtaatc ctgcatttgc attccattag catcctgctg tttccaaatg gagaccaatg     2280
ctaacagcac tgtttccgtc taaacattca atttctggat ctttcgagtt atcagctgta     2340
tcatttagcc agtgttttac tcgattgaaa ccttagacag agaagcattt tatagctttt     2400
cacatgtata ttggtagtac actgacttga tttctatatg taagtgaatt catcacctgc     2460
atgtttcatg ccttttgcat aagcttaaca aatggagtgt tctgtataag catggagatg     2520
tgatggaatc tgcccaatga ctttaattgg cttattgtaa acacggaaag aactgcccca     2580
cgctgctggg aggataaaga ttgttttaga tgctcacttc tgtgtttag gattctgccc     2640 atttacttgg aatttattgg agttataatg tacttatatg atatttccga a             2691
```

```
<210> SEQ ID NO 10
<211> LENGTH: 496
<212> TYPE: PRT
<213> ORGANISM: Mus musculus

<400> SEQUENCE: 10
```

```
Met Thr Phe Asn Ser Phe Glu Gly Thr Arg Thr Phe Val Leu Ala Asp
  1               5                  10                  15

Thr Asn Lys Asp Glu Glu Phe Val Glu Glu Phe Asn Arg Leu Lys Thr
             20                  25                  30

Phe Ala Asn Phe Pro Ser Ser Ser Pro Val Ser Ala Ser Thr Leu Ala
         35                  40                  45

Arg Ala Gly Phe Leu Tyr Thr Gly Glu Gly Asp Thr Val Gln Cys Phe
     50                  55                  60

Ser Cys His Ala Ala Ile Asp Arg Trp Gln Tyr Gly Asp Ser Ala Val
 65                  70                  75                  80

Gly Arg His Arg Arg Ile Ser Pro Asn Cys Arg Phe Ile Asn Gly Phe
                 85                  90                  95

Tyr Phe Glu Asn Gly Ala Ala Gln Ser Thr Asn Pro Gly Ile Gln Asn
            100                 105                 110
```

```
Gly Gln Tyr Lys Ser Glu Asn Cys Val Gly Asn Arg Asn Pro Phe Ala
            115                 120                 125
Pro Asp Arg Pro Pro Glu Thr His Ala Asp Tyr Leu Leu Arg Thr Gly
        130                 135                 140
Gln Val Val Asp Ile Ser Asp Thr Ile Tyr Pro Arg Asn Pro Ala Met
145                 150                 155                 160
Cys Ser Glu Glu Ala Arg Leu Lys Ser Phe Gln Asn Trp Pro Asp Tyr
                165                 170                 175
Ala His Leu Thr Pro Arg Glu Leu Ala Ser Ala Gly Leu Tyr Tyr Thr
            180                 185                 190
Gly Ala Asp Asp Gln Val Gln Cys Phe Cys Cys Gly Gly Lys Leu Lys
        195                 200                 205
Asn Trp Glu Pro Cys Asp Arg Ala Trp Ser Glu His Arg Arg His Phe
210                 215                 220
Pro Asn Cys Phe Phe Val Leu Gly Arg Asn Val Asn Val Arg Ser Glu
225                 230                 235                 240
Ser Gly Val Ser Ser Asp Arg Asn Phe Pro Asn Ser Thr Asn Ser Pro
                245                 250                 255
Arg Asn Pro Ala Met Ala Glu Tyr Glu Ala Arg Ile Val Thr Phe Gly
            260                 265                 270
Thr Trp Ile Tyr Ser Val Asn Lys Glu Gln Leu Ala Arg Ala Gly Phe
        275                 280                 285
Tyr Ala Leu Gly Glu Gly Asp Lys Val Lys Cys Phe His Cys Gly Gly
    290                 295                 300
Gly Leu Thr Asp Trp Lys Pro Ser Glu Asp Pro Trp Asp Gln His Ala
305                 310                 315                 320
Lys Cys Tyr Pro Gly Cys Lys Tyr Leu Leu Asp Glu Lys Gly Gln Glu
                325                 330                 335
Tyr Ile Asn Asn Ile His Leu Thr His Pro Leu Glu Glu Ser Leu Gly
            340                 345                 350
Arg Thr Ala Glu Lys Thr Pro Pro Leu Thr Lys Lys Ile Asp Asp Thr
        355                 360                 365
Ile Phe Gln Asn Pro Met Val Gln Glu Ala Ile Arg Met Gly Phe Ser
370                 375                 380
Phe Lys Asp Leu Lys Lys Thr Met Glu Glu Lys Ile Gln Thr Ser Gly
385                 390                 395                 400
Ser Ser Tyr Leu Ser Leu Glu Val Leu Ile Ala Asp Leu Val Ser Ala
                405                 410                 415
Gln Lys Asp Asn Thr Glu Asp Glu Ser Ser Gln Thr Ser Leu Gln Lys
            420                 425                 430
Asp Ile Ser Thr Glu Glu Gln Leu Arg Arg Leu Gln Glu Glu Lys Leu
        435                 440                 445
Ser Lys Ile Cys Met Asp Arg Asn Ile Ala Ile Val Phe Phe Pro Cys
450                 455                 460
Gly His Leu Ala Thr Cys Lys Gln Cys Ala Glu Ala Val Asp Lys Cys
465                 470                 475                 480
Pro Met Cys Tyr Thr Val Ile Thr Phe Asn Gln Lys Ile Phe Met Ser
                485                 490                 495
```

<210> SEQ ID NO 11
<211> LENGTH: 2676
<212> TYPE: DNA
<213> ORGANISM: Mus musculus

<400> SEQUENCE: 11

```
tgggagttcc ccggagccct ggaggaaagc accgcaggtc tgagcagccc tgagccgggc     60
agggtggggg cagtggctaa ggcctagctg gggacgattt aaaggtatcg cgccacccag    120
ccacacccca caggccaggc gagggtgcca ccccggaga tcagaggtca ttgctggcgt    180
tcagagccta ggaagtgggc tgcggtatca gcctagcagt aaaaccgacc agaagccatg    240
cacaaaacta catccccaga gaaagacttg tcccttcccc tccctgtcat ctcaccatga    300
acatggttca agacagcgcc tttctagcca agctgatgaa gagtgctgac acctttgagt    360
tgaagtatga cttttcctgt gagctgtacc gattgtccac gtattcagct tttcccaggg    420
gagttcctgt gtcagaaagg agtctggctc gtgctggctt ttactacact ggtgccaatg    480
acaaggtcaa gtgcttctgc tgtggcctga tgctagacaa ctggaaacaa ggggacagtc    540
ccatggagaa gcacagaaag ttgtaccccca gctgcaactt tgtacagact ttgaatccag    600
ccaacagtct ggaagctagt cctcggcctt ctcttccttc cacggcgatg agcaccatgc    660
ctttgagctt tgcaagttct gagaatactg ctatttcag tggctcttac tcgagctttc    720
cctcagaccc tgtgaacttc cgagcaaatc aagattgtcc tgctttgagc acaagtccct    780
accactttgc aatgaacaca gagaaggcca gattactcac ctatgaaaca tggccattgt    840 ctttttctgtc accagcaaag ctggccaaag caggcttcta ctacatagga cctgagata    900 gagtggcctg ctttgcgtgc gatgggaaac tgagcaactg ggaacgtaag gatgatgcta    960
tgtcagagca ccagaggcat ttccccagct gtccgttctt aaaagacttg ggtcagtctg    1020
cttcgagata cactgtctct aacctgagca tgcagacaca cgcagcccgt attagaacat    1080
tctctaactg gccttctagt gcactagttc attcccagga acttgcaagt gcgggcttt    1140 attatacagg acacagtgat gatgtcaagt gtttttgctg tgatggtggg ctgaggtgct    1200
gggaatctgg agatgacccc tgggtggaac atgccaagtg gtttccaagg tgtgagtact    1260
tgctcagaat caaaggccaa gaatttgtca gccaagttca agctggctat cctcatctac    1320
ttgagcagct attatctacg tcagactccc cagaagatga aatgcagac gcagcaatcg    1380 tgcattttgg ccctggagaa agttcggaag atgtcgtcat gatgagcacg cctgtggtta    1440
aagcagcctt ggaaatgggc ttcagtagga gcctggtgag acagacggtt cagcggcaga    1500
tcctggccac tggtgagaac tacaggaccg tcagtgacct cgttataggc ttactcgatg    1560
cagaagacga gatgagagag gagcagatgg agcaggcggc cgaggaggag gagtcagatg    1620
atctagcact aatccggaag aacaaaatgg tgctttttcca catttgacg tgtgtgacac    1680 caatgctgta ttgcctccta agtgcaaggg ccatcactga acaggagtgc aatgctgtga    1740
aacagaaacc acacacctta caagcaagca cactgattga tactgtgtta gcaaaaggaa    1800
acactgcagc aacctcattc agaaactccc ttcgggaaat tgaccctgcg ttatacagag    1860
atatatttgt gcaacaggac attaggagtc ttcccacaga tgcattgca gctctaccaa    1920 tggaagaaca gttgcggaaa ctccaggagg aaagaatgtg taaagtgtgt atggaccgag    1980
aggtatccat cgtgttcatt ccctgtggcc atctggtcgt gtgcaaagac tgcgctcccc    2040
ctctgaggaa gtgtcccatc tgtagaggga ccatcaaggg cacagtgcgc acatttctct    2100
cctgaacaag actaatggtc catggctgca acttcagcca ggaggaagtt cactgtcact    2160
cccagctcca ttcggaactt gaggccagcc tggatagcac gagacaccgc caaacacaca    2220
aatataaaca tgaaaaactt ttgtctgaag tcaagaatga atgaattact tatataataa    2280
ttttaattgg tttccttaaa agtgctattt gttcccaact cagaaaattg ttttctgtaa    2340
```

-continued

```
acatatttac atactacctg catctaaagt attcatatat tcatatattc agatgtcatg   2400
agagagggtt ttgttcttgt tcctgaaaag cagggattgc ctgcactcct gaaattctca   2460
gaaagattta caatgttggc atttatggtt cagaaactag aatcttctcc cgttgcttta   2520
agaaccggga gcacagatgt ccatgtgttt tatgtataga aattcctgtt atttattgga   2580
tgacatttta gggatatgaa attttttataa agaatttgtg agaaaaagtt aataaagcaa   2640
cataattacc tcttttttttt taaagaaaaa aaaaaa                             2676
```

<210> SEQ ID NO 12
<211> LENGTH: 600
<212> TYPE: PRT
<213> ORGANISM: Mus musculus

<400> SEQUENCE: 12

```
Met Val Gln Asp Ser Ala Phe Leu Ala Lys Leu Met Lys Ser Ala Asp
 1               5                   10                  15

Thr Phe Glu Leu Lys Tyr Asp Phe Ser Cys Glu Leu Tyr Arg Leu Ser
             20                  25                  30

Thr Tyr Ser Ala Phe Pro Arg Gly Val Pro Val Ser Glu Arg Ser Leu
         35                  40                  45

Ala Arg Ala Gly Phe Tyr Tyr Thr Gly Ala Asn Asp Lys Val Lys Cys
     50                  55                  60

Phe Cys Cys Gly Leu Met Leu Asp Asn Trp Lys Gln Gly Asp Ser Pro
 65                  70                  75                  80

Met Glu Lys His Arg Lys Leu Tyr Pro Ser Cys Asn Phe Val Gln Thr
                 85                  90                  95

Leu Asn Pro Ala Asn Ser Leu Glu Ala Ser Pro Arg Pro Ser Leu Pro
            100                 105                 110

Ser Thr Ala Met Ser Thr Met Pro Leu Ser Phe Ala Ser Ser Glu Asn
        115                 120                 125

Thr Gly Tyr Phe Ser Gly Ser Tyr Ser Ser Phe Pro Ser Asp Pro Val
    130                 135                 140

Asn Phe Arg Ala Asn Gln Asp Cys Pro Ala Leu Ser Thr Ser Pro Tyr
145                 150                 155                 160

His Phe Ala Met Asn Thr Glu Lys Ala Arg Leu Leu Thr Tyr Glu Thr
                165                 170                 175

Trp Pro Leu Ser Phe Leu Ser Pro Ala Lys Leu Ala Lys Ala Gly Phe
            180                 185                 190

Tyr Tyr Ile Gly Pro Gly Asp Arg Val Ala Cys Phe Ala Cys Asp Gly
        195                 200                 205

Lys Leu Ser Asn Trp Glu Arg Lys Asp Asp Ala Met Ser Glu His Gln
    210                 215                 220

Arg His Phe Pro Ser Cys Pro Phe Leu Lys Asp Leu Gly Gln Ser Ala
225                 230                 235                 240

Ser Arg Tyr Thr Val Ser Asn Leu Ser Met Gln Thr His Ala Ala Arg
                245                 250                 255

Ile Arg Thr Phe Ser Asn Trp Pro Ser Ser Ala Leu Val His Ser Gln
            260                 265                 270

Glu Leu Ala Ser Ala Gly Phe Tyr Tyr Thr Gly His Ser Asp Asp Val
        275                 280                 285

Lys Cys Phe Cys Cys Asp Gly Gly Leu Arg Cys Trp Glu Ser Gly Asp
    290                 295                 300

Asp Pro Trp Val Glu His Ala Lys Trp Phe Pro Arg Cys Glu Tyr Leu
305                 310                 315                 320
```

```
Leu Arg Ile Lys Gly Gln Glu Phe Val Ser Gln Val Gln Ala Gly Tyr
                325                 330                 335

Pro His Leu Leu Glu Gln Leu Leu Ser Thr Ser Asp Ser Pro Glu Asp
            340                 345                 350

Glu Asn Ala Asp Ala Ala Ile Val His Phe Gly Pro Gly Glu Ser Ser
        355                 360                 365

Glu Asp Val Val Met Met Ser Thr Pro Val Val Lys Ala Ala Leu Glu
    370                 375                 380

Met Gly Phe Ser Arg Ser Leu Val Arg Gln Thr Val Gln Arg Gln Ile
385                 390                 395                 400

Leu Ala Thr Gly Glu Asn Tyr Arg Thr Val Ser Asp Leu Val Ile Gly
                405                 410                 415

Leu Leu Asp Ala Glu Asp Glu Met Arg Glu Glu Gln Met Glu Gln Ala
            420                 425                 430

Ala Glu Glu Glu Ser Asp Asp Leu Ala Leu Ile Arg Lys Asn Lys
        435                 440                 445

Met Val Leu Phe Gln His Leu Thr Cys Val Thr Pro Met Leu Tyr Cys
    450                 455                 460

Leu Leu Ser Ala Arg Ala Ile Thr Glu Gln Glu Cys Asn Ala Val Lys
465                 470                 475                 480

Gln Lys Pro His Thr Leu Gln Ala Ser Thr Leu Ile Asp Thr Val Leu
                485                 490                 495

Ala Lys Gly Asn Thr Ala Ala Thr Ser Phe Arg Asn Ser Leu Arg Glu
            500                 505                 510

Ile Asp Pro Ala Leu Tyr Arg Asp Ile Phe Val Gln Gln Asp Ile Arg
        515                 520                 525

Ser Leu Pro Thr Asp Asp Ile Ala Ala Leu Pro Met Glu Glu Gln Leu
    530                 535                 540

Arg Lys Leu Gln Glu Glu Arg Met Cys Lys Val Cys Met Asp Arg Glu
545                 550                 555                 560

Val Ser Ile Val Phe Ile Pro Cys Gly His Leu Val Val Cys Lys Asp
                565                 570                 575

Cys Ala Pro Ser Leu Arg Lys Cys Pro Ile Cys Arg Gly Thr Ile Lys
            580                 585                 590

Gly Thr Val Arg Thr Phe Leu Ser
        595                 600

<210> SEQ ID NO 13
<211> LENGTH: 3151
<212> TYPE: DNA
<213> ORGANISM: Mus musculus

<400> SEQUENCE: 13
agttatataa aatacgaagt tttcaaaaag aaggctagtg caacagaaaa gctttgctaa      60
aacagattct tagttatttg aggtaacaaa agaaagccat gtcttgaatt gattcgttct     120
taattataac agactatag tggaaagggc cttaaacaca ggcggacttt ataaaatgca      180
gtcttaggtt tatgtgcaaa atactgtctg ttgaccagat gtattcacat gatatataca     240
gagtcaaggt ggtgatatag aagatttaac agtgagggag ttaacagtct gtgctttaag     300
cgcagttcct ttacagtgaa tactgtagtc ttaatagacc tgagctgact gctgcagttg     360
atgtaaccca cttagagaaa tactgtatga catcttctct aaggaaaacc agctgcagac     420
ttcactcagt tcctttcatt tcataggaaa aggagtagtt cagatgtcat gtttaagtcc     480
```

-continued

```
ttataaggga aaagagcctg aatatatgcc ctagtaccta ggcttcataa ctagtaataa    540
gaagttagtt atgggtaaat agatctcagg ttacccagaa gagttcatgt gaccccaaa     600 gagtcctaac tagtgtcttg gcaagtgaga cagatttgtc ctgtgagggt gtcaattcac    660
cagtccaagc agaagacaat gaatctatcc agtcaggtgt ctgtggtgga gatctagtgt    720
ccaagtggtg agaaacttca tctggaagtt taagcggtca gaaatactat tactactcat    780
ggacaaaact gtctcccaga gactcggcca aggtacctta caccaaaaac ttaaacgtat    840
aatggagaag agcacaatct tgtcaaattg gacaaggag agcgaagaaa aaatgaagtt     900
tgacttttcg tgtgaactct accgaatgtc tacatattca gcttttccca ggggagttcc    960
tgtctcagag aggagtctgg ctcgtgctgg cttttattat acaggtgtga atgacaaagt   1020
caagtgcttc tgctgtggcc tgatgttgga taactggaaa caaggggaca gtcctgttga   1080
aaagcacaga cagttctatc ccagctgcag cttttgtacag actctgcttt cagccagtct  1140
gcagtctcca tctaagaata tgtctcctgt gaaaagtaga tttgcacatt cgtcacctct   1200
ggaacgaggt ggcattcact ccaacctgtg ctctagccct cttaattcta gagcagtgga   1260
agacttctca tcaaggatgg atccctgcag ctatgccatg agtacagaag aggccagatt   1320
tcttacttac agtatgtggc ctttaagttt tctgtcacca gcagagctgg ccagagctgg   1380
cttctattac ataggcctg gagacagggt ggcctgtttt gcctgtggtg ggaaactgag    1440
caactgggaa ccaaaggatg atgctatgtc agagcaccgc agacattttc cccactgtcc   1500
atttctggaa aatacttcag aaacacagag gtttagtata tcaaatctaa gtatgcagac   1560
acactctgct cgattgagga catttctgta ctggccacct agtgttcctg ttcagcccga   1620
gcagcttgca agtgctggat tctattacgt ggatcgcaat gatgatgtca agtgcttttg   1680
ttgtgatggt ggcttgagat gttgggaacc tggagatgac ccctggatag aacacgccaa   1740
atggtttcca agtgtgagt tcttgatacg gatgaagggt caggagtttg ttgatgagat    1800
tcaagctaga tatcctcatc ttcttgagca gctgttgtcc acttcagaca ccccaggaga   1860
agaaaatgct gaccctacag agacagtggt gcatttggc cctggagaaa gttcgaaaga    1920
tgtcgtcatg atgagcacgc ctgtggttaa agcagccttg gaaatgggct tcagtaggag   1980
cctggtgaga cagacggttc agcggcagat cctggccact ggtgagaact acaggaccgt   2040
caatgatatt gtctcagtac ttttgaatgc tgaagatgag agaagagaag aggagaagga   2100
aagacagact gaagagatgg catcaggtga cttatcactg attcggaaga atagaatggc   2160
cctctttcaa cagttgacac atgtccttcc tatcctggat aatcttcttg aggccagtgt   2220
aattacaaaa caggaacatg atattattag acagaaaaca cagataccct acaagcaag    2280 agagcttatt gacaccgttt tagtcaaggg aaatgctgca gccaacatct tcaaaaactc   2340
tctgaaggaa attgactcca cgttatatga aaacttattt gtggaaaaga atatgaagta   2400
tattccaaca gaagacgttt caggcttgtc attggaagag cagttgcgga gattacaaga   2460
agaacgaact tgcaaagtgt gtatggacag agaggtttct attgtgttca ttccgtgtgg   2520
tcatctagta gtctgccagg aatgtgcccc ttctctaagg aagtgcccca tctgcagggg   2580
gacaatcaag gggactgtgc gcacatttct ctcatgagtg aagaatggtc tgaaagtatt   2640
gttggacatc agaagctgtc agaacaaaga atgaactact gatttcagct cttcagcagg   2700
acattctact ctcttttcaag attagtaatc ttgctttatg aagggtagca ttgtatattt   2760
aagcttagtc tgttgcaagg gaaggtctat gctgttgagc tacaggactg tgtctgttcc   2820
agagcaggag ttgggatgct tgctgtatgt ccttcaggac ttcttggatt tggaatttgt   2880
```

```
gaaagctttg gattcaggtg atgtggagct cagaaatcct gaaaccagtg gctctggtac    2940
tcagtagtta gggtaccctg tgcttcttgg tgcttttcct ttctggaaaa taaggatttt    3000
tctgctactg gtaaatattt tctgtttgtg agaaatatat taaagtgttt cttttaaagg    3060
cgtgcatcat tgtagtgtgt gcagggatgt atgcaggcaa acactgtgt ataataaa      3120 taaatctttt taaaaagtgt aaaaaaaaaa a                                   3151
```

<210> SEQ ID NO 14
<211> LENGTH: 612
<212> TYPE: PRT
<213> ORGANISM: Mus musculus

<400> SEQUENCE: 14

```
Met Asp Lys Thr Val Ser Gln Arg Leu Gly Gln Gly Thr Leu His Gln
  1               5                  10                  15

Lys Leu Lys Arg Ile Met Glu Lys Ser Thr Ile Leu Ser Asn Trp Thr
             20                  25                  30

Lys Glu Ser Glu Glu Lys Met Lys Phe Asp Phe Ser Cys Glu Leu Tyr
         35                  40                  45

Arg Met Ser Thr Tyr Ser Ala Phe Pro Arg Gly Val Pro Val Ser Glu
     50                  55                  60

Arg Ser Leu Ala Arg Ala Gly Phe Tyr Tyr Thr Gly Val Asn Asp Lys
 65                  70                  75                  80

Val Lys Cys Phe Cys Cys Gly Leu Met Leu Asp Asn Trp Lys Gln Gly
                 85                  90                  95

Asp Ser Pro Val Glu Lys His Arg Gln Phe Tyr Pro Ser Cys Ser Phe
            100                 105                 110

Val Gln Thr Leu Leu Ser Ala Ser Leu Gln Ser Pro Ser Lys Asn Met
        115                 120                 125

Ser Pro Val Lys Ser Arg Phe Ala His Ser Ser Pro Leu Glu Arg Gly
    130                 135                 140

Gly Ile His Ser Asn Leu Cys Ser Ser Pro Leu Asn Ser Arg Ala Val
145                 150                 155                 160

Glu Asp Phe Ser Ser Arg Met Asp Pro Cys Ser Tyr Ala Met Ser Thr
                165                 170                 175

Glu Glu Ala Arg Phe Leu Thr Tyr Ser Met Trp Pro Leu Ser Phe Leu
            180                 185                 190

Ser Pro Ala Glu Leu Ala Arg Ala Gly Phe Tyr Tyr Ile Gly Pro Gly
        195                 200                 205

Asp Arg Val Ala Cys Phe Ala Cys Gly Gly Lys Leu Ser Asn Trp Glu
    210                 215                 220

Pro Lys Asp Asp Ala Met Ser Glu His Arg Arg His Phe Pro His Cys
225                 230                 235                 240

Pro Phe Leu Glu Asn Thr Ser Glu Thr Gln Arg Phe Ser Ile Ser Asn
                245                 250                 255

Leu Ser Met Gln Thr His Ser Ala Arg Leu Arg Thr Phe Leu Tyr Trp
            260                 265                 270

Pro Pro Ser Val Pro Val Gln Pro Glu Gln Leu Ala Ser Ala Gly Phe
        275                 280                 285

Tyr Tyr Val Asp Arg Asn Asp Asp Val Lys Cys Phe Cys Cys Asp Gly
    290                 295                 300

Gly Leu Arg Cys Trp Glu Pro Gly Asp Asp Pro Trp Ile Glu His Ala
305                 310                 315                 320
```

Lys Trp Phe Pro Arg Cys Glu Phe Leu Ile Arg Met Lys Gly Gln Glu
            325                 330                 335

Phe Val Asp Glu Ile Gln Ala Arg Tyr Pro His Leu Leu Glu Gln Leu
            340                 345                 350

Leu Ser Thr Ser Asp Thr Pro Gly Glu Glu Asn Ala Asp Pro Thr Glu
            355                 360                 365

Thr Val Val His Phe Gly Pro Gly Glu Ser Ser Lys Asp Val Val Met
            370                 375                 380

Met Ser Thr Pro Val Val Lys Ala Ala Leu Glu Met Gly Phe Ser Arg
385                 390                 395                 400

Ser Leu Val Arg Gln Thr Val Gln Arg Gln Ile Leu Ala Thr Gly Glu
            405                 410                 415

Asn Tyr Arg Thr Val Asn Asp Ile Val Ser Val Leu Leu Asn Ala Glu
            420                 425                 430

Asp Glu Arg Arg Glu Glu Glu Lys Glu Arg Gln Thr Glu Glu Met Ala
            435                 440                 445

Ser Gly Asp Leu Ser Leu Ile Arg Lys Asn Arg Met Ala Leu Phe Gln
            450                 455                 460

Gln Leu Thr His Val Leu Pro Ile Leu Asp Asn Leu Leu Glu Ala Ser
465                 470                 475                 480

Val Ile Thr Lys Gln Glu His Asp Ile Ile Arg Gln Lys Thr Gln Ile
            485                 490                 495

Pro Leu Gln Ala Arg Glu Leu Ile Asp Thr Val Leu Val Lys Gly Asn
            500                 505                 510

Ala Ala Ala Asn Ile Phe Lys Asn Ser Leu Lys Glu Ile Asp Ser Thr
            515                 520                 525

Leu Tyr Glu Asn Leu Phe Val Glu Lys Asn Met Lys Tyr Ile Pro Thr
            530                 535                 540

Glu Asp Val Ser Gly Leu Ser Leu Glu Glu Gln Leu Arg Arg Leu Gln
545                 550                 555                 560

Glu Glu Arg Thr Cys Lys Val Cys Met Asp Arg Glu Val Ser Ile Val
            565                 570                 575

Phe Ile Pro Cys Gly His Leu Val Cys Gln Glu Cys Ala Pro Ser
            580                 585                 590

Leu Arg Lys Cys Pro Ile Cys Arg Gly Thr Ile Lys Gly Thr Val Arg
            595                 600                 605

Thr Phe Leu Ser
      610

<210> SEQ ID NO 15
<211> LENGTH: 21
<212> TYPE: DNA
<213> ORGANISM: Artificial Sequence
<220> FEATURE:
<223> OTHER INFORMATION: Based on Homo sapiens sequence

<400> SEQUENCE: 15
agtgcgggtt tttattatgt g                                          21

<210> SEQ ID NO 16
<211> LENGTH: 25
<212> TYPE: DNA
<213> ORGANISM: Artificial Sequence
<220> FEATURE:
<223> OTHER INFORMATION: Based on Homo sapiens sequence

<400> SEQUENCE: 16

```
agatgaccac aaggaataaa cacta                                          25

<210> SEQ ID NO 17
<211> LENGTH: 11
<212> TYPE: PRT
<213> ORGANISM: Artificial Sequence
<220> FEATURE:
<223> OTHER INFORMATION: Based on Homo sapiens sequence

<400> SEQUENCE: 17

Met Gln Lys Leu Ile Ser Glu Glu Asp Leu
1               5                   10
```

DETECTION AND MODULATION OF IAPS FOR THE DIAGNOSIS AND TREATMENT OF PROLIFERATIVE DISEASE

CROSS REFERENCE TO RELATED APPLICATIONS

This application is a divisional of Ser. No. 08/800,929, filed Feb. 13, 1997, which is a utility application claiming priority from provisional application 60/030,590, filed Nov. 14, 1996, and provisional application 60/017,354, filed Apr. 26, 1996.

BACKGROUND OF THE INVENTION

The invention relates to the diagnosis and treatment of cancer.

One way by which cells die is referred to as apoptosis, or programmed cell death. Apoptosis often occurs as a normal part of the development and maintenance of healthy tissues. The process occurs so rapidly that it is difficult to detect. This may help to explain why the involvement of apoptosis in a wide spectrum of biological processes has only recently been recognized.

The apoptosis pathway is now known to play a critical role in embryonic development, viral pathogenesis, cancer, autoimmune disorders, and neurodegenerative disease. The failure of an apoptotic response has been implicated in the development of cancer, autoimmune disorders, such as lupus erythematosis and multiple sclerosis, and in viral infections, including those associated with herpes virus, poxvirus, and adenovirus.

Baculoviruses encode proteins that are termed inhibitors of apoptosis proteins (IAPs) because they inhibit the apoptosis that would otherwise occur when insect cells are infected by the virus. These proteins are thought to work in a manner that is independent of other viral proteins. The baculovirus IAP genes include sequences encoding a ring zinc finger-like motif (RZF), which is presumed to be directly involved in DNA binding, and two N-terminal domains that consist of a 70 amino acid repeat motif termed a BIR domain (Baculovirus IAP Repeat).

The role of apoptosis in cancer has only recently been appreciated. The identification of growth-promoting "oncogenes" in the late 1970's gave rise to an almost universal focus on cellular proliferation that dominated research in cancer biology for many years. Long-standing dogma held that anti-cancer therapies preferentially targeted rapidly dividing cancer cells relative to "normal" cells. This explanation was not entirely satisfactory, since some slow growing tumors are easily treated, while many rapidly dividing tumor types are extremely resistant to anti-cancer therapies. Progress in the cancer field has now led to a new paradigm in cancer biology wherein neoplasia is viewed as a failure to execute normal pathways of programmed cell death. Normal cells receive continuous feedback from their neighbors through various growth factors, and commit "suicide" if removed from this context. Cancer cells somehow ignore these commands and continue inappropriate proliferation. Cancer therapies, including radiation and many chemotherapies, have traditionally been viewed as causing overwhelming cellular injury. New evidence suggests that cancer therapies actually work by triggering apoptosis.

Both normal cell types and cancer cell types display a wide range of susceptibility to apoptotic triggers, although the determinants of this resistance are only now under investigation. Many normal cell types undergo temporary growth arrest in response to a sub-lethal dose of radiation or cytotoxic chemical, while cancer cells in the vicinity undergo apoptosis. This provides the crucial treatment "window" of appropriate toxicity that allows successful anti-cancer therapy. It is therefore not surprising that resistance of tumor cells to apoptosis is emerging as a major category of cancer treatment failure.

Compared to the numerous growth promoting oncogenes identified to date (>100) relatively few genes have been isolated that regulate apoptosis. The bcl-2 gene was first identified as an oncogene associated with the development of follicular lymphomas. In contrast to all other oncogenes identified to date, bcl-2 displays no ability to promote cell proliferation, and instead has been demonstrated to suppress apoptosis by a variety of triggers. Elevated bcl-2 expression is associated with a poor prognosis in neuroblastoma, prostate and colon cancer, and can result in a multidrug resistance phenotype in vitro. Although the study of bcl-2 has helped revolutionize cancer paradigms, the vast majority of human malignancies do not demonstrate aberrant bcl-2 expression.

In contrast to the findings with bcl-2, mutation of the p53 tumor suppresser gene has been estimated to occur in up to 50% of human cancers and is the most frequent genetic change associated with cancer to date. The p53 protein plays a crucial role in surveying the genome for DNA damage. The cell type and degree of damage determines whether the cell will undergo growth arrest and repair, or initiate apoptosis. Mutations in p53 interfere with this activity, rendering the cell resistant to apoptosis by a wide range of cellular insults. Some progress has been made in understanding the molecular biology of p53, but many questions remain. p53 is known to function as a transcription factor, with the ability to positively or negatively regulate the expression of a variety of genes involved in cell cycle control, DNA repair, and apoptosis (including the anti-apoptotic bcl-2 gene described above and the related pro-apoptotic gene bax). The drug resistant phenotype conferred by p53 alterations has been linked to bcl-2/bax regulation, but this correlation does not hold for most cancer types, leaving open the possibility that other critical genes regulated by p53 remain to be identified.

SUMMARY OF THE INVENTION

We have discovered that IAP and Naip overexpression are associated with a wide range of cancer types including ovarian cancer, adenocarcinoma, lymphoma, and pancreatic cancer. In addition, we have found that nuclear localization fragmentation of the IAPs, and overexpression of the IAPs in the presence of p53 mutations correlate with a cancer diagnosis, a poor prognosis, and resistance to numerous chemotherapeutic cancer drugs. These discoveries provide diagnostic, prognostic, and therapeutic compounds and methods for the detection and treatment of proliferative diseases.

In the first aspect, the invention features a method of detecting cancer or an increased likelihood of cancer by detecting an increase in IAP gene expression or protein expression in a cell from the mammal. In various embodiments, the detection may be performed by contacting with IAP or naip nucleic acid, or a portion thereof (which is greater than 9 nucleotides, and preferably greater than 18 nucleotides in length), with a preparation of nucleic acid from the cell; detecting levels of IAP or naip nucleic acid using quantitative nucleic acid amplification techniques; monitoring the levels of IAP or Naip protein; or monitoring the levels of IAP or Naip biological activity. Preferably, the cell is a cell from a mammal suspected of having a leukemia, a lymphoma, breast cancer, pancreatic cancer, melanoma, lung cancer, or ovarian cancer.

In one embodiment utilizing nucleic acid amplification for detection, the invention features characterization of a cellular IAP or naip nucleic acid content and levels by: (a) providing a sample of nucleic acid; (b) providing a pair of oligonucleotides having sequence homology to an IAP or naip nucleic acid; (c) combining the pair of oligonucleotides with the cellular sample under conditions suitable for polymerase chain reaction-mediated nucleic acid amplification; and (d) isolating the amplified IAP nucleic acid or fragment thereof. The isolated nucleic acid may then be quantitated, sequenced, or otherwise characterized for the activity it imparts on the cell or related cells. In preferred embodiments, the amplification is carried out using a reverse-transcription polymerase chain reaction, for example, the RACE method.

In one embodiment using nucleic acid hybridization for detection, the invention features use of IAP or naip nucleic acid isolated according to the method involving: (a) providing a preparation of nucleic acid; (b) providing a detectably labelled nucleotide sequence having homology to a region of an IAP or naip nucleic acid; (c) contacting the preparation of nucleic acid with the detectably-labelled nucleic acid sequence under hybridization conditions providing detection of nucleic acid having 50% or greater nucleotide sequence identity; and (d) identifying and characterizing IAP or naip nucleic acid by their association with the detectable label.

In one embodiment utilizing antibodies for detection, the invention features methods for using a purified antibody that binds specifically to an IAP or Naip family of proteins. Such an antibody may be used for diagnosis and also for drug screens, prognostic methods, and treatment methods described herein. Any standard immunodetection method may be employed, as appropriate. Preferably, the antibody binds specifically to Xiap, Hiap-1, Hiap-2 or Naip. In various embodiments, the antibody may react with other IAP polypeptides or may be specific for one or a few IAP polypeptides. The antibody may be a monoclonal or a polyclonal antibody. Preferably, the antibody reacts specifically with only one of the IAP polypeptides, for example, reacts with murine and human xiap, but not with hiap-1 or hiap-2 from other mammalian species. In any of the immunodetection, diagnostic and prognostic methods an increase in IAP or Naip polypeptide levels or an increase in the level of certain IAP or Naip fragments described herein (e.g., BIR-containing fragments or nuclear polypeptides, found to be associated with proliferation indicate a cancer diagnosis or a poor cancer prognosis when therapeutics which act by enhancing apoptosis are used for treatment).

In another aspect, the invention features a IAP or naip gene nucleic acid fragment or antisense RNA sequence for use in suppressing cell proliferation. Such nucleic acids of the invention and methods for using them may be identified according to a method involving: (a) providing a cell sample; (b) introducing by transformation into the cell sample a candidate IAP or naip nucleic acid; (c) expressing the candidate IAP or naip nucleic acid within the cell sample; and (d) determining whether the cell sample exhibits an altered apoptotic response, whereby decreased apoptosis identifies an anti-proliferative compound. Preferably, the cell is a cancer cell.

In another aspect, the invention features a method of determining the prognosis of a mammal having a proliferative disease. The method includes detecting levels of [AP or NAIP nucleic acids, protein levels, or biological activity, or IAP fragments in the cell suspected to be involved in a proliferative disease. In various embodiments, the methods of detection described above for diagnosis may be employed. An increase in IAP or NAIP levels indicates a proliferative disease (i.e., an increased likelihood the cancers described herein) and, particularly if a p53 mutation is present, a poor prognosis for therapeutic approaches which rely on enhancing apoptosis. The presence of IAP fragments of less than 64 kDa, more preferably less than 45 kDa, indicates an increased likelihood that the cancer will be resistant to chemotherapeutics which act by inducing apoptosis.

In preferred embodiments of the diagnostic and prognostic methods, the levels being monitored are levels of IAP or NAIP expression or activity levels known to be associated with cancer suspected or diagnosed. Most preferably, the disease is selected from the group consisting of a breast cancer (preferably using a hiap-2, hiap-1, Hiap-2, or Hiap-1 probes), ovarian cancer (preferably using a hiap-2, or Hiap-2 probes), promyelocytic leukemia, a HeLa-type carcinoma, chronic myelogenous leukemia (preferably using xiap, hiap-2, Xiap or Hiap-2 probes), lymphoblastic leukemia (preferably using a xiap or Xiap probes), Burkitt's lymphoma (preferably using an hiap-1 or Hiap-1 probes), colorectal adenocarcinoma, lung carcinoma, and melanoma (preferably using a xiap, or Xiap probes). Preferably, a cancer diagnosis or poor prognosis is indicated by a 2-fold increase in expression or activity, more preferably, at least a 10-fold increase in expression or activity in the cell being tested.

In another aspect, the invention features a method of identifying a compound that inhibits cancer by enhancing apoptosis. The method includes providing a cell expressing an IAP or Naip polypeptide and being capable of proliferation or viability in culture, contacting the cell with a candidate compound, and monitoring the expression of an IAP gene, naip gene, a reporter linked to IAP or naip regulatory sequence, levels of IAP or Naip polypeptides, cleavage of IAP polypeptides, and/or nuclear versus cytoplasmic localization of IAP or Naip polypeptides. A decrease in the level of expression of the IAP or naip gene, IAP or Naip protein characteristics, IAP or Naip biological activity, IAP cleavage, or localization of protein to the nucleus, indicate the presence of a compound which enhances apoptosis, as described herein. In various preferred embodiments, the cell used in the method is a fibroblast, a neuronal cell, a glial cell, a lymphocyte (T cell or B cell), a breast cancer cell, a lymphoma cell, an ovarian cancer cell, a leukemia cell, a pancreatic cancer cell, a melanoma cell, or an insect cell; the preferred polypeptide expression being monitored is Xiap, Hiap-1, Hiap-2, or Naip (i.e., human or murine). In the embodiment utilizing fragment detection, the fragment is preferably less than 64 kDa, more preferably less than 45 kDa. All the detection methods described herein may be employed, as appropriate.

In a related aspect, the invention features methods of detecting compounds that enhance apoptosis using the interaction trap technology and IAP or Naip polypeptides, or fragments thereof, as a component of the bait. In preferred embodiments, the compound being tested as an enhancer of apoptosis is also a polypeptide.

In another aspect, the invention features a method of treating a patient diagnosed with a proliferative disease. In the method, apoptosis may be induced in a cell to control a proliferative disease either alone or in combination with other therapies by administering to the cell a negative regulator of the IAP-dependent or NAIP anti-apoptotic pathway. The negative regulator may be, but is not limited to, an IAP ring zinc finger, and an IAP polypeptide that includes a ring zinc finger and lacks at least one BIR domain. Alternatively, apoptosis may be induced in the cell by administering a nucleic acid encoding an IAP antisense RNA molecule administered directly or via gene therapy(see U.S. Pat. No. 5,576,208 for general parameters which may be applicable in the selection of IAP or naip antisense RNAs). In yet another method, the negative regulator may be a purified antibody, or a fragment thereof, that binds specifically to an IAP polypeptide. For example, in one preferred embodiment, the antibody may bind to an approximately 26 kDa cleavage product of an IAP polypeptide that includes at least one BIR domain but lacks a ring zinc finger domain.

In two additional aspects, the invention features a transgenic animal and methods of using the mammal for detection of anti-cancer therapeutics. Preferably the mammal overexpresses an IAP or Naip polypeptide and/or expresses a naip or IAP antisense RNA or IAP or Naip fragment. In one embodiment, the animal also has a genetic predisposition to cancer or has cancer cells under conditions which provide for proliferation absent the transgenic construct encoding either the antisense RNA or fragment.

By "IAP gene" is meant a gene encoding a polypeptide having at least one BIR domain and a ring zinc finger domain which is capable of modulating (inhibiting or enhancing) apoptosis in a cell or tissue when provided by other intracellular or extracellular delivery methods (see, e.g., the U.S. Ser. Nos. 08/511,485, 08/576,965, and PCT/IB96/01022). In preferred embodiments the IAP gene is a gene having about 50% or greater nucleotide sequence identity to at least one of the IAP amino acid encoding sequences of FIGS. 1–4 or portions thereof. Preferably, the region of sequence over which identity is measured is a region encoding at least one BIR domain and a ring zinc finger domain. Mammalian IAP genes include nucleotide sequences isolated from any mammalian source. Preferably, the mammal is a human. The term "IAP gene" is meant to encompass any member of the family of genes that encode inhibitors of apoptosis. An IAP gene may encode a polypeptide that has at least 20%, preferably at least 30%, and ost preferably at least 50% amino acid sequence identity with at least one of the conserved regions of one of the IAP members described herein (i.e., either the BIR or ring zinc finger domains from the human or murine xiap, hiap-1 and hiap-2). Representative members of the IAP gene family include, without limitation, the human and murine xiap, hiap-1, and hiap-2 genes.

By "IAP protein" or "IAP polypeptide" is meant a polypeptide, or fragment thereof, encoded by an IAP gene.

"naip gene" and "Naip polypeptide" means the naip genes, fragments thereof, and polypeptides encoded by the same described in UK9601108.5 filed Jan. 19, 1996 and the PCT application claiming priority from UK9601108.5 filed Jan. 17, 1997.

By "BIR domain" is meant a domain having the amino acid sequence of the consensus sequence: Xaal-Xaal-Xaal-Arg-Leu-Xaal-Thr-Phe-Xaal-Xaal-Trp-Pro-Xaa2-Xaal-Xaal-Xaa2-Xaa2-Xaal-Xaal-Xaal-Xaal-Leu-Ala-Xaal-Ala-Gly-Phe-Tyr-Tyr-Xaal-Gly-Xaal-Xaal-Asp-Xaal-Val-Xaal-Cys-Phe-Xaal-Cys-Xaal-Xaal-Xaal-Xaal-Xaal-Xaal-Trp-Xaal-Xaal-Xaal-Asp-Xaal-Xaal-Xaal-Xaal-Xaal-His-Xaal-Xaal-Xaal-Xaal-Pro-Xaal-Cys-Xaal-Phe-Val, wherein Xaal is any amino acid and Xaa2 is any amino acid or is absent (SEQ ID NO:2). Preferably, the sequence is substantially identical to one of the BIR domain sequences provided for xiap, hiap-1, hiap-2 herein.

By "ring zinc finger" or "RZF" is meant a domain having the amino acid sequence of the consensus sequence: Glu-Xaal-Xaal-Xaal-Xaal-Xaal-Xaal- Xaa2-Xaal-Xaal-Xaal-Cys-Lys-Xaa3-Cys-Met-Xaal-Xaal-Xaal-Xaal-Xaal-Xaa3-Xaal-Phe-Xaal-Pro-Cys-Gly-His-Xaal-Xaal-Xaal-Cys-Xaal-Xaal-Cys-Ala- Xaal-Xaal-Xaal-Xaal-Xaal-Cys-Pro-Xaal-Cys, wherein Xaal is any amino acid, Xaa2 is Glu or Asp, and Xaa3 is Val or Ile (SEQ ID NO:1).

Preferably, the sequence is substantially identical to the RZF domains provided herein for the human or murine Xiap, Hiap- 1, or Hiap-2.

By "enhancing apoptosis" is meant increasing the number of cells which apoptose in a given cell population. Preferably, the cell population is selected from a group including ovarian cancer cells, breast cancer cells, pancreatic cancer cells, T cells, neuronal cells, fibroblasts, or any other cell line known to proliferate in a laboratory setting. It will be appreciated that the degree of apoptosis enhancement provided by an apoptosis enhancing compound in a given assay will vary, but that one skilled in the art can determine the statistically significant change in the level of apoptosis which identifies a compound which enhances apoptosis otherwise limited by an ]AP. Preferably, "enhancing apoptosis" means that the increase in the number of cells undergoing apoptosis is at least 25%, more preferably the increase is 50%, and most preferably the increase is at least one-fold. Preferably, the sample monitored is a sample of cells which normally undergo insufficient apoptosis (i.e., cancer cells).

By "proliferative disease" is meant a disease which is caused by or results in inappropriately high levels of cell division, inappropriately low levels of apoptosis, or both. For example, cancers such as lymphoma, leukemia, melanoma, ovarian cancer, breast cancer, pancreatic cancer, and lung cancer are all examples of proliferative disease.

By "polypeptide" is meant any chain of more than two amino acids, regardless of post-translational modification such as glycosylation or phosphorylation.

By "IAP or Naip biological activity" is meant any activity known to be caused in vivo or in vitro by a Naip or IAP polypeptide.

By "substantially identical" is meant a polypeptide or nucleic acid exhibiting at least 50%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

By "substantially pure polypeptide" is meant a polypeptide that has been separated from the components that naturally accompany it. Typically, the polypeptide is substantially pure when it is at least 60%, by weight, free from the proteins and naturally-occurring organic molecules with which it is naturally associated. Preferably, the polypeptide is an IAP polypeptide that is at least 75%, more preferably at least 90%, and most preferably at least 99%, by weight, pure. A substantially pure IAP polypeptide may be obtained, for example, by extraction from a natural source (e.g. a fibroblast, neuronal cell, or lymphocyte) by expression of a recombinant nucleic acid encoding an IAP polypeptide, or by chemically synthesizing the protein. Purity can be measured by any appropriate method, e.g., by column chromatography, polyacrylamide gel electrophoresis, or HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eukaryotic organisms but synthesized in E. Coli or other prokaryotes.

By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

By "transformed cell" is meant a cell into which (or into an ancestor of which) has been introduced, by means of recombinant DNA techniques, a DNA molecule encoding (as used herein) an IAP polypeptide.

By "transgene" is meant any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

By "transgenic" is meant any cell which includes a DNA sequence which is inserted by artifice into a cell and becomes part of the genome of the organism which develops from that cell. As used herein, the transgenic organisms are generally transgenic mammalian (e.g., rodents such as rats or mice) and the DNA (transgene) is inserted by artifice into the nuclear genome.

By "transformation" is meant any method for introducing foreign molecules into a cell. Lipofection, calcium phosphate precipitation, retroviral delivery, electroporation, and biolistic transformation are just a few of the teachings which may be used. For example, biolistic transformation is a method for introducing foreign molecules into a cell using velocity driven microprojectiles such as tungsten or gold particles. Such velocity-driven methods originate from pressure bursts which include, but are not limited to, helium-driven, air-driven, and gunpowder-driven techniques. Biolistic transformation may be applied to the transformation or transfection of a wide variety of cell types and intact tissues including, without limitation, intracellular organelles (e.g., and mitochondria and chloroplasts), bacteria, yeast, fungi, algae, animal tissue, and cultured cells.

By "positioned for expression" is meant that the DNA molecule is positioned adjacent to a DNA sequence which directs transcription and translation of the sequence (i.e., facilitates the production of, e.g., an IAP polypeptide, a recombinant protein or a RNA molecule).

By "reporter gene" is meant a gene whose expression may be assayed; such genes encode proteins including, without limitation, glucuronidase (GUS), luciferase, chloramphenicol transacetylase (CAT), and β-galactosidase.

By "promoter" is meant minimal sequence sufficient to direct transcription. Also included in the invention are those promoter elements which are sufficient to render promoter-dependent gene expression controllable for cell type-specific, tissue-specific or inducible by external signals or agents; such elements may be located in the 5' or 3' regions of the native gene.

By "operably linked" is meant that a gene and one or more regulatory sequences are connected in such a way as to permit gene expression when the appropriate molecules (e.g., transcriptional activator proteins are bound to the regulatory sequences).

By "conserved region" is meant any stretch of six or more contiguous amino acids exhibiting at least 30%, preferably 50%, and most preferably 70% amino acid sequence identity between two or more of the IAP family members, (e.g., between human HIAP-1, HIAP-2, and XIAP). Examples of preferred conserved regions are shown (as boxed or designated sequences) in FIGS. 5–7 and Tables 1 and 2, and include, without limitation, BIR domains and ring zinc finger domains.

By "detectably-labelled" is meant any means for marking and identifying the presence of a molecule, e.g., an oligonucleotide probe or primer, a gene or fragment thereof, or a cDNA molecule. Methods for detectably-labelling a molecule are well known in the art and include, without limitation, radioactive labelling (e.g., with an isotope such as $^{32}P$ or $^{35}S$) and nonradioactive labelling (e.g., chemiluminescent labelling, e.g., fluorescein labelling).

By "antisense," as used herein in reference to nucleic acids, is meant a nucleic acid sequence, regardless of length, that is complementary to the coding strand of an IAP or naip gene. Preferably, the antisense nucleic acid is capable of enhancing apoptosis when present in a cell which normally does not undergo sufficient apoptosis. Preferably, the increase is at least 10%, relative to a control, more preferably 25%, and most preferably 1-fold or more.

By "purified antibody" is meant antibody which is at least 60%, by weight, free from proteins and naturally occurring organic molecules with which it is naturally associated. Preferably, the preparation is at least 75%, more preferably 90%, and most preferably at least 99%, by weight, antibody, e.g., an IAP specific antibody. A purified antibody may be obtained, for example, by affinity chromatography using recombinantly-produced protein or conserved motif peptides and standard techniques.

By "specifically binds" is meant an antibody that recognizes and binds a protein but that does not substantially recognize and bind other molecules in a sample, e.g., a biological sample, that naturally includes protein.

Other features and advantages of the invention will be apparent from the following description of the preferred embodiments thereof, and from the claims.

BRIEF DESCRIPTION OF THE DRAWINGS

FIG. 1 is the human xiap cDNA sequence (SEQ ID NO:3) and the Xiap polypeptide sequence (SEQ ID NO:4).

FIG. 2 is the human hiap-1 cDNA sequence (SEQ ID NO:5) and the Hiap-1 polypeptide sequence (SEQ ID NO:6).

FIG. 3 is the human hiap-2 cDNA sequence (SEQ ID NO:7) and the Hiap-2 polypeptide sequence (SEQ ID NO:8). The sequence absent in the hiap-2-Δ variant is boxed.

FIG. 4 is the murine xiap (also referred to as "miap-3") cDNA sequence (SEQ ID NO:9) and encoded murine Xiap polypeptide sequence (SEQ ID NO:10).

FIG. 5 is the murine hiap-1 (also referred to as "miap-1") cDNA sequence (SEQ ID NO: 11) and the encoded murine Hiap-1 polypeptide sequence (SEQ ID NO:12).

FIG. 6 is the murine hiap-2 (also referred to as "miap-2") cDNA sequence (SEQ ID NO: 13) and the encoded murine Hiap-2 polypeptide (SEQ ID NO: 14).

DETAILED DESCRIPTION

Figure 7:
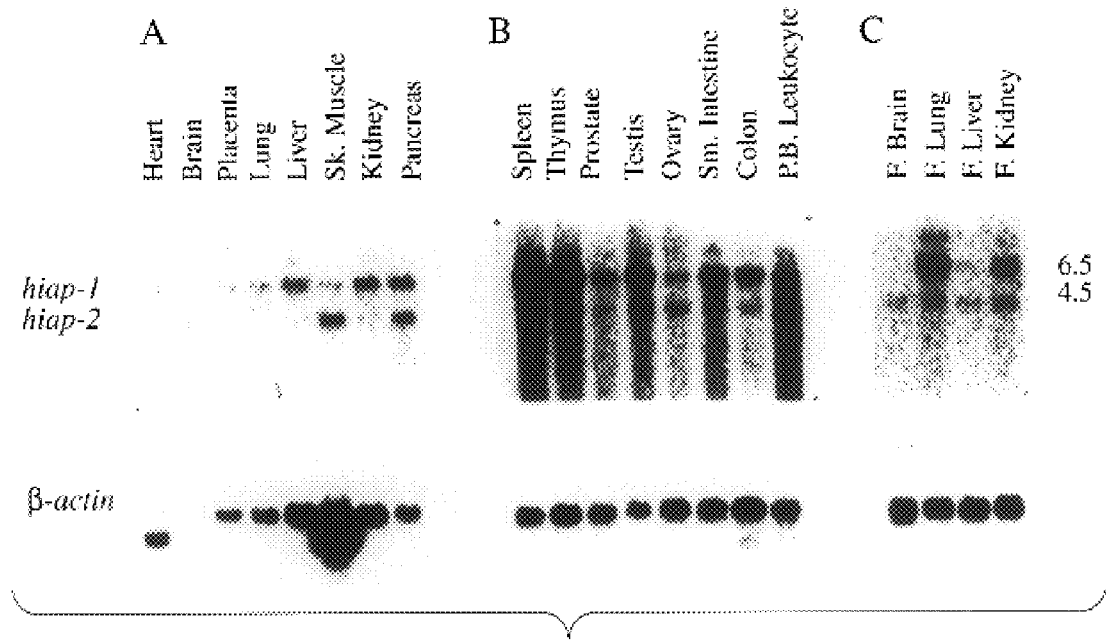
FIG. 7 is a series of photographs of Northern blots illustrating human hiap-1 and hiap-2 mRNA expression in human tissues.
Figure 8:
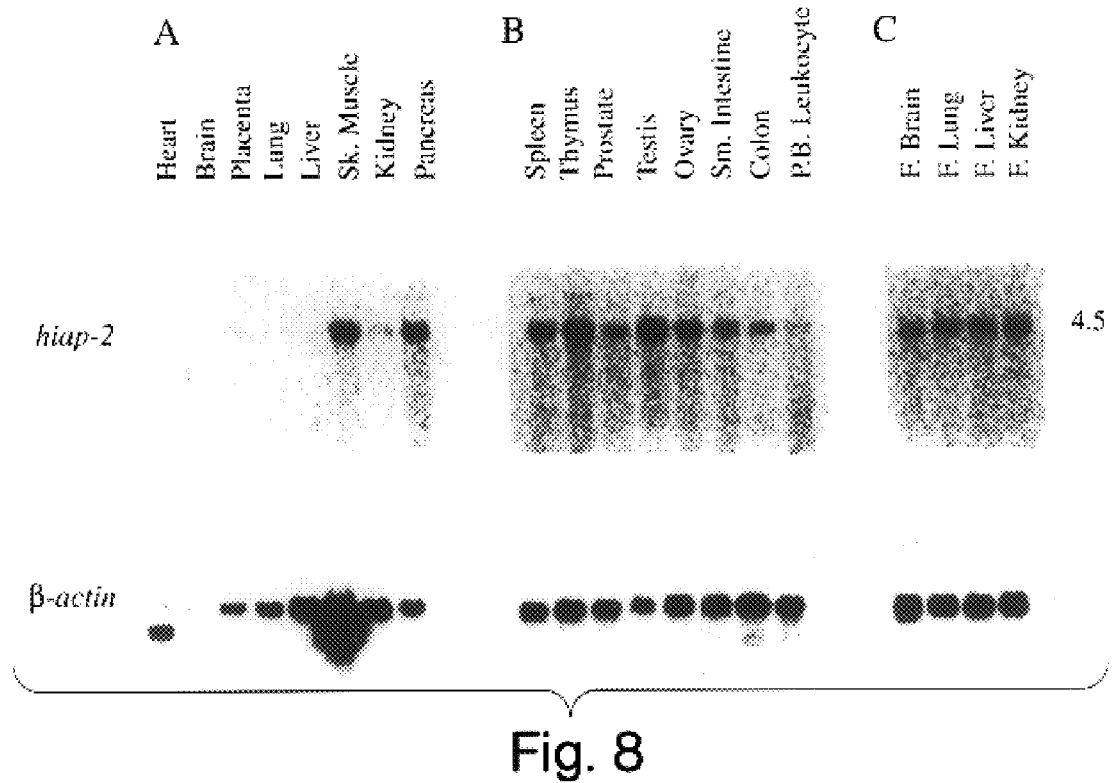
FIG. 8 is a series of photographs of Northern blots illustrating human hiap-2 mRNA expression in human tissues.
Figure 9:
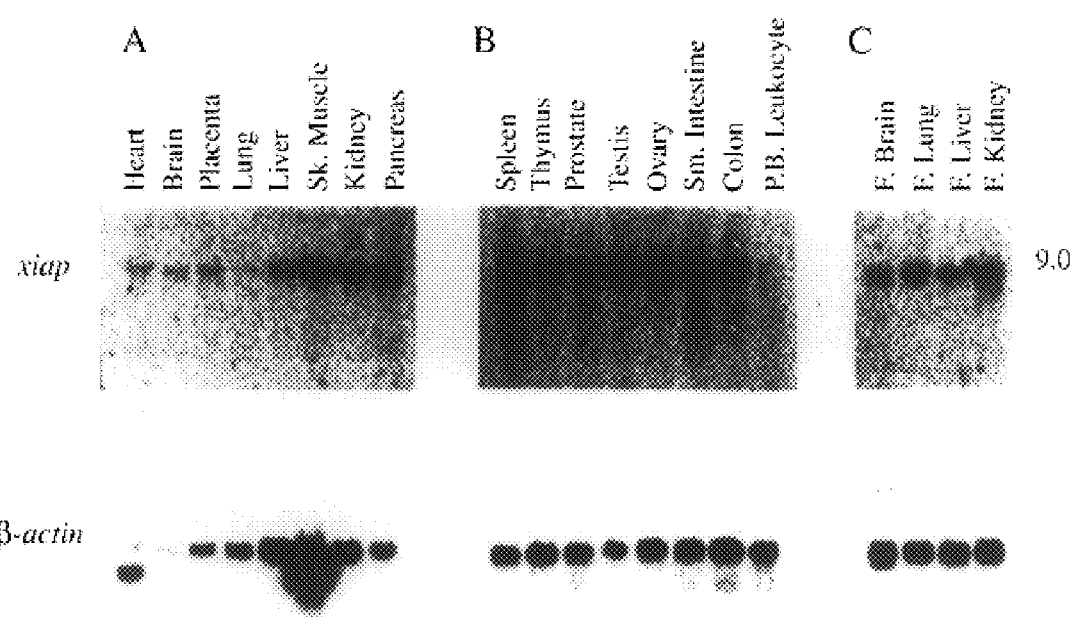
FIG. 9 is a series of photographs of Northern blots illustrating human xiap mRNA expression in human tissues.

Previously, we have provided a novel family of inhibitors of apoptosis, the IAPs, and an additional related anti-apoptotic protein, Naip. Here we provide identification of cancer types in which dysregulation of the IAPs and Naip is apparent. Our results are of paramount importance and provide diagnostics, prognostics, treatments, and drug screens aimed at the detection and effective treatment of cancer.

Cancer Screening

We initially studied IAP expression levels in a variety of normal tissues and cancer cell lines using commercially available northern blots. Elevated xiap, hiap-1 and hiap-2 mRNA was noted in a surprising number of cancer lines of diverse lineage, including colorectal cancer, lymphoma, leukemia, and melanoma cell lines. In contrast, bcl-2 mRNA was elevated in only a single cell line. Although this result reinforced the importance of the IAPs in cancer, the question remained as to whether the individual cancer cell lines on the blot were representative of the cancer type. As a result, we screened panels of cancer cell lines of particular tumor type by northern blot and quantitative RT-PCR analysis in order to ascertain the frequency of IAP dysregulation. The results are summarized as follows:

Burkitt's Lymphoma

We studied both the frequency and consequences of IAP upregulation in Burkitt's lymphoma. Elevated levels of hiap-1 and hiap-2 have been found in the vast majority of the Burkitt's cell lines examined. Furthermore, those Burkitt's lines expressing low levels of hiap-1 are transcriptionally activated by Epstein-Barr virus (EBV) infection.

Breast Adenocarcinoma

A key observation was made in this survey, in which a correlation was observed between drug resistance, p53 status and hiap-1 and hiap-2 expression. Four of the cell lines possessed wild-type p53, while three possessed documented p53 mutations that correlated with resistance to the anti-cancer drug adriamycin. Significantly, the three lines which were relatively more drug resistant also displayed elevated hiap-1 and hiap-2 mRNA levels. These results indicate that one of the ways that p53 controls apoptosis is through regulation of these genes.

Ovarian Carcinoma mRNA in situ analysis suggest a role for Naip in the developmental biology of the ovary. Overexpression of hiap-2 and xiap mRNA has also been documented in some ovarian cancer cell lines.

Pancreatic Cancer.

Approximately 25% of the cell lines tested to date demonstrate hiap-I and hiap-2 mRNA elevation.

Summary of Cancer Panels.

To date, a significant fraction of cancer cell lines of each type examined display elevated IAP levels. Our results indicate that hiap-1 and hiap-2 tend to be the most frequently and dramatically upregulated. The apparent coordinate regulation of both genes was surprising given their very different normal tissue distribution. hiap-1 and hiap-2 reside in tandem array on chromosome 11q23, a site frequently rearranged in lymphomas and leukemias.

Transcriptional regulation of the IAPs in cancer cell lines

Our experiments have established a correlation between p53 status and transcriptional overexpression of hiap-1 and hiap-2. This provides an important new way in which to enhance apoptosis, particularly in view of the fact that the mechanism by which p53 controls cell fate remains largely unknown. It has previously been documented that wild-type p53 negatively down-regulates bcl-2, and positively upregulates the Bcl-2 antagonist bax. In some cancer cell types, mutation of p53 causes a two-fold effect; namely, the upregulation of bcl-2, and down regulation of bax, both of which contribute to the anti-apoptotic phenotype. While not wishing to bind ourselves to a particular theory, we believe that wild-type p53 also transcriptionally suppresses hiap-1 and hiap-2. DNA damage that includes the increase in wild-type levels p53 levels would therefore result in decreased hiap-1 and hiap-2 in normal cells, resulting in apoptosis. Mutations in the p53 gene would therefore result in a loss of transcriptional control of these IAP genes. As a result, p53 mutant cancer cells would display constitutively high levels of hiap-1 and hiap-2, rendering the cells resistant to anti-cancer therapies. The p53/hiap-1 and hiap-2 correlations may be extended to the other cancer cell line panels. One may directly demonstrate p53 regulation of the IAPs using transfection assays and northern blot analysis.

Accordingly, we predict that cancer cells having p53 mutations (p53*) will have increased IAP levels resulting in a poor response to chemotherapeutics. Because IAP levels may be assessed more readily than the presence of a p53* mutation, our discovery also provides an important improvement in cancer diagnosis and prognosis (see below).

Transgenic Mice

We have constructed a number of IAP and Naip transgenic mouse expression vectors, including T-cell, B-cell, and neuronal specific promoter constructs. Founder mice have been identified and are viable for the most of these constructs, and we have developed breeding colonies. These mice will likely be prone to cancers of the tissue types in which the promoter is active. Thus the mice provide an excellent resource for testing the efficacy of antisense oligonucleotides and for screening for apoptosis-enhancing cancer therapeutics. Standard mouse drug screening models and gene delivery protocols may be employed to utilize the mice for this purpose.

Diagnostic/Prognostic Reagents

There is a relative lack of diagnostic and prognostic tests which clinical oncologists may utilize in determining the appropriate degree of intervention in the treatment of cancer. Mutation of the p53 gene remains one of the best prognostic indicators in cancer biology. However, the number of different mutations identified to date is great and scattered throughout the gene. In addition, many mutations in p53 result in an inappropriate stabilization of the protein, which allows detection at the protein level rather than at the mRNA level. Mutations which alter the transactivation/repression activities of the protein are not necessarily apparent at either the mRNA or protein levels. On the other hand, if IAP and Naip expression levels correlate with p53 mutation they may provide more valuable prognostic information and assist in the determination of which patients require more aggressive treatment. Thus the invention provides two assays for prognosis an diagnosis. Semi-quantitative RT-PCR based assays may be used to assay for IAP and/or Naip gene or protein expression levels. Alternatively, monoclonal antibodies may be incorporated into an ELISA (enzyme linked immunosorbant assay) type assay for direct determination of protein levels.

Therapeutic Products

For IAP related therapies one may employ the paradigms utilized for bcl-2 and ras antisense development, although accommodation of IAP mutation is not required (in contrast to ras antisense). Most useful are antisense constructs which enhance apoptosis at least 10%, preferably by enhancing degradation of the RNA in the nucleus.

In addition to antisense approached described herein the invention features small molecule screening assays which may be used to identify lead compounds that negatively regulate the IAPs. For example, compounds which enhance apoptosis in the presence of IAP overexpression or which decrease the level of IAP biological activity may be detected and are useful cancer therapeutics.

Molecules that are found, by the methods described above, to effectively modulate IAP gene expression or polypeptide activity may be tested further in animal models. If they continue to function successfully in an in vivo setting, they may be used as therapeutics to either inhibit or enhance apoptosis, as appropriate.

We have documented that overexpression of the IAPs renders cell lines resistant to serum growth factor withdrawal, tumor necrosis factor alpha (TNFα) and menadione exposure, all of which are treatments that normally induce apoptosis. Herein we describe the extension of these studies to cancer cell lines using apoptotic triggers used in clinical situations, such as doxorubicin, adriamycin, and methotrexate. Our findings have led up to design antisense RNA therapeutics. Rapid screening of multiple cell lines for apoptotic response has been made feasible through the generation of a series of sense and antisense adenoviral IAP and Naip expression vectors, as well as control lacZ viruses. One may now show enhanced drug resistance using the expression constructs. In addition, antisense adenovirus constructs may be developed and used to test reversal of the drug resistant phenotype of appropriate cell lines. We have surveyed cancer cell lines with the objective of identifying tumor types in which IAP overexpression is apparent or altered and these results are described both above and in the Examples below. Concomitant to this research, we have designed a series of antisense oligonucleotides to various regions of each of the IAPs. These oligonucleotides may be used to enhance drug sensitivity after testing in an assay system, i.e., with the adenoviral vectors system. Animal modeling of the effectiveness of antisense IAP oligos may also be employed as a step in testing and appropriate transgenic mammals for this are described above and also generally available in the art.

The following describes some of the testing systems which may be employed.

Anti-Cancer Gene Therapy

Retroviral vectors, adenoviral vectors, adeno-associated viral vectors, or other viral vectors with the appropriate tropism for cells likely requiring enhanced apoptosis (for example, breast cancer and ovarian cancer cells) may be used as a gene transfer delivery system for a therapeutic gene constructs. Numerous vectors useful for this purpose are generally known (Miller, Human Gene Therapy 15, 1990; Friedman, Science 244:1275, 1989; Eglitis and Anderson, BioTechniques 6:608, 1988; Tolstoshev and Anderson, Current Opinion in Biotechnology 1:55, 1990; Sharp, Lancet 337:1277, 1991; Cometta et al., Nucleic Acid Research and Molecular Biology 36:311, 1987; Anderson, Science 226:401, 1984; Moen, Blood Cells 17:407, 1991; Miller et al., BioTechniques 7:980, 1989; La Salle et al., Science 259:988, 1993; and Johnson, Chest 107:77S, 1995).

Retroviral vectors are particularly well developed and have been used in clinical settings (Rosenberg et al., N. Engl. J. Med 323:370, 1990; Anderson et al., U.S. Pat. No. 5,399,346). Non-viral approaches may also be employed for the introduction of therapeutic DNA into cells otherwise predicted to undergo apoptosis. For example, IAPs may be introduced into a neuron or a T cell by lipofection (Felgner et al., Proc. Natl. Acad. Sci. USA 84:7413, 1987; Ono et al., Neurosci. Lett. 117:259, 1990; Brigham et al., Am. J. Med. Sci. 298:278, 1989; Staubinger et al., Meth. Enz. 101:512, 1983), asialorosonucoid-polylysine conjugation (Wu et al., J. Biol. Chem. 263:14621, 1988; Wu et al., J. Biol. Chem. 264:16985, 1989); or, less preferably, microinjection under surgical conditions (Wolffet al., Science 247:1465, 1990).

For any of the methods of application described above, the therapeutic nucleic acid construct is preferably applied to the site of the needed apoptosis event (for example, by injection). However, it may also be applied to tissue in the vicinity of the predicted apoptosis event or to a blood vessel supplying the cells predicted to require enhanced apoptosis.

In the constructs described, nucleic acid expression can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in ovarian cells, breast tissue, neural cells, T cells, or B cells may be used to direct expression. The enhancers used could include, without limitation, those that are characterized as tissue- or cell-specific in their expression. Alternatively, if a clone used as a therapeutic construct, regulation may be mediated by the cognate regulatory sequences or, if desired, by regulatory sequences derived from a heterologous source, including any of the promoters or regulatory elements described above.

Less preferably, anti-cancer gene therapy is accomplished by direct administration of the therapeutic mRNA or antisense IAP mRNA to a cell that is expected to require enhanced apoptosis. The mRNA may be produced and isolated by any standard technique, but is most readily produced by inI vitro transcription using an IAP related nucleic acids under the control of a high efficiency promoter (e.g., the T7 promoter). Administration of IAP antisense mRNA to malignant cells can be carried out by any of the methods for direct nucleic acid administration described above.

Ideally, the production of IAP protein by any gene therapy approach will result in cellular levels of and/or fragments thereof that are at least equivalent to the normal, cellular level of IAP in an unaffected cell. Treatment by any IAP-modulating gene therapy approach may be combined with more traditional therapies.

Another therapeutic approach within the invention involves administration of recombinant IAP protein fragments or IAP antibodies, either directly to the site where enhanced apoptosis is desirable (for example, by injection) or systemically (for example, by any conventional recombinant protein administration technique).

The dosage of IAP, the IAP fragment, IAP mutant protein or IAP antibody depends on a number of factors, including the size and health of the individual patient, but, generally, between 0.1 mg and 100 mg inclusive are administered per day to an adult in any pharmaceutically acceptable formulation.

Administration

An IAP mutant protein or protein fragment, gene encoding the same, gene encoding IAP antisense RNA, or modulator of an IAPs may be administered within a pharmaceutically-acceptable diluent, carrier, or excipient, in unit dosage form. Conventional pharmaceutical practice may be employed to provide suitable formulations or compositions to administer the compounds to patients suffering from a disease that is caused by excessive cell proliferation. Administration may begin before the patient is symptomatic. Any appropriate route of administration may be employed, for example, administration may be parenteral, intravenous, intraarterial, subcutaneous, intramuscular, intracranial, intraorbital, ophthalmic, intraventricular, intracapsular, intraspinal, intracisternal, intraperitoneal, intranasal, aerosol, suppository, or oral administration. For example, therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington's Pharmaceutical Sciences." Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for IAP modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

If desired, treatment with IAP mutant proteins or IAP fragments, related genes, or other modulatory compounds may be combined with more traditional therapies for the proliferative disease such as surgery or chemotherapy.

Detection of Conditions Involving Insufficient Apoptosis

IAP polypeptides and nucleic acid sequences find diagnostic use in the detection or monitoring of conditions involving insufficient levels of apoptosis, i.e., proliferative disease. For example, increased expression of IAPs, alterations in localization, and IAP cleavage correlate with inhibition of apoptosis and cancer in humans. Accordingly, an increase in the level of IAP production may provide an indication of a proliferative condition or a predisposition to such a condition. Levels of IAP expression may be assayed by any standard technique. For example, IAP expression in a biological sample (e.g., a biopsy sample) may be monitored by standard Northern blot analysis or may be aided by PCR (see, e.g., Ausubel et al., supra; *PCR Technology: Principles and Applications for DNA Amplification,* H. A. Ehrlich, Ed. Stockton Press, NY; Yap et al. Nucl. Acids. Res. 19:4294, 1991).

Alternatively, a biological sample obtained from a patient may be analyzed for one or more mutations in the IAP sequences or p53 sequences using a mismatch detection approach. Generally, these techniques involve PCR amplification of nucleic acid from the patient sample, followed by identification of the mutation (i.e., mismatch) by either altered hybridization, aberrant electrophoretic gel migration, binding or cleavage mediated by mismatch binding proteins, or direct nucleic acid sequencing. Any of these techniques may be used to facilitate mutant IAP detection, and each is well known in the art; examples of particular techniques are described, without limitation, in Orita et al., Proc. Natl. Acad. Sci. USA 86:2766, 1989; Sheffield et al., Proc. Natl. Acad. Sci. USA 86:232, 1989).

In yet another approach, immunoassays are used to detect or monitor IAP protein in a biological sample. IAP-specific polyclonal or monoclonal antibodies (produced as described above) may be used in any standard immunoassay format (e.g., ELISA, Western blot, or RIA) to measure IAP polypeptide level or IAP levels from cancerous control cells. These levels would be compared to wild-type IAP levels, with a decrease in IAP production relative to a wild-type cell indicating a condition involving increased apoptosis and a decrease relative to a known cancer cell indicating a decreased likelihood of an IAP related cancer. Examples of immunoassays are described, e.g., in Ausubel et al., supra. Immunohistochemical techniques may also be utilized for IAP detection. For example, a tissue sample may be obtained from a patient, sectioned, and stained for the presence of IAP using an anti-IAP antibody and any standard detection system (e.g., one which includes a secondary antibody conjugated to horseradish peroxidase). General guidance regarding such techniques can be found in, e.g., Bancroft and Stevens (*Theory and Practice of Histological Techniques*, Churchill Livingstone, 1982) and Ausubel et al. (supra).

In one preferred example, a combined diagnostic method may be employed that begins with an evaluation of IAP protein production (for example, by immunological techniques or the protein truncation test (Hogerrorst et al., Nature Genetics 10:208–212, 1995)) and also includes a nucleic acid-based detection technique designed to identify more subtle IAP altercations, e.g., mutations. As described above, a number of mismatch detection assays are available to those skilled in the art, and any preferred technique may be used. Mutations in IAP may be detected that either result in enhanced IAP expression or altercations in IAP biological activity. In a variation of this combined diagnostic method, IAP biological activity is measured as anti-apoptotic activity using any appropriate apoptosis assay system (for example, those described above).

Mismatch detection assays also provide an opportunity to diagnose an IAP-mediated predisposition to diseases caused by insufficient apoptosis. For example, a patient heterozygous for an IAP mutation may show no clinical symptoms and yet possess a higher than normal probability of developing one or more types of proliferative diseases. Given this diagnosis, a patient may take precautions to minimize their exposure to adverse environmental factors (for example, UV exposure or chemical mutagens) and to carefully monitor their medical condition (for example, through frequent physical examinations). This type of IAP diagnostic approach may also be used to detect IAP mutations in prenatal screens. The IAP diagnostic assays described above may be carried out using any biological sample (for example, any biopsy sample or bodily fluid or tissue) in which IAP is normally expressed. Identification of a mutant IAP gene may also be assayed using these sources for test samples.

Alternatively, an altercation in IAP activity, particularly as part of a diagnosis for predisposition to IAP-associated proliferative disease, may be tested using a nucleic acid sample from any cell, for example, by mismatch detection techniques. Preferably, the DNA sample is subjected to PCR amplification prior to analysis.

EXAMPLE 1

Elevated IAP Levels in Cancer Cell Lines

In order to specifically demonstrate the utility of IAP gene sequences as diagnostics and prognostics for cancer, a Human Cancer Cell Line Multiple Tissue Northern Blot (Clontech, Palo Alto, Calif.; #7757-1) was probed. This Northern blot contained approximately 2 µg of poly A$^+$ RNA per lane from eight different human cell lines: (1) promyelocytic leukemia HL-60, (2) HeLa cell S3, (3) chronic myelogenous leukemia K-562, (4) lymphoblastic leukemia MOLT-4, (5) Burkitt's lymphoma Raji, (6) colorectal adenocarcinoma SW480, (7) lung carcinoma A549, and (8) melanoma G361. As a control, a Human Multiple Tissue Northern Blot (Clontech, Palo Alto, Calif.; #7759-1) was probed. This Northern blot contained approximately 2 µg of poly A$^+$ RNA from eight different human tissues: (1) spleen, (2) thymus, (3) prostate, (4) testis, (5) ovary, (6) small intestine, (7) colon, and (8) peripheral blood leukocytes.

The Northern blots were hybridized sequentially with: (1) a 1.6 kb probe to the xiap coding region, (2) a 375 bp hiap-2 specific probe corresponding to the 3' untranslated region, (3) a 1.3 kb probe to the coding region of hiap-1, which cross-reacts with hiap-2, (4) a 1.0 kb probe derived from the coding region of bcl-2, and (5) a probe to β-actin, which was provided by the manufacturer. Hybridization was carried out at 50° C. overnight, according to the manufacturer's suggestion. The blot was washed twice with 2× SSC, 0.1% SDS at room temperature for 15 minutes and then with 2× SSC, 0.1% SDS at 50° C.

All cancer lines tested showed increased IAP expression relative to samples from non-cancerous control tissues (Table 1). Expression of xiap was particularly high in HeLa (S-3), chronic myelogenous leukemia (K-562), colorectal adenocarcinoma (SW-480), and melanoma (G-361) lines. Expression of hiap-1 was extremely high in Burkitt's lymphoma, and was also elevated in colorectal adenocarcinoma. Expression of hiap-2 was particularly high in chronic myelogenous leukemia (K-562) and colorectal adenocarcinoma (SW-480). Expression of bcl-2 was upregulated only in HL-60 leukemia cells.

TABLE 1

NORTHERN BLOT IAP RNA LEVELS IN CANCER CELLS*

|  | xiap | hiap1 | hiap2 |
| --- | --- | --- | --- |
| Promyelocytic Leukemia HL-60 | + | + | + |
| Hela S-3 | + | + | + |
| Chronic Myelogenous Leukemia K-562 | +++ | + | +++ |
| Lymphoblastic Leukemia MOLT-4 | +++ | + | + |
| Burkitt's Lymphoma Raji | + | +(×10) | + |
| Colorectal Adenocarcinoma SW-480 | +++ | +++ | +++ |
| Lung Carcinoma A-549 | + | + | + |
| Melanoma G-361 | +++ | + | + |

*Levels are indicated by a (+) and are the approximate increase in RNA levels relative to Northern blots of RNA from non-cancerous control cell lines. A single plus indicates an estimated increase of at least 1-fold These observations indicate that upregulation of the anti-apoptotic IAP genes may be a widespread phenomenon in proliferative diseases, perhaps occurring much more frequently than upregulation of bcl-2. Furthermore, upregulation may be necessary for the establishment or maintenance of the transformed state of cancerous cells.

Figure 11:
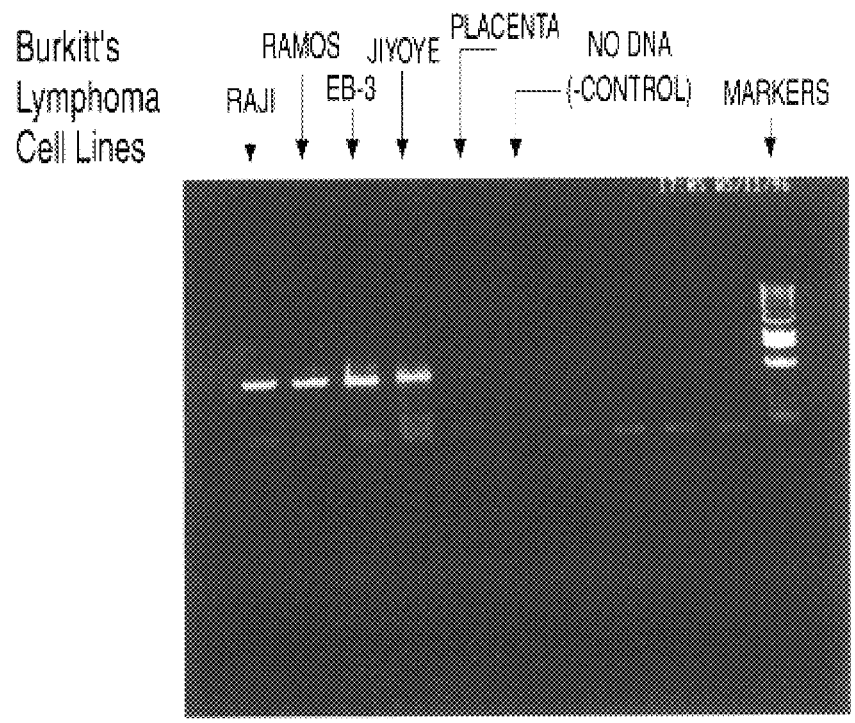
FIG. 11 is a photograph of an agarose gel containing cDNA fragments that were amplified, with hiap-1-specific primers, from RNA obtained from Raji, Ramos, EB-3, Burkitt's lymphoma cells, and Jiyoye cells, and cells from normal placenta.

In order to pursue the observation described above, i.e., that hiap-1 is overexpressed in the Raji Burkitt's lymphoma cell line, RT-PCR analysis was performed in multiple Burkitt's lymphoma cell lines. Total RNA was extracted from cells of the Raji, Ramos, EB-3, and Jiyoye cell lines, and as a positive control, from normal placental tissue. The RNA was reverse transcribed, and amplified by PCR with the following set of oligonucleotide primers: 5'-AGTGCGGGTTTTTATTATGTG-3' (SEQ ID NO: 15) and 5'-AGATGACCACAAGGAATAAACACTA-3' (SEQ ID NO: 16), which selectively amplify a hiap-1 cDNA fragment. RT-PCR was conducted using a PerkinElmer 480 Thermocycler to carry out 35 cycles of the following program: 94° C. for 1 minute, 50° C. for 1.5 minutes, and 72° C. for a minute. The PCR reaction product was electrophoresed on an agarose gel and stained with Ethidium bromide. Amplified cDNA fragments of the appropriate size were clearly visible in all lanes containing Burkitt's lymphoma samples, but absent in the lanes containing the normal placental tissue sample, and absent in lanes containing negative control samples, where template DNA was omitted from the reaction (FIG. 11).

EXAMPLE 2
IAPs in Breast Cancer

Figure 18:
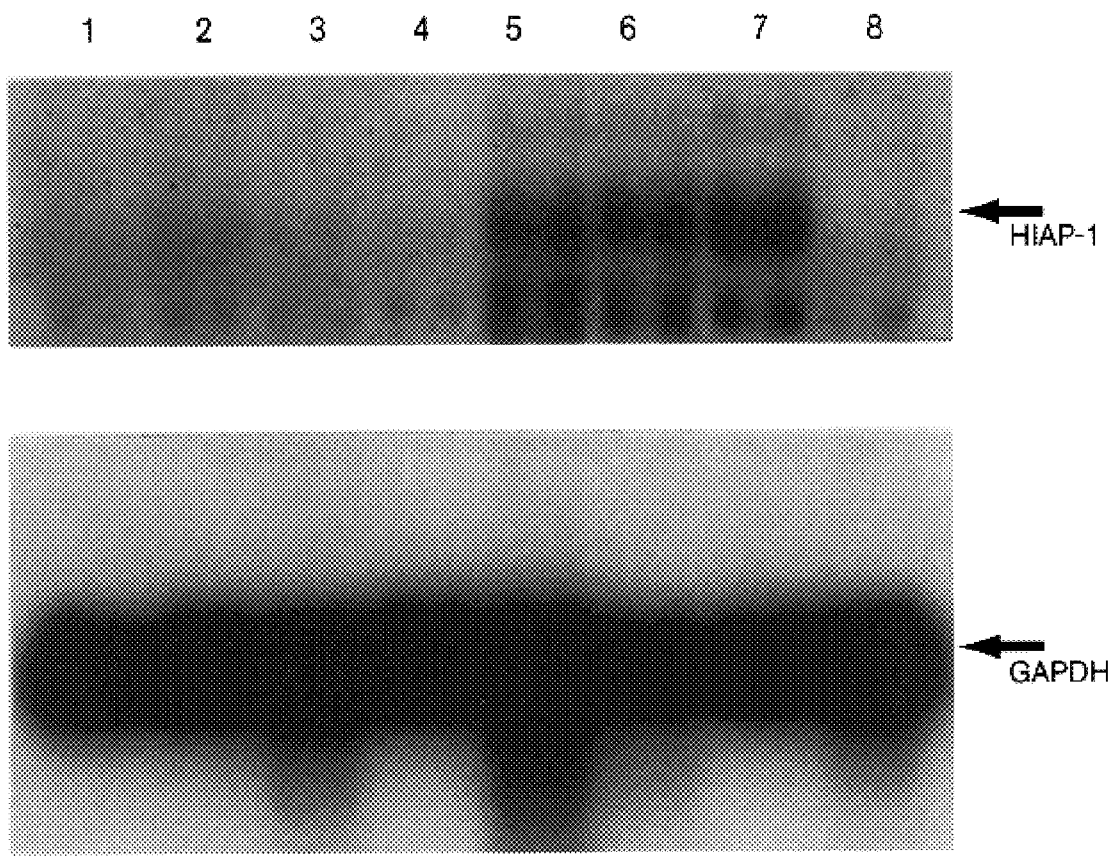
FIGS. 18 and 19 shows the increased level of hiap-1 and hiap-2 mRNA, respectively, in breast cancer cell lines having p53 mutations (lanes 5–7). The bottom portion of the figure shows the control.
Figure 19:
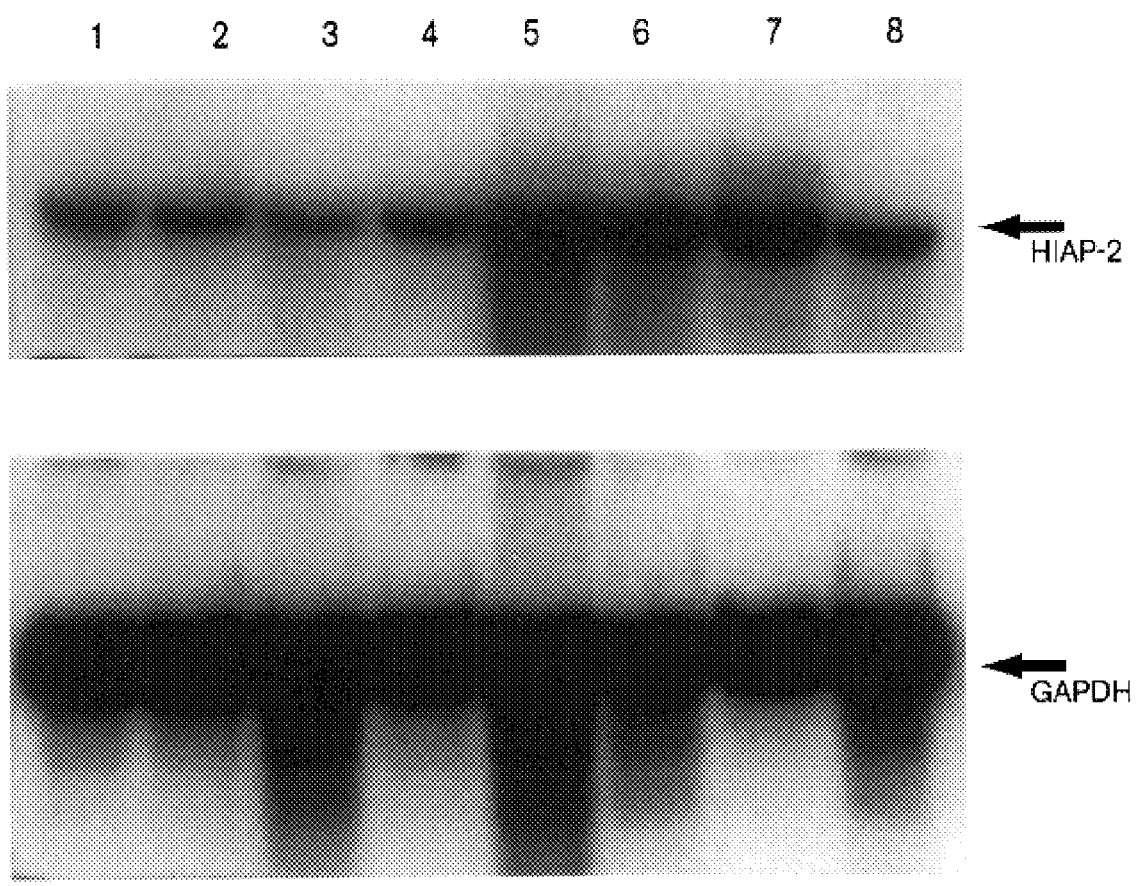

The following data relate to the regulation and role of HIAPs in cancer cells. FIGS. 18 and 19 show data demonstrating that hiap-1 and hiap-2 are both upregulated in breast cancer cell lines that contain mutant p53. The lanes contain 20 μg of total RNA from the following lines: 1. MCF-7 (clone 1, wt p53) 2. MCF-7 (clone 2, wt p53) 3. MCF-7 (American Type Culture Collection, wt p53) 4. MCF-7 (parental line, California, wt p53) 5. MCF-7 (California, adriamycin resistant variant, mutant p53), 6. MDA MB 231 (ATCC, mutant p53, codon 280) 7.T47-D (ATCC, mutant p53, codon 194) 7. ZR-75 (ATCC, wt p53). The amount of RNA loaded on each gel was controlled for by hybridization with glycerol phosphate dehydrogenase (GAPDH).

EXAMPLE 3
IAPs in Ovarian Cancer
Overview

Epithelial ovarian cancer is the leading cause of death from gynecologic malignancy. Although clinical and histologic prognostic factors such as tumor grade and surgical stage are well understood, the biologic process that leads to uncontrolled cellular growth is less clear. The control of cell numbers during tissue growth is thought to be the results of a balance of cell proliferation and cell death. An aberration in this natural homeostasis likely contributes to malignant cellular transformation.

Recent studies on ovarian cancer cell biology have suggested that the deregulation of apoptosis may be one of the underlying pathologic mechanism in this disease. However, the molecular mechanisms involved in its regulation is poorly understood and the role and regulation of the IAP genes in ovarian cell transformation have not been examined previously. Ovarian epithelial cancer is in part a result of suppressed apoptosis of ovarian surface epithelial cells. The effectiveness of certain chemotherapeutic agents rests on their ability to induce cell death. The loss of responsiveness of the cells to these agents is due to a desensitization of the apoptotic process to these agents. The regulation of ovarian epithelial cell apoptosis involves changes in the expression of IAP genes and post-translational modification/processing of the IAP gene products.

We have conducted experiments and now believe that IAPs play a key role in maintaining the normal growth of ovarian surface epithelial cells and that the overexpression of these genes leads to cellular transformation. Furthermore, we have discovered that the effectiveness of chemotherapeutic agents in the treatment of this form of malignancy rests upon their ability to suppress the expression of the IAP genes. By seeking to control the regulation of the IAP genes in human ovarian epithelial cancer cells we have provided a rational approach for the development of new chemotherapeutics for patients both responsive and resistant to current cancer drugs. Similarly, assays designed to detect compounds which decrease IAP biological activity provide a rational method for drug discovery.

Methods
A) Human Ovarian Epithelial Cancer Cell Culture

Cisplatin-sensitive (OV2008) and -resistant (C13) human ovarian epithelial cells were cultured in a chemically-defined medium at 37° C. for up to 48 hours in the presence or absence of TGFP (20 ng/ml), Taxol (0–1.0 μM) or cisplatin (0–30 μM). At the end of the culture period, cells were either fixed for immunocytochemistry and TUNEL analyses, or snap frozen for subsequent extraction for IAP mRNA and proteins analyses.

B) Identification of Cell Death
Nuclear Staining:

Human ovarian epithelial cancer cells were fixed (4% formalin in PBS; 10 min. RT), washed in PBS, resuspended in Hoescht 33248 stain (0.1 μg/ml PBS, 10 min) washed again and spotted onto slides for microscopy. Nuclear staining was observed and photographed using a Zeiss fluorescent microscope equipped with an FITC filter. Apoptotic cells were identified by typical nuclear morphology, and counted using randomly selected fields and numbered photographic slides to avoid bias during counting.

Quantification of DNA ladders:

Cellular DNA was extracted using the Qiagen Blood Amt kit. DNA was quantified by ethidium bromide fluorescence. DNA (0.5 kg) was then end labelled by incubating (20 min, RT) with Klenow enzyme (2 U in 10 mM Tris+5 mM $MgCl_2$) and 0.1 μCi[(α32P]dCTP. Unincorporated nucleotides were removed with the Qiagen nucleotide removal kit and samples were resolved by Tris-acetate-EDTA agarose (1.8%) gel electrophoresis. The gel was then dried (2 hr, no heat) and exposed to a Bio-Rad phosphoimager screen to densitometrically quantify low molecular weight DNA (<15 kBp) and subsequently to x-ray film at −80° C.

In Situ TUNEL Labelling of Apoptotic Cells:

To identify cell death using the in situ cell death detection kit (Boehringer-Mannheim), slides prepared for histology were treated (20 min. 37° C.) with terminal transferase in the presence of FITC-conjugated dUTP.

C) Western Blot Analyses for IAPs

Protein extracts were prepared from human surface epithelial cancer cells sonicated (8 s/cycle, 3 cycles) on ice in sucrose buffer (0.25 M sucrose, 0.025 M NaCl, 1 mM EGTA and 15 mM Tris-HCl pH 6.8, supplemented with 1 mM PMSF, 2 μg/ml of leupeptin and 5 μg/ml of aprotinin. The sonicates were centrifuged at 13,000× g for 10 min, the supernatants were collected and stored at −20° C. until electrophoretic analyses were performed. Protein concentration was determined by Bio-Rad Protein Assay. Proteins (10–30 μg) were resolved by one-dimensional SDS-PAGE, and electrophoretically transferred to nitrocellulose membrane. Membranes were blocked with 5% non-fat milk, and subsequently incubated with rabbit polyclonal antibody for IAP [anti-human Hiap-2ΔE(960529; 1:1000 dilution), anti-human Naip E1.0 (951015; 1:1000 dilution) or anti-human Xiap (1:1000 dilution) diluted in TBST (10 mM Tris-buffered saline, 0.1% Tween-20, pH7.5) containing 5% milk. An ECL kit was used to visualize immunopositive protein.

D) Northern Blots for IAP mRNAs

Total RNA from ovarian surface epithelial cancer cells by using RNeasy Kit (Qiagen). The RNA samples (10–15 μg) were quantified spectrophotometrically and size-fractioned by electrophoresis on formaldehyde-agarose gels (1.1%) containing 1 μg/ml ethidium bromide to confirm even loading of RNA samples and adequate separation of 28S and 18S ribosomal bands. The RNAs bands were blotted onto a nylon membrane and cross-linked by UV light. Membranes were prehybridized in 50% formamide, saline sodium citrate (SSC; 750 mM NaCl, 75 mM Na citrate), IX Denhardt's solution, 1% SDS, 4 mM EDTA and 100 μg/ml sheared salmon sperm DNA for 4 h at 42° C. Hybridization was performed overnight at 42° C. with 20 million cpm of $^{32}$P-labelled IAP cDNA probes (rat naip, rat xiap or human hiap-2) added to the prehybridization buffer. The membranes were then washed twice with SSC (300 mM NaCl, 30 mM sodium citrate) in 0.1% SDS for 20 min at room temperature and twice with SSC (30 mM NaCl, 3 mM sodium citrate) in 0.1% SDS for 20 min at 55° C. and exposed to X-ray film at −80° C. for visualization. Densitometric analysis of various IAPs and 28S rRNA band was performed with the Image Analysis Systems from Bio-Rad Laboratories. Data were normalized by the respective 28S and expressed as a percentage of the control (defined as 100%).

Results

Figure 20:
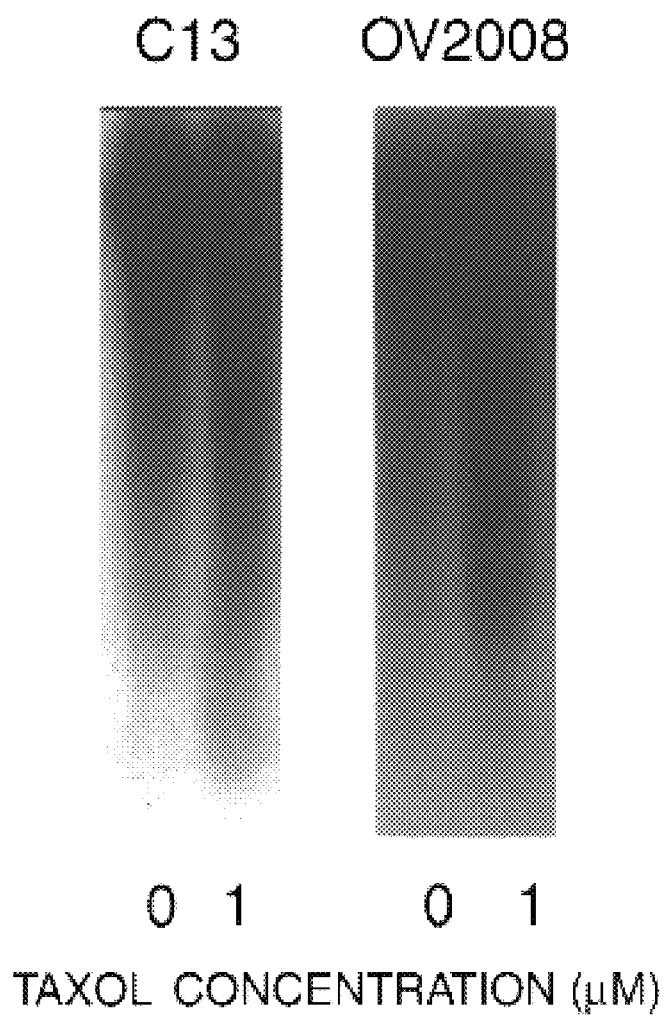
FIG. 20 shows the influence of Taxol on DNA fragmentation in Cisplatinin-sensitive (right) and resistant (left) human ovarian epithelial cancer cells.
Figure 21:
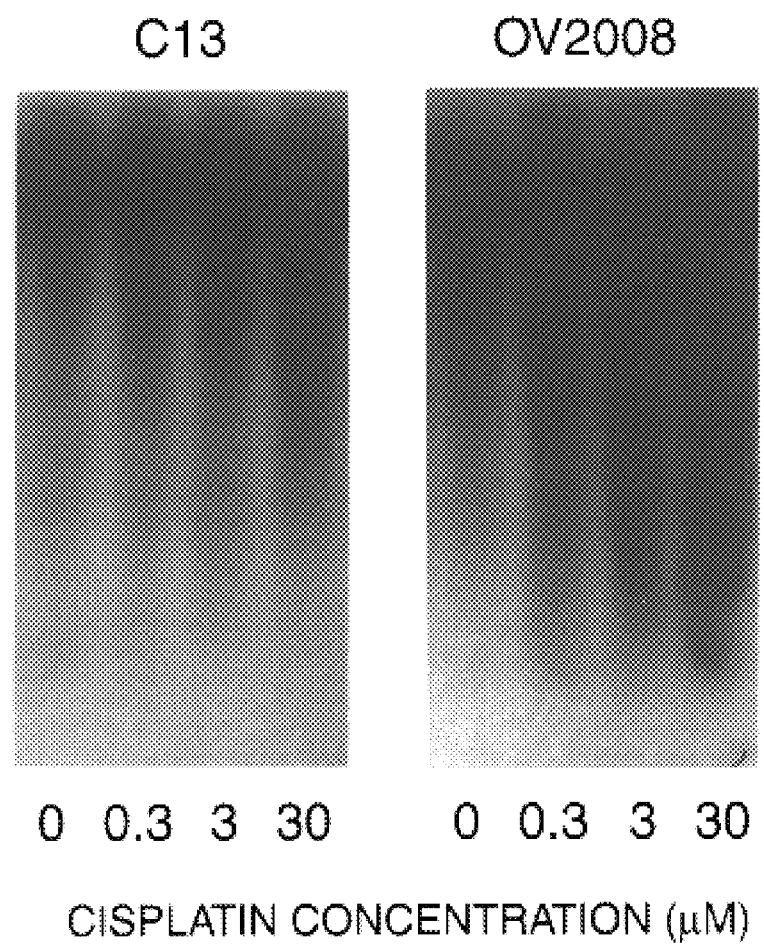
FIG. 21 shows the influence of Cisplatinin on DNA fragmentation in sensitive (right) and resistant (left) human ovarian epithelial cancer cells.

Cisplatin induced a concentration-dependent increase in the incidence of apoptosis in cisplatin-sensitive (OV2008) but to a lesser extent in cisplatin-resistant (C13) human ovarian epithelial cells in vitro (FIG. 20). Similarly, Taxol also induced apoptosis in OV2008 cells, but to a lesser extent in the C13 cells (FIG. 21).

Figure 22:
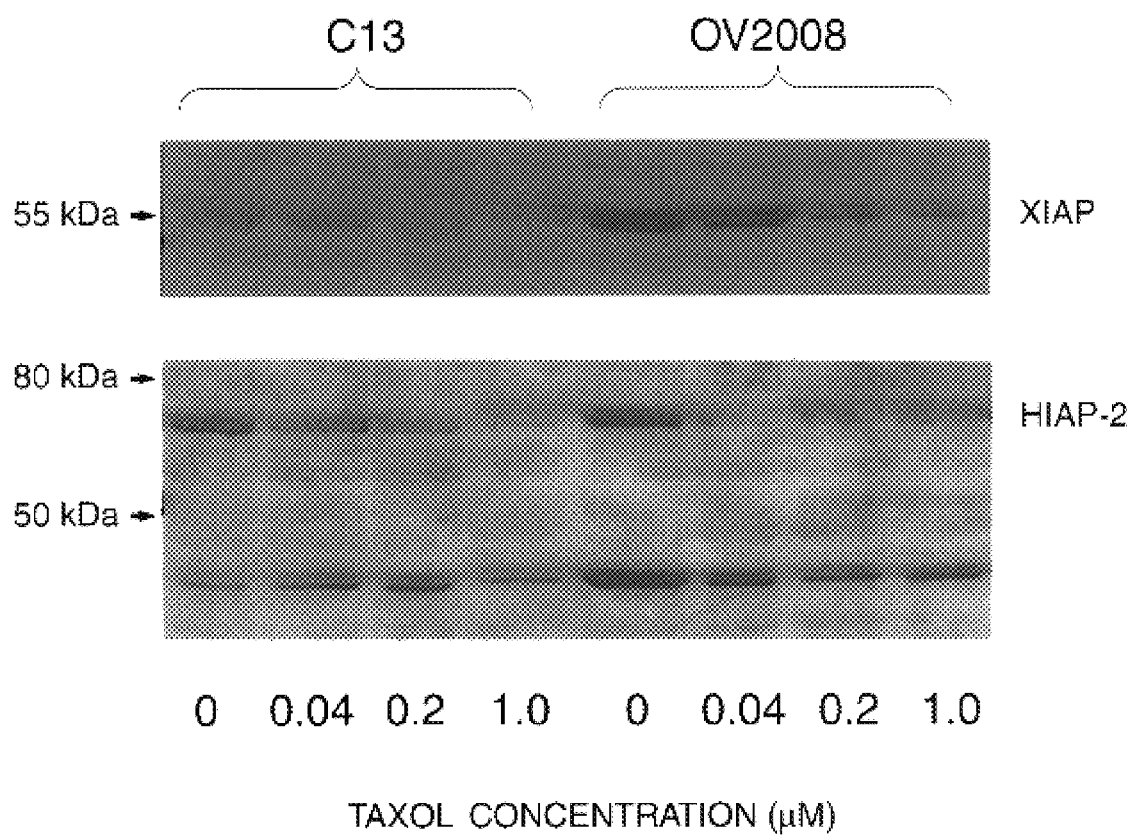
FIG. 22 shows the effects of Taxol on Xiap and Hiap-2 protein levels in Cisplatinin sensitive (right) and resistant (left) human ovarian epithelial cancer cells.

Basal Xiap and Hiap-2 protein contents were markedly higher in cisplatin-sensitive than cisplatin-resistant cells. Taxol (0.04–1.0 μM) decreased Xiap and Hiap-2 protein levels in a concentration-dependent manner, the response being more pronounced in sensitive than resistant cells (FIG. 22). A lower molecular weight (approx. 45 kDa) immunoreactive fragment of HIAP-2 was also evident in both the sensitive and resistant cells. The content of this fragment was increased in the C13 cells but decreased in OV2008 cells by Taxol (FIG. 22).

Figure 23A:
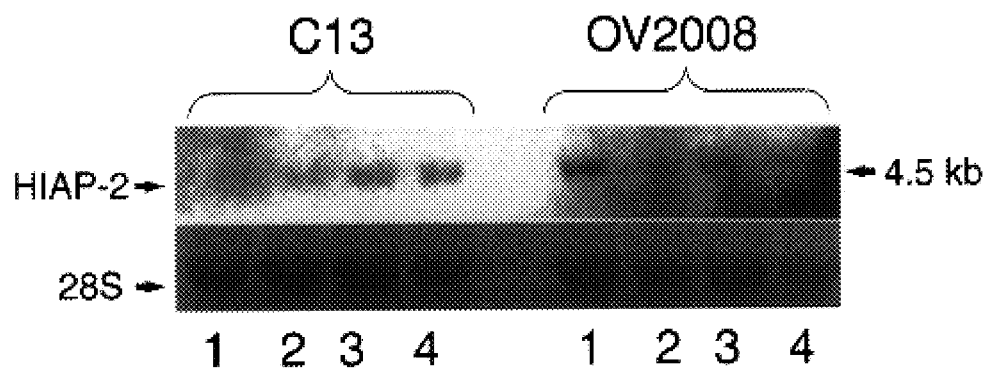
FIGS. 23A and 23B show the influence of Taxol and TGFβ on HIAP-2 mRNA levels in Cisplatinin sensitive (right) and resistant (left) human epithelial cancer cells.
Figure 23B:
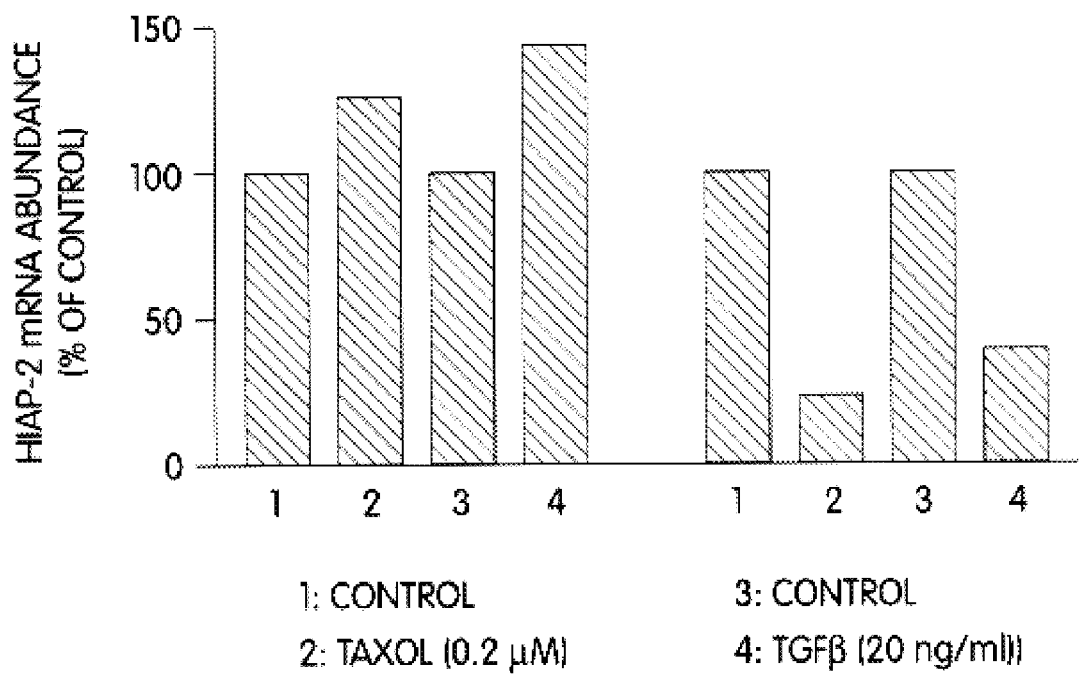

Whereas Taxol (0.2 μM) marked suppressed hiap-2 mRNA abundance in cisplatin-sensitive cells (approx. 80%), it was ineffective in the resistant cells (FIG. 23).

Figure 24A:
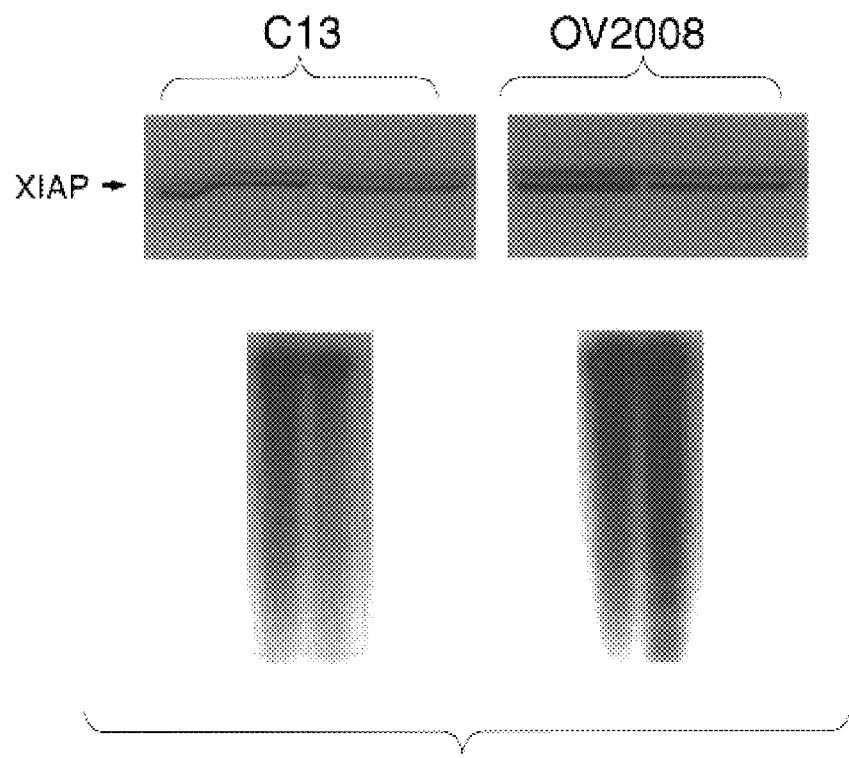
FIGS. 24A and 24B show the effect of TGFβ on XIAP protein expression, FIG. 24A, and DNA fragmentation, FIG. 24B, in Cisplatinin sensitive and resistant cells.
Figure 24B:
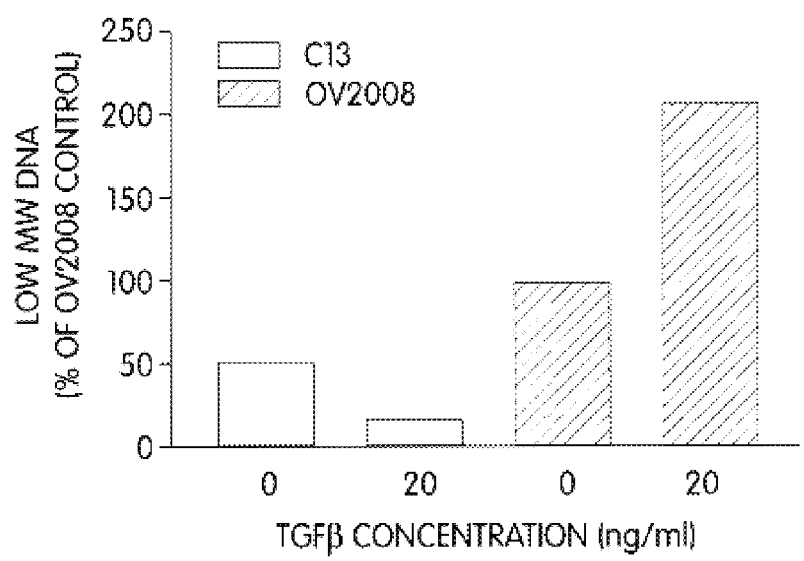

4. TGFβ (20 ng/ml) induced apoptosis in OV2008 but not in C13. Although its influence on Xiap protein content in cisplatin-resistant cells was only marginal, it markedly suppressed the protein level of this IAP in the cisplatin-sensitive cells (FIG. 24A, 24B). TGFP (20 ng/ml) also decreased hiap-2 mRNA in OV2008 but not C13 cells (FIG. 23).

Significant observations and possible applications

Induction of apoptosis in human ovarian epithelial cancer cell by Taxol was accompanied by suppressed IAP gene expression. The lost of sensitivity of the cells to the chemotherapeutic agent may be associated with its decreased ability to express these genes and to induce apoptosis. In drug-resistant cells, the decreased Hiap-2 protein content (in the face of an absence of noticeable change in hiap-2 mRNA abundance) in the presence of Taxol was accompanied an increase in the intensity of a 45 kDa immunoreactive Hiap-2 protein band. These observations lead us to believe that the 45 kDa protein is a proteolytic product of Hiap-2 and plays a role in the development of drug resistance. In addition, the sensitivity of the IAP family in these ovarian cancer cells to Taxol suggest possible novel sites for gene targeting in the development of new chemotherapeutic agents for the treatment of human ovarian epithelial cell cancer.

EXAMPLE 4

Accumulation of a 26 kDa Cleavage Protein in Astrocytoma Cells

Identification of a 26 kDa Cleavage Protein

Figure 12:
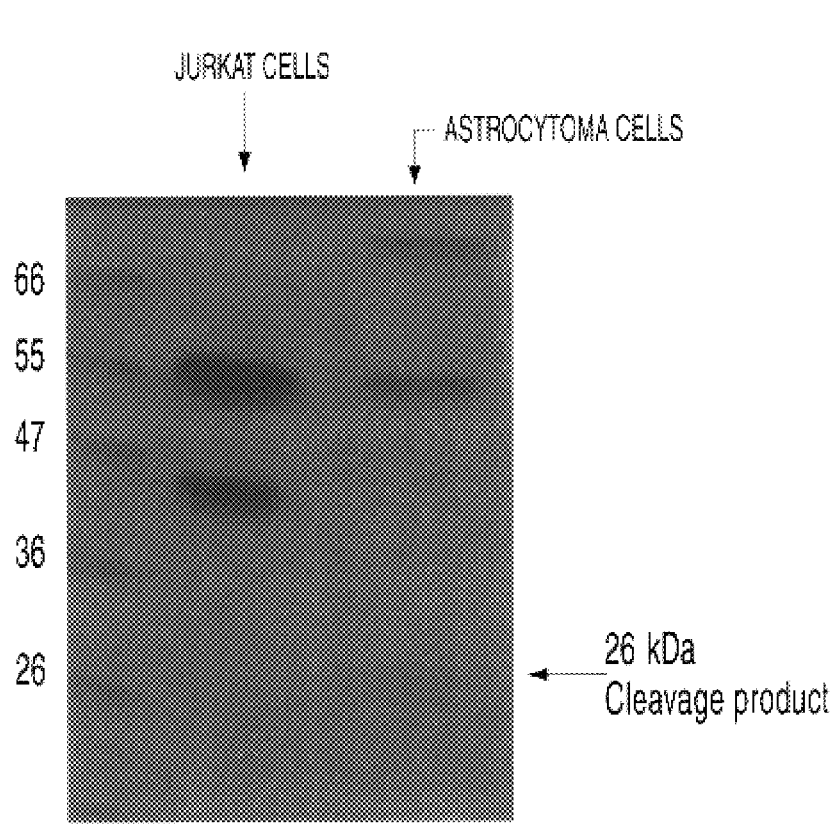
FIG. 12 is a photograph of a Western blot containing protein extracted from Jurkat and astrocytoma cells stained with an anti-Xiap antibody. The position and size of a series of marker proteins is indicated.

A total protein extract was prepared from Jurkat and astrocytoma cells by sonicating them (×3 for 15 seconds at 4° C.) in 50 mM Tris-HCl (pH 8.0), 150 mM NaCl, 1 mM PMSF, 1 μg/ml aprotinin, and 5 mM benzamidine. Following sonication, the samples were centrifuged (14,000 RPM in a microfuge) for five minutes. Twenty μg of protein was loaded per well on a 10% SDS-polyacrylamide gel, electrophoresed, and electroblotted by standard methods to PVDF membranes. Western blot analysis, performed as described previously, revealed that the astrocytoma cell line (CCF-STTG 1) abundantly expressed an anti-Xiap reactive band of approximately 26 kDa, despite the lack of an apoptotic trigger event (FIG. 12). In fact, this cell line has been previously characterized as being particularly resistant to standard apoptotic triggers.

Figure 13:
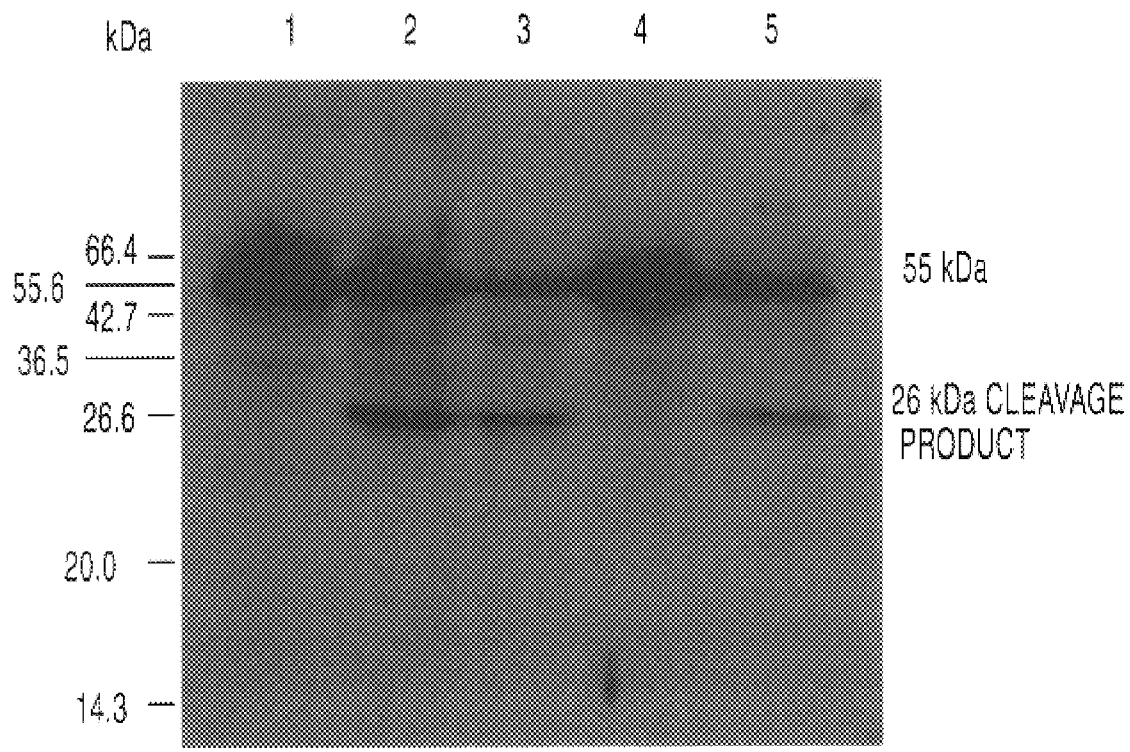
FIG. 13 is a photograph of a Western blot containing protein extracted from Jurkat cells following treatment as described in Example 12. The blot was stained with a rabbit polyclonal anti-Xiap antibody. Lane 1, negative control; lane 2, anti-Fas antibody; lane 3, anti-Fas antibody and cycloheximide; lane 4, TNF-α; lane 5, TNF-α and cycloheximide.

A 26 kDa Xiap-reactive band was also observed under the following experimental conditions. Jurkat cells (a transformed human T cell line) were induced to undergo apoptosis by exposure to an anti-Fas antibody (1 μg/ml). Identical cultures of Jurkat cells were exposed either to: (1) anti-Fas antibody and cycloheximide (20 μg/ml), (2) tumor necrosis factor alpha (TNFα, at 1,000 μ/ml), or (3) TNFα: and cycloheximide (20 μg/ml). All cells were harvested 6 hours after treatment began. In addition, as a negative control, anti-Fas antibody was added to an extract after the cells were harvested. The cells were harvested in SDS sample buffer, electrophoresed on a 12.5% SDS polyacrylamide gel, and electroblotted onto PVDF membranes using standard methods. The membranes were immunostained with a rabbit polyclonal anti-Xiap antibody at 1:1000 for 1 hour at room temperature. Following four 15 minute washes, a goat anti-rabbit antibody conjugated to horseradish peroxidase was applied at room temperature for 1 hour. Unbound secondary antibody was washed away, and chemiluminescent detection of Xiap protein was performed. The Western blot revealed the presence of the full-length, 55 kDa Xiap protein, both in untreated and treated cells. In addition, a novel, approximately 26 kDa xiap-reactive band was also observed in apoptotic cell extracts, but not in the control, untreated cell extracts (FIG. 13).

Figure 14:
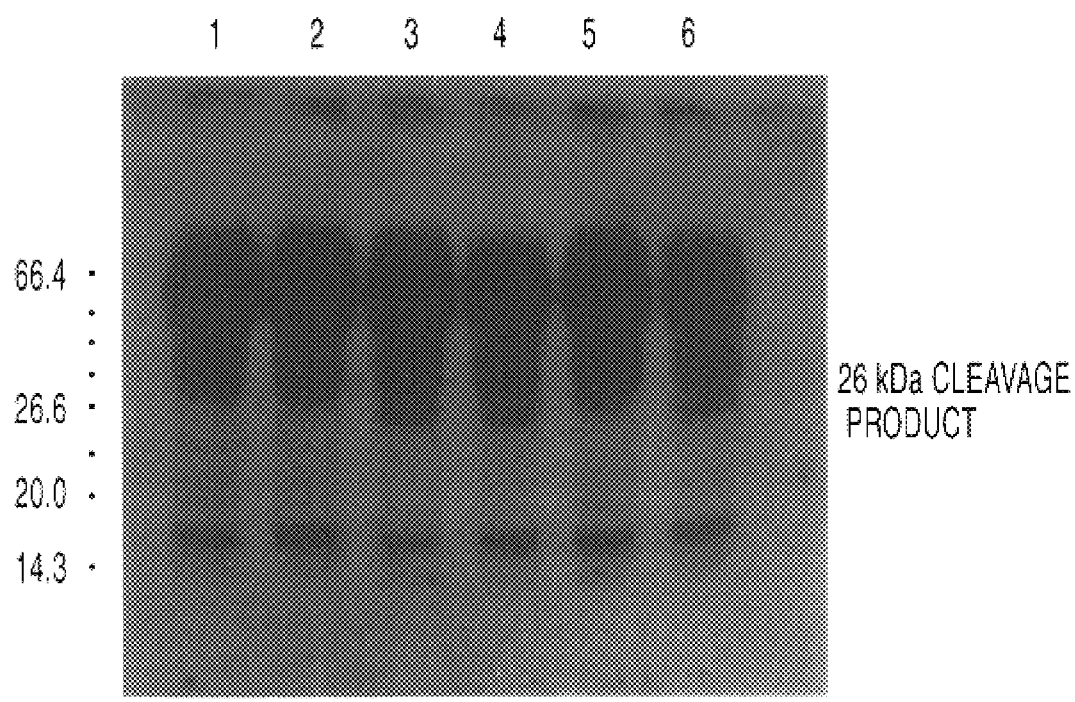
FIG. 14 is a photograph of a Western blot containing protein extracted from HeLa cells following exposure to anti-Fas antibodies. The blot was stained with a rabbit polyclonal anti-Xiap antibody. Lane 1, negative control; lane 2, cycloheximide; lane 3, anti-Fas antibody; lane 4, anti-Fas antibody and cycloheximide; lane 5, TNF-α; lane 6, TNF-α and cycloheximide.

Cleavage of Xiap occurs in a variety of cell types, including other cancer cell lines such as HeLa. The expression of the 26 kDa Xiap cleavage product was demonstrated in HeLa cells as follows. HeLa cells were treated with either: (1) cyclohexamide (20 μg/ml), (2) anti-Fas antibody (1 μg/ml), (3) anti-Fas antibody (1 μg/ml) and cyclohexamide (20 μg/ml), (4) TNFα (1,000 U/ml), or (5) TNFα (1,000 μ/ml) and cyclohexamide (20 μg/ml). All cells were harvested 18 hours after treatment began. As above, anti-Fas antibody was added to an extract after the cells were harvested. HeLa cells were harvested, and the Western blot was probed under the same conditions as used to visualize Xiap-reactive bands from Jurkat cell samples. A 26 kDa Xiap band was again seen in the apoptotic cell preparations (FIG. 14). Furthermore, the degree of Xiap cleavage correlated positively with cellular exposure to apoptotic triggers. Treatment of HeLa cells with cycloheximide or TNFα alone caused only minor apoptosis, and little cleavage product was observed. If the cells were treated with the anti-Fas antibody, a greater amount of cleavage product was apparent. These data indicate that Xiap is cleaved in more than one cell type and in response to more than one type of apoptotic trigger.

Time Course of Expression

Figures 15A, 15B:
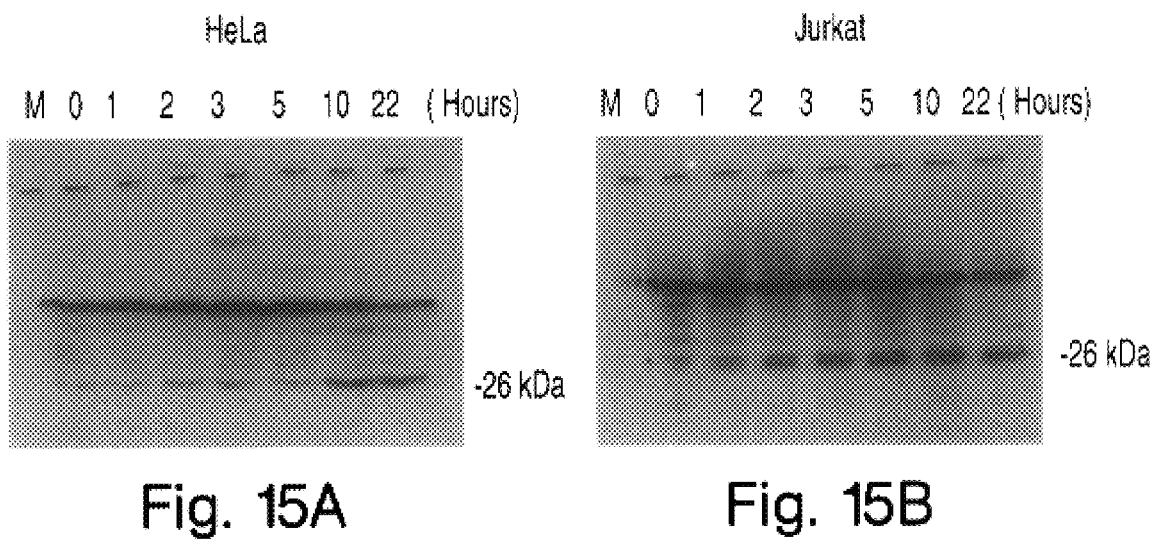
FIGS. 15A and 15B are photographs of Western blots stained with rabbit polyclonal anti-Xiap antibody. Protein was extracted from HeLa cells (FIG. 21A) and Jurkat cells (FIG. 21B) immediately, 1, 2, 3, 5, 10, and 22 hours after exposure to anti-Fas antibody.

The time course over which the 26 kDa cleavage product accumulates was examined by treating HeLa and Jurkat cells with anti-Fas antibody (1 µg/ml) and harvesting them either immediately, or 1, 2, 3, 5, 10, or 22 hours after treatment. Protein extracts were prepared and Western blot analysis was performed as described above. Both types of cells accumulated increasing quantities of the 26 kDa cleavage product over the time course examined (FIGS. 15A and 15B).

Subcellular Localization of the 26 kDa Xiap Cleavage Product

Figure 16A:
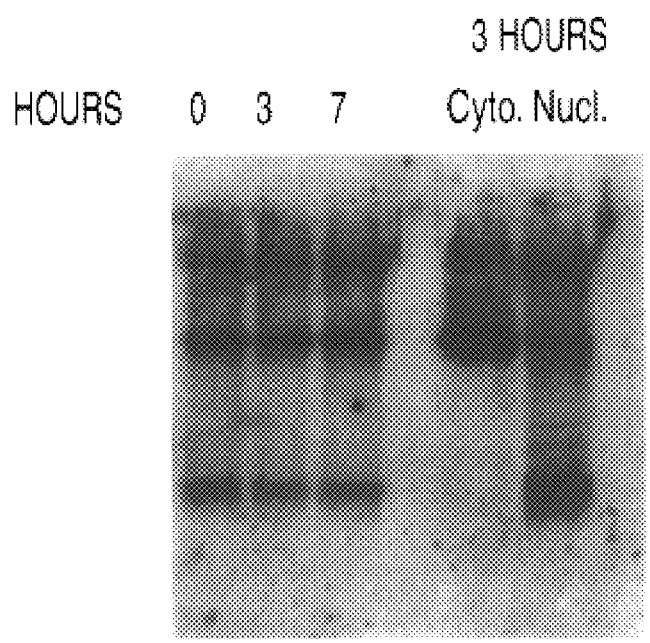
FIGS. 16A and 16B are photographs of Western blots stained with an anti-CPP32 antibody (FIG. 16A) or a rabbit polyclonal anti-Xiap antibody (FIG. 16B). Protein was extracted from Jurkat cells immediately, 3 hours, or 7 hours after exposure to an anti-Fas antibody. In addition to total protein, cytoplasmic and nuclear extracts are shown.
Figure 16B:
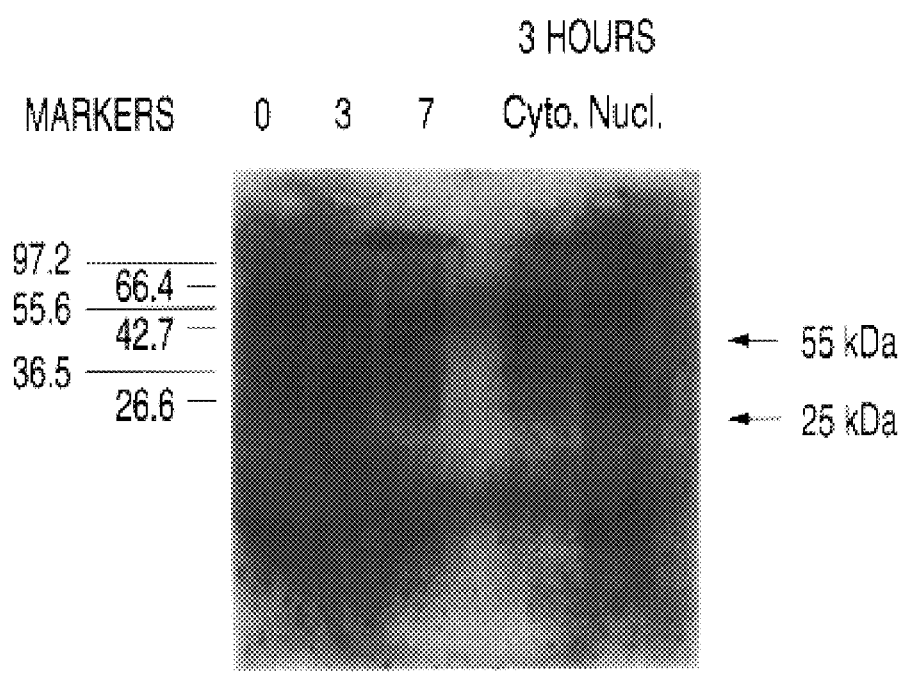

In order to determine the subcellular location of the 26 kDa cleavage product, Jurkat cells were induced to undergo apoptosis by exposure to anti-Fas antibody (1 µg/ml) and were then harvested either immediately, 3 hours, or 7 hours later. Total protein extracts were prepared, as described above, from cells harvested at each time point. In order to prepare nuclear and cytoplasmic cell extracts, apoptotic Jurkat cells were washed with isotonic Tris buffered saline (pH 7.0) and lysed by freezing and thawing five times in cell extraction buffer (50 mM PIPES, 50 mM KCl, 5 mM EGTA, 2 mM MgCl$_2$, 1 mM DTT, and 20 µM cytochalasin B). Nuclei were pelleted by centrifugation and resuspended in isotonic Tris (pH 7.0) and frozen at −80° C. The cytoplasmic fraction of the extract was processed further by centrifugation at 60,000 RPM in a TA 100.3 rotor for 30 minutes. Supernatants were removed and frozen at −80° C. Samples of both nuclear and cytoplasmic fractions were loaded on a 12.5% SDS-polyacrylamide gel, and electroblotted onto PVDF membranes. Western blot analysis was then performed using either an anti-CPP32 antibody (Transduction Laboratories Lexington, Ky.; FIG. 16A) or the rabbit anti-Xiap antibody described above (FIG. 16B).

The anti-CPP32 antibody, which recognizes the CPP32 protease (also known as YAMA or Apopain) partitioned almost exclusively in the cytoplasmic fraction. The 55 kDa Xiap protein localized exclusively in the cytoplasm of apoptotic cells, in agreement with the studies presented above, where Xiap protein in normal, healthy COS cells was seen to localize, by immunofluorescence microscopy, to the cytoplasm. In contrast, the 26 kDa cleavage product localized exclusively to the nuclear fraction of apoptotic Jurkat cells. Taken together, these observations suggest that the anti-apoptotic component of Xiap could be the 26 kDa cleavage product, which exerts its influence within the nucleus.

In vitro Cleavage of Xiap protein and Characterization of the Cleavage Product

For this series of experiments, Xiap protein was labeled with $^{35}$S using the plasmid peDNA3-6myc-XIAP, T7 RNA polymerase, and a coupled transcription/translation kit (Promega) according to the manufacturer's instructions. Radioactively labeled Xiap protein was separated from unincorporated methionine by column chromatography using Sephadex G-50™. In addition, extracts of apoptotic Jurkat cells were prepared following treatment with anti-Fas antibody (1 µg/ml) for three hours. To prepare the extracts, the cells were lysed in Triton X-100 buffer (I % Triton X-100, 25 mM Tris HCl) on ice for two hours and then microcentrifuged for 5 minutes. The soluble extract was retained (and was labeled "TX100"). Cells were lysed in cell extraction buffer with freeze/thawing. The soluble cytoplasmic fraction was set aside (and labeled "CEB"). Nuclear pellets from the preparation of the CEB cytoplasmic fraction were solubilized with Triton X-100 buffer, microcentrifuged, and the soluble fractions, which contains primarily nuclear DNA, was retained (and labeled "CEB-TX100"). Soluble cell extract was prepared by lysing cells with NP-40 buffer, followed by microcentrifugation for 5 minutes (and was labeled "NP-40"). In vitro cleavage was performed by incubating 16 µl of each extract (CEB, TX-100, CEB-TX100, and NP-40) with 4 µl of in vitro translated Xiap protein at 37° C. for 7 hours. Negative controls, containing only TX100 buffer or CEB buffer were also included. The proteins were separated on a 10% SDS-polyacrylamide gel, which was dried and exposed to X-ray film overnight.

Figure 17:
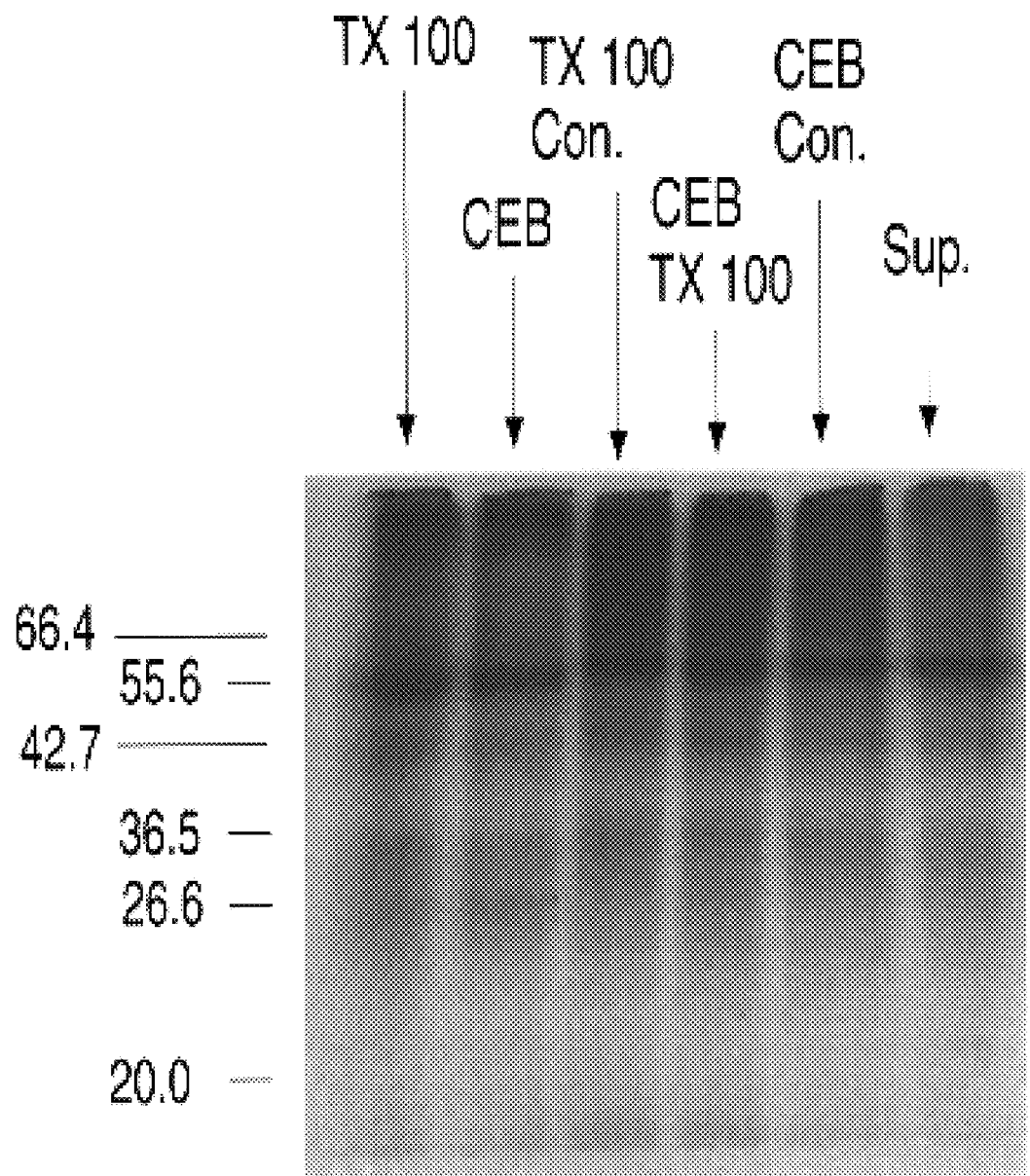
FIG. 17 is a photograph of a polyacrylamide gel following electrophoresis of the products of an in vitro Xiap cleavage assay.

In vitro cleavage of Xiap was apparent in the CEB extract. The observed molecular weight of the cleavage product was approximately 36 kDa (FIG. 17). The 10 kDa shift in the size of the cleavage product indicates that the observed product is derived from the amino-terminus of the recombinant protein, which contains six copies of the myc epitope (10 kDa). It thus appears that the cleavage product possesses at least two of the BIR domains, and that it is localized to the nucleus.

EXAMPLE 5

Characterization of IAP Activity and Intracellular Localization Studies

The ability of IAPs to modulate apoptosis can be defined in vitro systems in which alterations of apoptosis can be detected. Mammalian expression constructs carrying IAP cDNAs, which are either full-length truncated, or antisense constructs can be introduced into cell lines such as CHO, NIH 3T3, HL60, Rat-1, or Jurkat cells. In addition, SF21 insect cells may be used, in which case the IAP gene is preferentially expressed using an insect heat shock promotor. Following transfection, apoptosis can be induced by standard methods, which include serum withdrawal, or application of staurosporine, menadione (which induces apoptosis via free radial formation), or anti-Fas antibodies. As a control, cells are cultured under the same conditions as those induced to undergo apoptosis, but either not transfected, or transfected with a vector that lacks an IAP insert. The ability of each IAP related construct to inhibit or enhance apoptosis upon expression can be quantified by calculating the survival index of the cells, i.e., the ratio of surviving transfected cells to surviving control cells. These experiments can confirm the presence of apoptosis inhibiting activity and, as discussed below, can also be used to determine the functional region(s) of an IAP which may be employed to achieve enhancement of apoptosis. These assays may also be performed in combination with the application of additional compounds in order to identify compounds that enhance apoptosis via IAP expression.

EXAMPLE 6

Figure 10A:
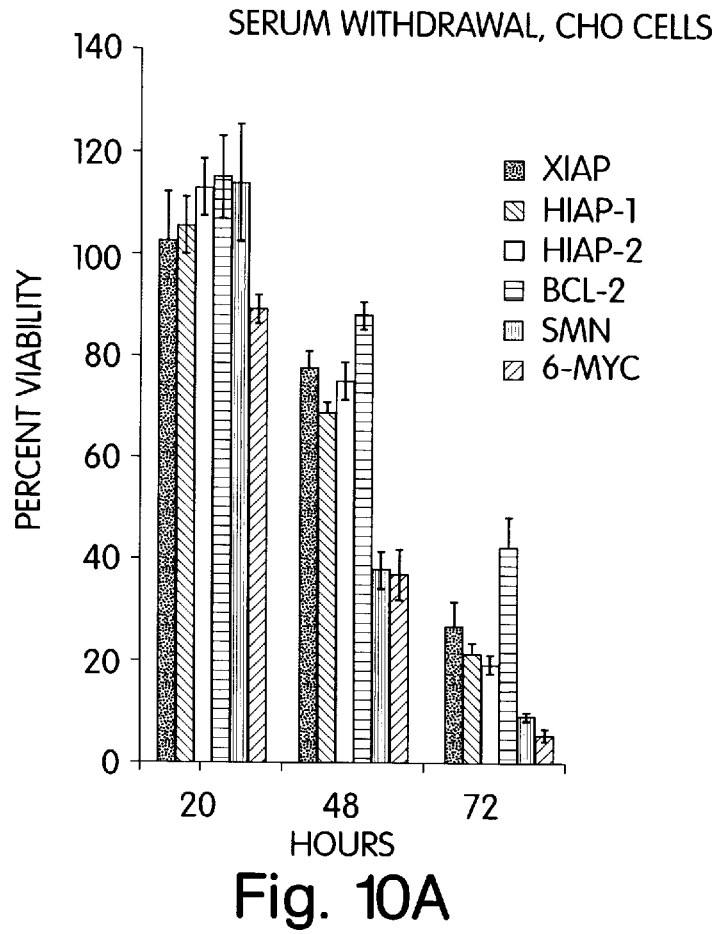
FIGS. 10A–10D are graphs depicting suppression of apoptosis by Xiap, Hiap-1, Hiap-2, Bcl-2, Smn, and 6-myc.
Figure 10B:
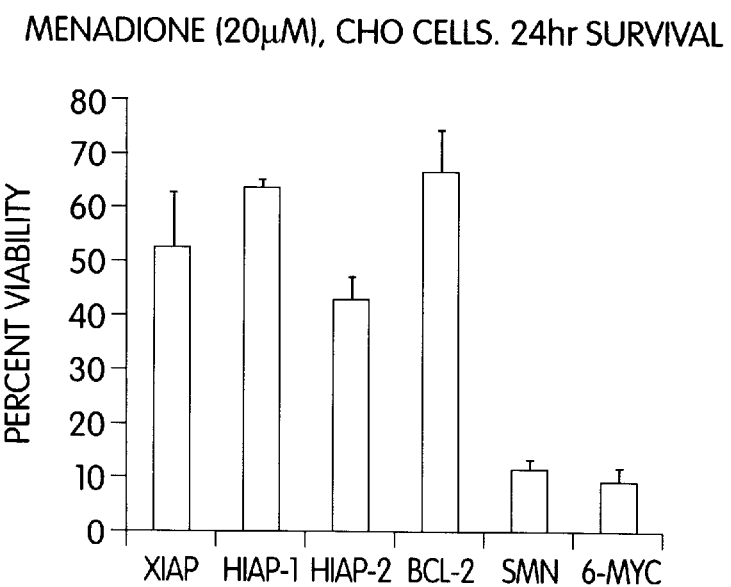

Cell Survival Following Transfection with IAP Constructs and Induction of Apoptosis Specific examples of the results obtained by performing various apoptosis suppression assays are shown in FIGS. 10A to 10D. For example, CHO cell survival following transfection with one of six constructs and subsequent serum withdrawal is shown in FIG. 10A. The cells were transfected using Lipofectace™ with 2 µg of one of the following recombinant plasmids: pcDNA36myc-xiap (xiap), pcDNA3-6myc-hiap-1 (hiap-1), pcDNA3-6myc-hiap-2 (hiap-2), pcDNA3-bcl-2 (bcl-2), pcDNA3-HA-smn (smn), and pcDNA3-6myc (6-myc). Oligonucleotide primers were synthesized to allow PCR amplification and cloning of the xiap, hiap-1, and hiap-2 ORFs in pcDNA3 (Invitrogen). Each construct was modified to incorporate a synthetic myc tag encoding six repeats of the peptide sequence MEQKLI-SEEDL (SEQ ID NO: 17), thus allowing detection of myc-IAP fusion proteins via monoclonal anti-myc antiserum (Egan et al., Nature 363:45, 1993). Triplicate samples of cell lines in 24-well dishes were washed five times with serum-free media and maintained in serum-free conditions during the course of the experiment. Cells that excluded trypan blue, and that were therefore viable, were counted with a hemocytometer immediately, 24 hours, 48 hours, and 72 hours, after serum withdrawal. Survival was calculated as a percentage of the initial number of viable cells. In this experiment and those presented in FIGS. 10B and 10D, the percentage of viable cells shown represents the average of three separate experiments performed in triplicate, ± standard deviation.

The survival of CHO cells following transfection (with each one of the six constructs described above) and exposure to menadione is shown in FIG. 10B. The cells were plated in 24-well dishes, allowed to grow overnight, and then exposed to 20 $\mu$M menadione for 1.5 hours (Sigma Chemical Co., St. Louis, Mo.). Triplicate samples were harvested at the time of exposure to menadione and 24 hours afterward, and survival was assessed by trypan blue exclusion.

Figure 10C:
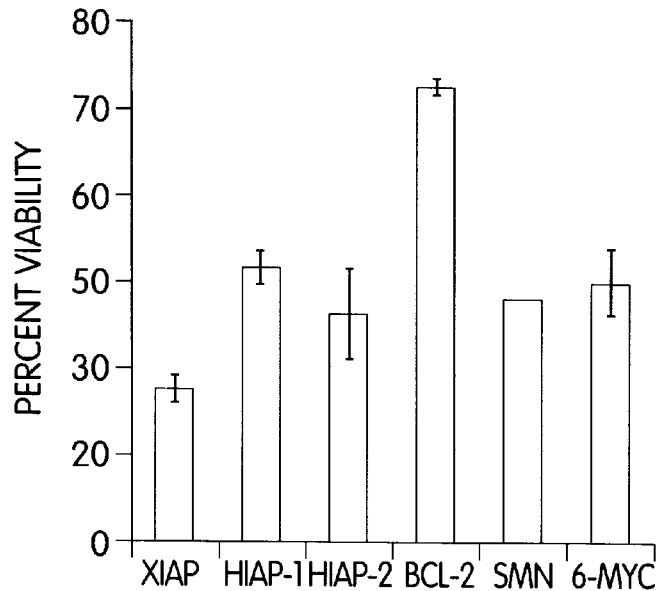
Figure 10D:
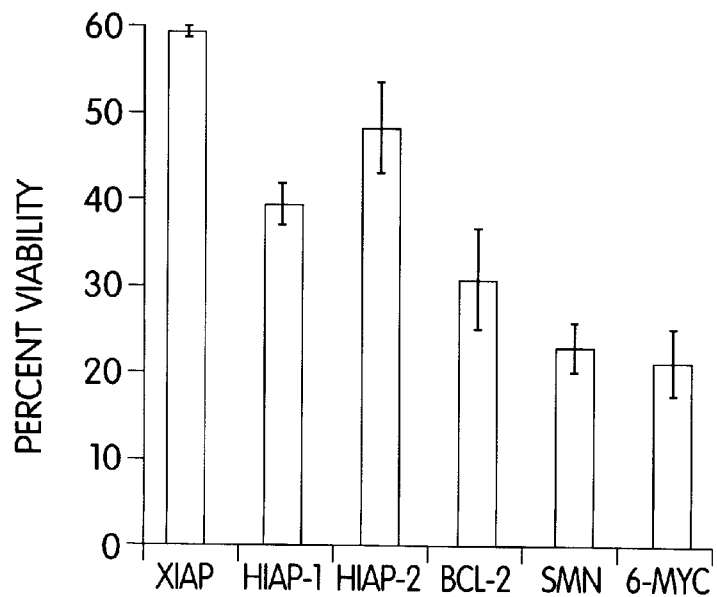

The survival of Rat-1 cells following transfection (with each one of the six constructs described above) and exposure to staurosporine is shown in FIG. 10C. Rat-1 cells were transfected and then selected in medium containing 800 $\mu$g/ml G418 for two weeks. The cell line was assessed for resistance to staurosporine-induced apoptosis (1 $\mu$M) for 5 hours. Viable cells were counted 24 hours after exposure to staurosporine by trypan blue exclusion. The percentage of viable cells shown represents the average of two experiments, ± standard deviation.

The Rat-1 cell line was also used to test the resistance of these cells to menadione (FIG. 10D) following transfection with each of the six constructs described above. The cells were exposed to 10 $\mu$M menadione for 1.5 hours, and the number of viable cells was counted 18 hours later.

EXAMPLE 7
Comparison of Cell Survival Following Transfection with Full-Length vs. Partial IAP Constructs In order to investigate the mechanism whereby human IAPs, including Xiap, Hiap-1, and Hiap-2, afford protection against cell death, expression vectors were constructed that contained either: (1) full-length IAP cDNA (as described above), (2) a portion of an IAP gene that encodes the BIR domains, but not the RZF, or (3) a portion of an IAP gene that encodes the RZF, but not the BIR domains. Human and murine xiap cDNAs were tested by transient or stable expression in HeLa, Jurkat, and CHO cell lines. Following transfection, apoptosis was induced by serum withdrawal, application of menadione, or application of an anti-Fas antibody. Cell death was then assessed, as described above, by trypan blue exclusion. As a control for transfection efficiency, the cells were co-transfected with a β-gal expression construct. Typically, approximately 20% of the cells were successfully transfected.

When CHO cells were transiently transfected, constructs containing full-length human or mouse xiap cDNAs conferred modest but definite protection against cell death. In contrast, the survival of CHO cells transfected with constructs encoding only the BIR domains (i.e., lacking the RZF domain) was markedly enhanced 72 hours after serum deprivation. Furthermore, a large percentage of cells expressing the BIR domains were still viable after 96 hours, at which time no viable cells remained in the control, i.e. non-transfected, cell cultures, and less than 5% of the cells transfected with the vector only, i.e., lacking a cDNA insert, remained viable. Deletion of any of the BIR domains results in the complete loss of apoptotic suppression, which is reflected by a decrease in the percentage of surviving CHO cells to control levels within 72 hours of serum withdrawal.

Stable pools of transfected CHO cells, which were maintained for several months under G418 selection, were induced to undergo apoptosis by exposure to 10 $\mu$M menadione for 2 hours. Among the CHO cells tested were those that were stably transfected with: (1) full-length murine xiap cDNA (miap), (2) full-length xiap cDNA (xiap), (3) full-length bcl-2 cDNA (bcl-2), (4) cDNA encoding the three BIR domains (but not the RZF) of murine xiap (BIR), and (5) cDNA encoding the RZF (but not BIR domains) of m-xiap (RZF). Cells that were non-transfected (CHO) or transfected with the vector only (pcDNA3), served as controls for this experiment. Following exposure to 10 $\mu$M menadione, the transfected cells were washed with phosphate buffered saline (PBS) and cultured for an additional 24 hours in menadione-free medium. Cell death was assessed, as described above, by trypan blue exclusion. Less than 10% of the non-transfected or vector-only transfected cells remained viable at the end of the 24 hour survival period. Cells expressing the RZF did not fare significantly better. However, expression of full-length murine xiap, human xiap, or bcl-2, and expression of the BIR domains, enhanced cell survival. When the concentration of menadione was increased from 10 $\mu$M to 20 $\mu$M (with all other conditions of the experiment being the same as when 10 $\mu$M menadione was applied), the percentage of viable CHO cells that expressed the BIR domain cDNA construct was higher than the percentage of viable cells that expressed either full-length murine xiap or bcl-2.

EXAMPLE 8
Analysis of the Subcellular Location of Expressed RZF and BIR Domains

The assays of cell death described above indicate that the RZF acts as a negative regulator of the anti-apoptotic function of IAPs. One way in which the RZF, and possibly other IAP domains, may exert their regulatory influence is by altering the expression of genes, whose products function in the apoptotic pathway.

In order to determine whether the subcellular locations of expressed RZF and BIR domains are consistent with roles as nuclear regulatory factors, COS cells were transiently transfected with the following four constructs, and the expressed polypeptide was localized by immunofluorescent microscopy: (1) pcDNA3-6myc-xiap, which encodes all 497 amino acids of SEQ ID NO:4, (2) pcDNA3-6myc-m-xiap, which encodes all 496 amino acids of mouse Xiap (SEQ ID NO:10), (3) pcDNA3-6myc-mxiap-BIR, which encodes amino acids 1 to 341 of m-Xiap (SEQ ID NO: 10), and (4) pcDNA3-6myc-mxiap-RZF, which encodes amino acids 342–496 of murine Xiap (SEQ ID NO: 10). The cells were grown on multi-well tissue culture slides for 12 hours, and then fixed and permeabilized with methanol. The constructs used (here and in the cell death assays) were tagged with a human myc epitope tag at the N-terminus. Therefore, a monoclonal anti-myc antibody and a secondary goat anti-mouse antibody, which was conjugated to FITC, could be used to localize the expressed products in transiently transfected COS cells. Full-length Xiap and Miap were located in the cytoplasm, with accentuated expression in the perinuclear zone. The same pattern of localization was observed when the cells expressed a construct encoding the RZF domain (but not the BIR domains). However, cells expressing the BIR domains (without the RZF) exhibited, primarily, nuclear staining. The protein expressed by the BIR domain construct appeared to be in various stages of transfer to the nucleus.

These observations are consistent with the fact that, as described below, Xiap is cleaved within T cells that are treated with anti-Fas antibodies (which are potent inducers of apoptosis), and its N-terminal domain is translocated to the nucleus. As noted in Example 2, Hiap-2 appears to undergo a similar cleavage event.

EXAMPLE 9

Testing of Antisense Oligonucleotides
Complete panel of adenovirus constructs.

The panel may consist of approximately four types of recombinant virus:

A) Sense orientation viruses for each of the IAP open reading frames. These viruses are designed to massively overexpress the recombinant protein in infected cells. xiap, hiap-1, hiap-2, and naip "sense" constructs arc required.

B) Antisense orientation viruses in which the viral promoter drives the synthesis of an mRNA of opposite polarity to the IAP mRNA, thereby shutting off host cell synthesis of the targeted protein coding region. xiap, hiap-1, hiap-2, and naip "antisense" constructs arc required.

C) Sub-domain expression viruses. These constructs express only a partial IAP protein in infected cells. We have data indicating that deletion of the zinc finger of Xiap renders the protein more potent in protecting cell against apoptotic triggers. This data also indicates that expression of the zinc finger alone will indicate apoptosis by functioning as a dominant-negative repressor of Xiap function. XIAP-$\Delta$ZF and XIAP-$\Delta$bir viruses are required.

D) Control viruses. Functional analysis of the IAPs requires suitable positive and negative controls for comparison. bcl-2 sense, bcl-2 antisense, p53 sense, and lacZ (negative control) viruses may be utilized.

Confirmation of recombinant adenovirus function

Verification of the sense adenovirus function involves infection of tissue culture cells and determination of protein expression levels. We have performed western blot analysis of several of the recombinant adenoviruses, including NAIP, XIAP and XIAP-$\Delta$ZF. The remaining viruses may be ready readily assessed for protein expression using the polyclonal IAP antibodies. Functional analysis of the antisense viruses may be done at the RNA level using either northern blots of total RNA harvested from infected tissue culture cells or ribonuclease protection assays. Western blot analysis of infected cells will be used to determine whether the expressed antisense RNA interferes with IAP expression in the host cell.

Documentation that IAP overexpression results in increased drug resistance

We have optimized cell death assays to allow high through-put of samples with minimal sample variation. Testing of the sense IAP adenoviruses for their ability to alter drug sensitivity of breast and pancreatic adenocarcinoma cell lines may be accomplished as follows. Cancer cell lines are infected with the recombinant viruses, cultured for 5 days, then subdivided into 24 well plates. Triplicate cell receive increasing concentrations of the anti-cancer drug under investigation. Samples are harvested at 24, 48, and 72 hours post exposure, and assayed for the number of viable cells in the well. The dose response curve is then compared to uninfected and control virus (both positive and negative) infected cells. One may document a dramatic increase in the relative resistance of the cancer cell lines when infected with the sense viruses, confirming our hypothesis that overexpression of the IAP proteins contributes to the anti-apoptotic phenotype of cancer cells. Initial experiments utilize the drugs doxorubicin, and adriamycin.

Documentation that antisense IAP overexpression results in increased drug sensitivity Having confirmed that IAP overexpression renders cancer cell more resistant to chemotherapeutic drugs, one may examine whether the antisense adenoviruses render the same cells more sensitive. The effectiveness of antisense IAP viruses relative to antisense bcl-2 virus will also be assessed as a crucial milestone.

Identification of antisense oligonucleotides

Concomitant to the adenovirus work, we have designed a series of antisense oligonucleotides to various regions of each of the IAPs. A generally accepted model of how antisense oligonucleotides function proposes that the formation of RNA/DNA duplexes in the nucleus activates cellular RNascH enzymes which then enzymatically degrade the mRNA component of the hybrid. Virtually any region of the mRNA can be targeted, and therefore choosing an appropriate sequence to target is somewhat empirical. Many factors, including secondary structure of the target mRNA and the binding affinity of the targeted sequence determine whether a particular oligonucleotide will be effective, necessitating several oligos for each IAP. Five oligonucleotides have been made for each IAP mRNA based on the available computer algorhythms for predicting binding affinities and mRNA secondary structures. These and other oligos may be tested for their ability to target their respective mRNAs for degradation using northern blot analysis.

Optimization of oligonucleotides

A secondary round of oligonucleotides may be made when effective target regions have been identified. These oligonucleotides target sequences in the immediate vicinity of the most active antisense oligonucleotides identified using methods such as those provided above. A second round of testing by northern blot analysis may be required.

Testing antisense oligonucleotides in vitro

Following successful identification and optimization of targeting oligonucleotides, one may test these in the tissue culture model system using the optimal cell lines such as those described in the cancer survey described herein. Experimental procedures may parallel those used in the recombinant antisense adenovirus work. Negative control oligonucleotides with miss-match sequences are used to establish base line or non-specific effects. Assisted transfection of the oligonucleotides using cationic lipid carriers may be compared to unassisted transfection. Confirmation of the effectiveness of specific antisense oligonucleotides prompts synthesis of oligos with modified phosphodiester linkages, such as phosphorothioate or methylimino substituted oligonucleotides. These may also be tested in vitro.

Animal modeling of antisense oligonucleotide therapies

Animal modeling of the effectiveness of the antisense IAP approach is described here. Cell lines are routinely assessed for their tumorigenic potential in "nude" mice, a hairless strain of mouse that is immunocompromised, and thus extremely susceptible to developing tumors. In the nude mouse assay, cancer cells are grown in tissue culture and then injected under the skin at multiple sites. The frequency with which these cells give rise to palpable tumors within a defined period of time provides an index of the tumorigenic potential of the cell line in the absence of interference by a functional immune system. Preliminary assessment of an antisense IAP therapeutic involves injection of cancer cells infected with the recombinant adenoviruses (sense, antisense, and control viruses) under the skin, and the tumorigenic index compared to that of untreated cells. One may also use this model to assess the effectiveness of systemic administration of antisense oligonucleotides in increasing the efficacy of anti-cancer drugs in the nude mouse model. Phosphorothioate or methylimino substituted oligonucleotides will be assessed at this stage. This type of antisense oligonucleotide has demonstrated enhanced cell permeability and slower clearance rates from the body in experimental animal models.

EXAMPLE 10
Additional Apoptosis Assays

Specific examples of apoptosis assays are also provided in the following references. Assays for apoptosis in lymphocytes are disclosed by: Li et al., Science 268:429, 1995; Gibellini et al., Br. J. Haematol. 89:24, 1995; Martin et al., J. Immunol. 152:330, 1994; Terai et al., J. Clin Invest. 87:1710, 1991; Dhein et al., Nature 373:438, 1995; Katsikis et al., J. Exp. Med. 1815:2029, 1995; Westendorp et al., Nature 375:497, 1995; DeRossi et al., Virology 198:234, 1994.

Assays for apoptosis in fibroblasts are disclosed by: Vossbeck et al., "Direct transforming activity of TGF-beta on rat fibroblasts", Int. J. Cancer 61:92–97, 1995; Goruppi et al., "Dissection of c-myc domains involved in S phase induction of NIH3T3 fibroblasts", Oncogene 9:1537–44, 1994; Fernandez et al., "Differential sensitivity of normal and Ha-ras transformed C3H mouse embryo fibroblasts to tumor necrosis factor: induction of bcl-2, c-myc, and manganese superoxide dismutase in resistant cells", Oncogene 9:2009–17, 1994; Harrington et al., "c-Myc-induced apoptosis in fibroblasts is inhibited by specific cytokines", EMBO J., 13:3286–3295, 1994; Itoh et al., "A novel protein domain required for apoptosis. Mutational analysis of human Fas antigen", J. Biol. Chem. 268:10932–7, 1993.

Assays for apoptosis in neuronal cells are disclosed by: Melino et al., Mol. Cell. Biol. 14:6584, 1994; Rosenbaum et al., Ann. Neurol. 36:864, 1994; Sato et al., J. Neurobiol. 25:1227, 1994; Ferrari et al., J. Neurosci. 1516:2857, 1995; Talley et al., Mol. Cell. Biol. 1585:2359, 1995; Talley et al., Mol. Cell. Biol. 15:2359, 1995; Walkinshaw et al., J. Clin. Invest. 95:2458, 1995.

Assays for apoptosis in insect cells are disclosed by: Clem et al., Science 254:1388, 1991; Crook et al. J. Virol. 67:2168, 1993; Rabizadeh et al., J. Neurochem. 61:2318, 1993; Birnbaum et al., J. Virol. 68:2521, 1994; Clem et al., Mol. Cell. Biol. 14:5212–5222, 1994.

EXAMPLE 11
Construction of a Transgenic Animal

Characterization of IAP genes provided information that necessary for generation IAP transgenic animal models to be developed by homologous recombination (for knockouts) or transfection (for expression of IAP fragments, antisense IAP RNA, or increased expression of wild-type or mutant IAPs). Such models may be mammalian, e.g., a mouse. Such models are useful for the identification of cancer therapeutics alone or in combination with cancer inducing cells or agents, or when such mice are crossed with mice genetically predisposed to cancers.

The preferred transgenic animal overexpression in IAP and has a predisposition to cancer. This mouse is particularly useful for the screening of potential cancer therapeutics.

EXAMPLE 12
IAP Protein Expression

IAP genes and fragments thereof (i.e. RZF fragments) may be expressed in both prokaryotic and eukaryotic cell types. If an IAP fragment modulates apoptosis by exacerbating it, it may be desirable to express that protein under control of an inducible promoter.

In general, IAPs and fragments thereof may be produced by transforming a suitable host cell with all or part of the IAP-encoding cDNA fragment that has been placed into a suitable expression vector.

Those skilled in the art of molecular biology will understand that a wide variety of expression systems may be used to produce the recombinant protein. The precise host cell used is not critical to the invention, although cancer cells are preferable. The IAP protein may be produced in a prokaryotic host (e.g., *E. coli*) or in a eukaryotic host (e.g., *S. cerevisiae*, insect cells such as Sf21 cells, or mammalian cells such as COS-1, NIH 3T3, or HeLa cells, or other highly proliferative cell types). These cells are publically available, for example, from the American Type Culture Collection, Rockville, Md.; see also Ausubel et al., supra). The method of transduction and the choice of expression vehicle will depend on the host system selected. Transformation and transfection methods are described, e.g., in Ausubel et al. (supra), and expression vehicles may be chosen from those provided, e.g. in *Cloning Vectors: A Laboratory Manual* (P. H. Pouwels et al., 1985, Supp. 1987).

Polypeptides of the invention, particularly short IAP fragments, can also be produced by chemical synthesis (e.g., by the methods described in Solid *Phase Peptide Synthesis,* 2nd ed., 1984 The Pierce Chemical Co., Rockford, Ill.). These general techniques of polypeptide expression and purification can also be used to produce and isolate useful IAP fragments or analogs, as described herein.

EXAMPLE 13
Anti-IAP Antibodies

In order to generate IAP-specific antibodies, an IAP coding sequence (e.g., amino acids 180–276) can be expressed as a C-terminal fusion with glutathione S-transferase (GST; Smith et al., Gene 67:31, 1988). The fusion protein can be purified on glutathione-Sepharose beads, eluted with glutathione, and cleaved with thrombin (at the engineered cleavage site), and purified to the degree required to successfully immunize rabbits. Primary immunizations can be carried out with Freund's complete adjuvant and subsequent immunizations performed with Freund's incomplete adjuvant. Antibody titres are monitored by Western blot and immunoprecipitation analyses using the thrombin-cleaved IAP fragment of the GST-IAP fusion protein. Immune sera are affinity purified using CNBr-Sepharose-coupled IAP protein. Antiserum specificity is determined using a panel of unrelated GST proteins (including GSTp53, Rb, HPV-16 E6, and E6-AP) and GST-trypsin (which was generated by PCR using known sequences).

As an alternate or adjunct immunogen to GST fusion proteins, peptides corresponding to relatively unique hydrophilic regions of IAP may be generated and coupled to keyhole limpet hemocyanin (KLH) through an introduced C-terminal lysine. Antiserum to each of these peptides is similarly affinity purified on peptides conjugated to BSA, and specificity is tested by ELISA and Western blotting using peptide conjugates, and by Western blotting and immunoprecipitation using IAP expressed as a GST fusion protein.

Alternatively, monoclonal antibodies may be prepared using the IAP proteins described above and standard hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerling et al., In *Monoclonal Antibodies and T Cell Hybridomas*, Elsevier, New York, N.Y., 1981; Ausubel et al., supra). Once produced, monoclonal antibodies are also tested for specific IAP recognition by Western blot or immunoprecipitation analysis (by the methods described in Ausubel et al., supra).

Antibodies that specifically recognize IAPs or fragments of IAPs, such as those described herein containing one or more BIR domains (but not a ring zinc finger domain), or that contain a ring zinc finger domain (but not a BIR domain) are considered useful in the invention. They may, for example, be used in an immunoassay to monitor IAP expression levels or to determine the subcellular location of an IAP or IAP fragment produced by a mammal. Antibodies that inhibit the 26 kDa IAP cleavage product described herein (which contains at least one BIR domain) may be especially useful in inducing apoptosis in cells undergoing undesirable proliferation.

Preferably, antibodies of the invention are produced using IAP sequence that does not reside within highly conserved regions, and that appears likely to be antigenic, as analyzed by criteria such as those provided by the Peptide structure program (Genetics Computer Group Sequence Analysis Package, Program Manual for the GCG Package, Version 7, 1991) using the algorithm of Jameson and Wolf (CABIOS 4:181, 1988). Specifically, these regions, which are found between BIR1 and BIR2 of all IAPs, are: from amino acid 99 to amino acid 170 of Hiap-1, from amino acid 123 to amino acid 184 of Hiap-2, and from amino acid 116 to amino acid 133 of either Xiap or m-Xiap. These fragments can be generated by standard techniques, e.g. by the PCR, and cloned into the pGEX expression vector (Ausubel et al., supra). Fusion proteins are expressed in *E. coli* and purified using a glutathione agarose affinity matrix as described in Ausubel et al. (supra). In order to minimize the potential for obtaining antisera that is non-specific, or exhibits low-affinity binding to IAP, two or three fusions are generated for each protein, and each fusion is injected into at least two rabbits. Antisera are raised by injections in series, preferably including at least three booster injections.

EXAMPLE 14
Identification of Molecules that Modulate IAP Protein Expression

IAP cDNAs facilitate the identification of molecules that decrease IAP expression or otherwise enhance apoptosis normally blocked by the IAPs. In one approach, candidate molecules are added, in varying concentration, to the culture medium of cells expressing IAP mRNA. IAP expression is then measured, for example, by Northern blot analysis (Ausubel et al., supra) using an IAP cDNA, or cDNA fragment, as a hybridization probe. The level of IAP expression in the presence of the candidate molecule is compared to the level of IAP expression in the absence of the candidate molecule, all other factors (e.g., cell type and culture conditions) being equal.

The effect of candidate molecules on IAP-mediated apoptosis may, instead, be measured at the level of IAP protein or level of IAP fragments using the general approach described above with standard protein detection techniques, such as Western blotting or immunoprecipitation with an IAP-specific antibody (for example, the IAP antibodies described herein).

Compounds that modulate the level of IAP may be purified, or substantially purified, or may be one component of a mixture of compounds such as an extract or supernatant obtained from cells (Ausubel et al., supra). In an assay of a mixture of compounds, IAP expression is tested against progressively smaller subsets of the compound pool (e.g., produced by standard purification techniques such as HPLC or FPLC) until a single compound or minimal number of effective compounds is demonstrated to modulate IAP expression.

Compounds may also be screened for their ability to enhance IAP-mediated apoptosis. In this approach, the degree of apoptosis in the presence of a candidate compound is compared to the degree of apoptosis in its absence, under equivalent conditions. Again, the screen may begin with a pool of candidate compounds, from which one or more useful modulator compounds are isolated in a step-wise fashion. Apoptosis activity may be measured by any standard assay, for example, those described herein.

Another method for detecting compounds that modulate the activity of IAPs is to screen for compounds that interact physically with a given IAP polypeptide. These compounds may be detected by adapting interaction trap expression systems known in the art. These systems detect protein interactions using a transcriptional activation assay and are generally described by Gyuris et al. (Cell 75:791, 1993) and Field et al. (Nature 340:245, 1989), and are commercially available from Clontech (Palo Alto, Calif.). In addition, PCT Publication WO 95/28497 describes an interaction trap assay in which proteins involved in apoptosis, by virtue of their interaction with Bcl-2, are detected. A similar method may be used to identify proteins and other compounds that interact with IAPs.

Compounds or molecules that function as modulators of IAP-mediated cell death may include peptide and non-peptide molecules such as those present in cell extracts, mammalian serum, or growth medium in which mammalian cells have been cultured.

TABLE 2

OLIGONUCLEOTIDE PRIMERS FOR THE SPECIFIC RT-PCR AMPLIFICATION OF IAP GENES

| IAP Gene | Forward Primer (nucleotide position*) | Reverse Primer (nucleotide position*) | Size of Product (bp) |
|---|---|---|---|
| h-xiap | p2415 (876–896) | p2449 (1291–1311) | 435 |
| m-xiap | p2566 (458–478) | p2490 (994–1013) | 555 |
| h-hiap1 | p2465 (827–847) | p2464 (1008–1038) | 211 |
| m-hiap1 | p2687 (747–767) | p2684 (1177–1197) | 450 |
| hiap2 | p2595 (1562–1585) | p2578 (2339–2363) | 801[a] 618[b] |
| m-hiap2 | p2693 (1751–1772) | p2734 (2078–2100) | 349 |

*Nucleotide position as determined from FIGS. 1–4 for each IAP gene
[a]PCR product size of hiap2a
[b]PCR product size of hiap2b

EXAMPLE 15
Assignment OF xiap, hiap-1, and hiap-2 to Chromosomes Xq25 and 11q22–23 by Fluorescence In Situ Hybridization (FISH)

Fluorescence in situ hybridization (FISH) was used to identify the chromosomal location of xiap, hiap-1 and hiap-2.

A total of 101 metaphase spreads were examined with the xiap probe, as described above. Symmetrical fluorescent signals on either one or both homologs of chromosome Xq25 were observed in 74% of the cells analyzed. Following staining with hiap-1 and hiap-2 probes, 56 cells were analyzed and doublet signals in the region 11q22–23 were observed in 83% of cells examined. The xiap gene was mapped to Xq25 while the hiap-1 and hiap-2 genes were mapped at the border of 11q22 and 11q23 bands.

These experiments confirmed the location of the xiap gene on chromosome Xq25. No highly consistent chromosomal abnormalities involving band Xq25 have been reported so far in any malignancies. However, deletions within this region are associated with a number of immune system defects including X-linked lymphoproliferative disease (Wu et al., Genomics 17:163, 1993).

Cytogenetic abnormalities of band 11q23 have been identified in more than 50% of infant leukemias regardless of the phenotype (Martinez-Climet et al., Leukaemia 9:1299, 1995). Rearrangements of the MLL Gene (mixed lineage leukemia or myeloid lymphoid leukemia; Ziemin Van der Poel et al., Proc. Natl. Acad. Sci. USA 88:10735, 1991) have been detected in 80% of cases with 11q23 translocation, however patients whose rearrangements clearly involved regions other than the MLL gene were also reported (Kobayashi et al., Blood 82:547, 1993). Thus, the IAP genes may follow the bcl-2 paradigm, and would therefore play an important role in cancer transformation.

Incorporation by Reference

The following documents and all the references referred to herein are incorporated by reference: U.S. Ser. No. 08/511,485, filed Aug. 4, 1995; U.S. Ser. No. 08/576,956, filed Dec. 22, 1995; PCT/IB96/01022, filed Aug. 5, 1996; U.S. Ser. No. 60/017,354, filed Apr. 26, 1996; U.S. Ser. No. 60/030,931 filed Nov. 15, 1996 (Express Mail Labeling Number RB794124826US); U.S. Ser. No. 60/030,590, filed Nov. 14, 1996 (Express Mail Labeling Number RB794124804US); U.S. Pat. No. 5,576,208, issued Nov. 19, 1996; and PCT Application IB97/00142, filed Jan. 17, 1997 claiming priority from UK 9601108.5, filed Jan. 19, 1996.

Other Embodiments

In other embodiments, the invention includes use of any protein which is substantially identical to a mammalian IAP polypeptides (FIGS. 1–6; SEQ ID NOs: 3–14); such homologs include other substantially pure naturally-occurring mammalian IAP proteins as well as allelic variants; natural mutants; induced mutants; DNA sequences which encode proteins and also hybridize to the IAP DNA sequences of FIGS. 1–6 (SEQ ID NOS: 3–14) under high stringency conditions or, less preferably, under low stringency conditions (e.g., washing at 2× SSC at 40° C. with a probe length of at least 40 nucleotides); and proteins specifically bound by antisera directed to a IAP polypeptide. The term also includes chimeric polypeptides that include a IAP portion.

The invention further includes use of analogs of any naturally-occurring IAP polypeptide. Analogs can differ from the naturally-occurring IAP protein by amino acid sequence differences, by post-translational modifications, or by both. Analogs of the invention will generally exhibit at least 85%, more preferably 90%, and most preferably 95% or even 99% identity with all or part of a naturally occurring IAP amino acid sequence. The length of sequence comparison is at least 15 amino acid residues, preferably at least 25 amino acid residues, and more preferably more than 35 amino acid residues. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring IAP polypeptide by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amino acids, e.g., D-amino acids or nonnaturally occurring or synthetic amino acids, c.g., B or y amino acids. In addition to full-length polypeptides, the invention also includes IAP polypeptide fragments. As used herein, the term "fragment," means at least 20 contiguous amino acids, preferably at least 30 contiguous amino acids, more preferably at least 50 contiguous amino acids, and most preferably at least 60 to 80 or more contiguous amino acids. Fragments of IAP polypeptides can be generated by methods known to those skilled in the art or may result from normal protein processing (e.g., removal of amino acids from the nascent polypeptide that are not required for biological activity or removal of amino acids by alternative mRNA splicing or alternative protein processing events).

Preferable fragments or analogs used according to the methods of the invention arc those which facilitate specific detection of a IAP nucleic acid or amino acid sequence in a sample to be diagnosed. Particularly useful IAP fragments for this purpose include, without limitation, the amino acid fragments shown in Table 2.

The methods of the invention may use antibodies prepared by a variety of methods. For example, the IAP or Naip polypeptide, or antigenic fragments thereof, can be administered to an animal in order to induce the production of polyclonal antibodies. Alternatively, antibodies used as described herein may be monoclonal antibodies, which are prepared using hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerling et al., In Monoclonal Antibodies and T Cell Hybridomas, Elsevier, N.Y., 1981). The invention features use of antibodies that specifically bind human or murine IAP or Naip polypeptides, or fragments thereof. In particular the invention features "neutralizing" antibodies. By "neutralizing" antibodies is meant antibodies that interfere with any of the biological activities of IAP or Naip polypeptides, particularly the ability of IAPs to inhibit apoptosis. The neutralizing antibody may reduce the ability of IAP polypeptides to inhibit polypeptides by, preferably 50%, more preferably by 70%, and most preferably by 90% or more. Any standard assay of apoptosis, including those described herein, by those incorporated by reference and those in the art, may be used to assess neutralizing antibodies.

In addition to intact monoclonal and polyclonal anti-IAP antibodies, the invention features use of various genetically engineered antibodies, humanized antibodies, and antibody fragments, including F(ab')2, Fab', Fab, Fv and sFv fragments. Antibodies can be humanized by methods known in the art, e.g., monoclonal antibodies with a desired binding specificity can be commercially humanized (Scotgene, Scotland; Oxford Molecular, Palo Alto, Calif.). Fully human antibodies, such as those expressed in transgenic animals, are also features of the invention (Green et al., Nature Genetics 7:13–21, 1994).

Ladner (U.S. Pat. Nos. 4,946,778 and 4,704,692) describes methods for preparing single polypeptide chain antibodies. Ward et al. (Nature 341:544–546, 1989) describe the preparation of heavy chain variable domains, which they term "single domain antibodies," which have high antigen-binding affinities. McCafferty et al. (Nature 348:552–554, 1990) show that complete antibody V domains can be displayed on the surface of fd bacteriophage, that the phage bind specifically to antigen, and that rare phage (one in a million) can be isolated after affinity chromatography. Boss et al. (U.S. Pat. No. 4,816,397) describe various methods for producing immunoglobulines, and immunologically functional fragments thereof, which include at least the variable domains of the heavy and light chain in a single host cell. Cabilly et al. (U.S. Pat. No. 4,816,567) describe methods for preparing chimeric antibodies.

What is claimed is:

1. A method of identifying a compound that enhances apoptosis in a cell, said cell associated with a proliferative disease, said method comprising:
   (a) providing a cell expressing an inhibitor of apoptosis (IAP) gene, wherein said IAP gene is a gene encoding a polypeptide having at least one Baculoviral IAP Repeat (BIR) domain and a ring zinc finger domain and wherein said polypeptide is capable of inhibitng apoptosis in a cell; and
   (b) contacting said cell with a candidate compound and monitoring the expression of said IAP gene, a decrease in the level of expression of said gene indicating the presence of a compound which enhances apoptosis, wherein said level of expression of said IAP gene is measured by measuring the level of biological activity of the IAP polypeptide encoded by said IAP gene and wherein said monitoring is monitoring of the polypeptide encoded by said IAP gene, and further wherein said monitoring is monitoring of the cleavage of said polypeptide, the nuclear localization of said polypeptide, the levels of said polypeptide, or monitoring the mRNA transcribed from said IAP gene.

2. The method of claim 1, wherein said IAP gene is xiap, xiap-1, hiap-2, m-xiap, m-hiap-1, or m-hiap-2.

3. A method of identifying a compound that enhances apoptosis in a cell said method comprising:
   (a) introducing a nucleic acid comprising an IAP gene into a cell by transformation, wherein said IAP gene encodes a polypeptide having at least one BIR domain and a ring zinc finger domain and is expressed in the cell wherein said polypeptide inhibits apoptosis in the cell; and
   (b) contacting said cell, and a control cell that is not transformed with an IAP gene, with a candidate compound, measuring and comparing the level of apoptosis in both the transformed and the control cell, wherein a compound that enhances apoptosis is indicated if said compound produces apoptosis in the transformed cell.

4. The method of claim 1, wherein said level of expression of said IAP gene is measured by measuring the level of biological activity of the IAP polypeptide encoded by said IAP gene.

5. The method of claim 1, wherein said monitoring is monitoring of the polypeptide encoded by said IAP gene.

6. The method of claim 5, wherein said monitoring of said polypeptide is monitoring of the cleavage of said polypeptide.

7. The method of claim 5, wherein said monitoring of said polypeptide is monitoring of the nuclear localization of said polypeptide.

8. The method of claim 5, wherein said monitoring of said polypeptide is monitoring of the levels of said polypeptide.

9. The method of claim 1, wherein said monitoring is monitoring of the mRNA transcribed from said IAP gene.

10. The method of claim 1, wherein said cell overexpresses said IAP gene.

11. The method of claim 10, wherein said IAP gene is a transgene and said cell is a rodent cell.

12. The method of claim 11, wherein said rodent also has a genetic predisposition to cancer or has cancer.

13. The method of claim 1, wherein said cell is a proliferative cell.

14. The method of claim 1, wherein said cell is from an immortalized cell line.

15. The method of claim 14, wherein said cell is from a cancer cell line.

16. The method of claim 15, wherein said cancer cell line is a HeLa cell line, a myelogenous leukemia cell line, a colorectal adenocarcinoma cell line, a Burkitt's lymphoma cell line, a promyelocytic leukemia cell line, or a melanoma cell line.

17. The method of claim 14, wherein said cell line is a T-cell line, such as H9, CEM/CM-3, 6T-CEM, or Jurkat cell lines.

18. The method of claim 1, wherein said cell is a cancerous cell.

19. The method of claim 18, wherein said cancerous cell is selected from the group consisting of an ovarian cancer cell, breast cancer cell, pancreatic cancer cell, lymphoma cell, melanoma cell, leukemia cell, and lung cancer cell.

20. The method of claim 1, wherein said cell further expresses a p53 polypeptide associated with a proliferative disease.

21. The method of claim 20, wherein said p53 polypeptide contains one or more mutations.

22. The method of claim 1, wherein said cell is in a non-human mammal.

23. The method of claim 22, wherein said mammal overexpresses said IAP gene.

24. The method of claim 22, wherein said mammal also has a genetic predisposition to cancer or has cancer.

25. The method of claim 22, wherein said level of expression of said IAP gene is measured by measuring the level of IAP biological activity of the polypeptide encoded by said IAP gene.

26. The method of claim 22, wherein said mammal is a rodent.

27. The method of claim 1, wherein said cell is in a mammal, and wherein said IAP is endogenous.

* * * * *